US006916807B2

(12) United States Patent
Freeman-Cook et al.

(10) Patent No.: US 6,916,807 B2
(45) Date of Patent: Jul. 12, 2005

(54) TRIARYL-OXY-ARYL-SPIRO-PYRIMIDINE-2, 4,6-TRIONE METALLOPROTEINASE INHIBITORS

(75) Inventors: Kevin D. Freeman-Cook, Clinton, CT (US); Mark C. Noe, Mystic, CT (US)

(73) Assignee: Pfizer Inc., New York, NY (US)

( * ) Notice: Subject to any disclaimer, the term of this patent is extended or adjusted under 35 U.S.C. 154(b) by 48 days.

(21) Appl. No.: 10/423,671

(22) Filed: Apr. 25, 2003

(65) Prior Publication Data

US 2003/0225056 A1 Dec. 4, 2003

Related U.S. Application Data

(60) Provisional application No. 60/376,157, filed on Apr. 26, 2002.

(51) Int. Cl.[7] .................... C07D 487/10; A61K 31/527; A61K 31/547; A61P 19/02
(52) U.S. Cl. .......................... 514/227.8; 544/6; 544/70; 544/180; 544/231; 514/231.5; 514/241; 514/269; 540/488; 540/492; 540/485; 540/543
(58) Field of Search .............................. 544/6, 70, 180, 544/231; 514/227.8, 231.5, 241, 269

(56) References Cited

U.S. PATENT DOCUMENTS

| 6,579,982 | B1 | 6/2003 | Blagg |
| 2002/0132822 | A1 | 9/2002 | Noe et al. |
| 2003/0096803 | A1 | 5/2003 | Noe et al. |
| 2003/0225056 | A1 | 12/2003 | Freeman-Cook et al. |
| 2004/0006057 | A1 | 1/2004 | Reiter et al. |
| 2004/0010141 | A1 | 1/2004 | Noe et al. |

FOREIGN PATENT DOCUMENTS

| EP | 606046 | 7/1994 |
| WO | 98/58925 | 12/1998 |
| WO | 00/47565 | 8/2000 |

OTHER PUBLICATIONS

Leffler, M.T. et al, "Aminophenyl–2–oxazolines as Local Anesthetics," *J. Am. Chem. Soc.*,59(11) , 2252–2258, (1937).
Malamas, M.S. et al, "New Azolidinediones as Inhibitors of Protein Tyrosine Phosphatase 1B with Antihyperglycemic Properties," *J. Med. Chem.*, 43(5), 995–1010, (2000).
Beam, et al, "Reactions of Dilithiooximes, Dilithiophenyl–hydrazones and Trilithiohydrazones with Nitriles. Acid–Cyclization to Isoxazoles or Pyrazoles," *J. Het. Chem.*, 9(2), 183–185, (1972).
Linderman, et al, "An Efficient Method for the Synthesis of Trifluoromethyl Substituted Heterocycles," *Tetrahedron Letters.*, 30(16), 2049–2052, (1989).
Cawston, et al., "A Rapid and Reproducible Assay for Collagenase Using [1–[14]C] Acetylated Collagen," *Anal. Biochem.* 99(2), 340–345, (1979).

Johnson–Wint, Barbara, "A Quantitative Collagen Film Collagenase Assay for Large Numbers of Samples," *Anal. Biochem.*, 104(1), 175–181, (1980).
Mitchell, P.G. et al., "Cloning, Expression, and Type II Collagenolytic Activity of Matrix Metalloproteinase–13 from Human Osteoarthritic Cartilage," *J. Clin. Invest.*, 97(3), 761–768, (1996).
Goodman, et al., *The Pharmacological Basis of Therapeutics*, $8^{th}$ Ed.,345–382, (1990).
Lednicer, et al.,*The Organic Chemistry of Drug Synthesis*, 1,167–277.
Katritzky, A.R. et al., "Benzotriazol–1–Ylmethyl Isocyanide, A New Synthon For CH–N=C Transfer Syntheses of α–Hydroxyaldehydes, 4–Ethoxy–2–Oxazolines and Oxazoles," *Tetrahedron Letters*, 30(48) , 6657–6660, (1989).
Anderson, B.A. et al., "Palladium–Catalyzed Cross Coupling Reactions of Oxazol–2–ylzine Chloride Derivatives," *Synthesis*, 5, 583–585, (1996).
Kashima, C., et al., "Synthesis of 2–Aryl–and 5–Alkyl–2–aryloxazoles from 2–Aryl–5–bromooxazoles," *Synthesis*, 11, 873–874, (1989).
Miyaura, N. et al., "Palladium–Catalyzed Cross–Coupling Reactions of Organoboron Compounds, " *Chem. Reviews*, 95, 2457–2483, (1995).
Gangloff, A.R. et al, "Synthesis of 3,5–disubstituted–1,2, 4–oxadiazoles using tetrabutylammonium fluoride as a mild and efficient catalyst," *Tetrahedron Letters.*, 42, 1441–1443, (2001).
Blackhall, A. et al, "Substitution Reactions of Phenylated Aza–heterocycles. Part I.," *J. Chem. Soc. Perkin Transactions II*, 773–777, (1980).
Maeda, M. et al., "Photorearrangements of Phenyloxazoles," *J. Chem. Soc, Perkin 1*, 3, 239–247, (1977).

*Primary Examiner*—Mark L. Berch
*Assistant Examiner*—Kahsay Habte
(74) *Attorney, Agent, or Firm*—Garth Butterfield; Steven R. Eck; Austin W. Zhang

(57) ABSTRACT

The present invention relates to triaryl-oxy-aryl-spiro-pyrimidine-2,4,6-trione metalloproteinase inhibitors of the formula

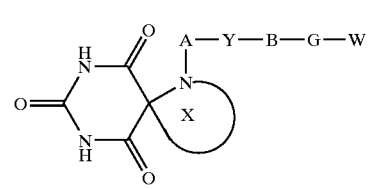

wherein said ring X is a 5–7 membered heterocyclic ring, and wherein A, Y, B, G, and W are as defined in the specification; and to pharmaceutical compositions and methods of treating inflammation, cancer and other disorders.

47 Claims, No Drawings

TRIARYL-OXY-ARYL-SPIRO-PYRIMIDINE-2,4,6-TRIONE METALLOPROTEINASE INHIBITORS

This application claims the benefit of U.S. application Ser. No. 60/376,157, filed Apr. 26, 2002.

BACKGROUND OF THE INVENTION

The present invention relates to triaryl-oxy-aryl-spiro-pyrimidine-2,4,6-trione metalloproteinase inhibitors and to pharmaceutical compositions and methods of treatment of inflammation, cancer and other disorders.

The compounds of the present invention are inhibitors of zinc metalloendopeptidases, especially those belonging to the class of matrix metalloproteinases (also called MMP or matrixin).

The MMP subfamily of enzymes currently contains seventeen members (MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19, MMP-20). The MMPs are most well known for their role in regulating the turn-over of extracellular matrix proteins and as such play important roles in normal physiological processes such as reproduction, development and differentiation. In addition, the MMPs are expressed in many pathological situations in which abnormal connective tissue turnover is occurring. For example, MMP-13 an enzyme with potent activity at degrading type II collagen (the principal collagen in cartilage), has been demonstrated to be overexpressed in osteoarthritic cartilage (Mitchell, et al., *J. Clin. Invest.*, 97, 761 (1996)). Other MMPs (MMP-2, MMP-3, MMP-8, MMP-9, MMP-12) are also overexpressed in osteoarthritic cartilage and inhibition of some or all of these MMPs is expected to slow or block the accelerated loss of cartilage typical of joint diseases such as osteoarthritis or rheumatoid arthritis.

It is recognized that different combinations of MMPs are expressed in different pathological situations. As such, inhibitors with specific selectivities for individual MMPs may be preferred for individual diseases.

Matrix metalloproteinase inhibitors are well known in the literature. Hydroxamic acid MMP inhibitors are exemplified in European Patent Publication 606,046, published Jul. 13, 1994. Several pyrimidine-2,4,6-trione MMP inhibitors are referred to in PCT publication WO 98/58925, published Dec. 30, 1998. PCT publication WO 00/47565, published Aug. 17, 2000 refers to certain aryl substituted pyrimidine-2,4,6-trione MMP inhibitors. U.S. Non-provisional application Ser. No. 09/635,156, filed Aug. 9, 2000 (which claims priority to U.S. Provisional application No. 60/148,547 filed Aug. 12, 1999) refers to heteroaryl substituted pyrimidine-2,4,6-trione MMP inhibitors. U.S. Provisional Applications entitled "Triaryloxy-Aryloxy-Pyrimidine-2,4,6-Trione Metalloproteinase Inhibitors"; "N-Substituted-Heteroaryloxy-Aryl-Spiro-Pyrimidine-2,4,6-Trione Metalloproteinase Inhibitors"; and "N-Substituted-Heteroaryloxy-Aryloxy-Pyrimidine-2,4,6-Trione Metalloproteinase Inhibitors" all filed Apr. 26, 2002, refer to certain pyrimidine-2,4,6-triodes. Barbituric acids and methods for their preparation are well known in the art, see for example Goodman and Glean's, "The Pharmacological Basis of Therapeutics," 345–382 (Eighth Edition, McGraw Hill, 1990). Each of the above referenced publications and applications is hereby incorporated by reference in its entirety.

U.S. Non-provisional application Ser. No. 10/047,592, filed 23 Oct. 2001 (which claims priority to U.S. Provisional application No. 60/243,389 filed 26 Oct. 2000) refers to heteroaryl substituted pyrimidine-2,4,6-trione MMP inhibitors. U.S. Non-provisional application Ser. No. 10/032,837, filed 25 Oct. 2001 (which claims priority to U.S. Provisional application No. 60/243,314, filed 26 Oct. 2000) refers to heteroaryl substituted pyrimidine-2,4,6-trione MMP inhibitors. Each of the above referenced applications refer to certain heteroaryl substituted pyrimidine-2,4,6-trione MMP inhibitors containing N-methylazetidinyl or N-methylpiperidinyl. Each of the above referenced applications is hereby incorporated by reference in its entirety.

SUMMARY OF THE INVENTION

The present invention relates to compounds compound of the formula:

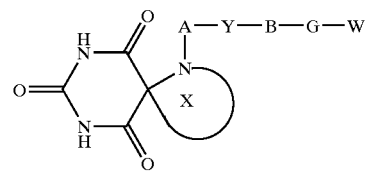

I wherein said ring X is a 5–7 membered -heterocyclic ring selected from the group consisting of:

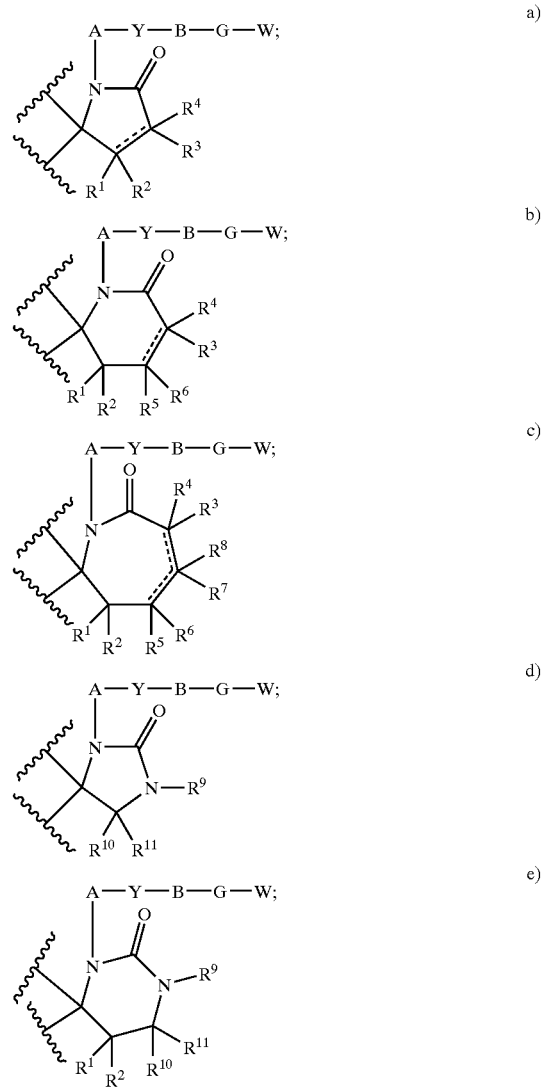

-continued

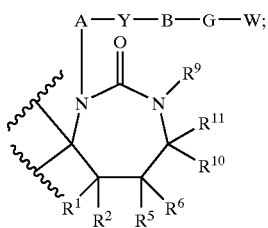

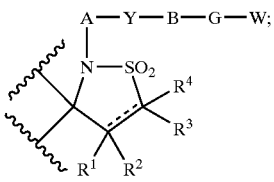

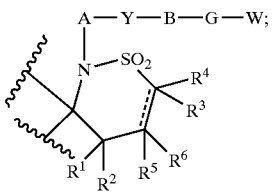

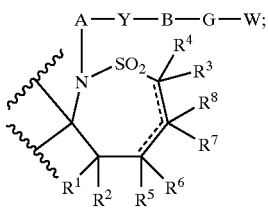

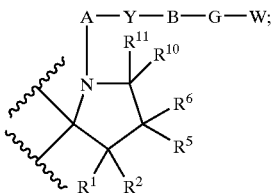

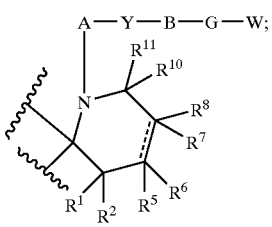

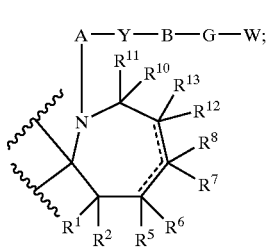

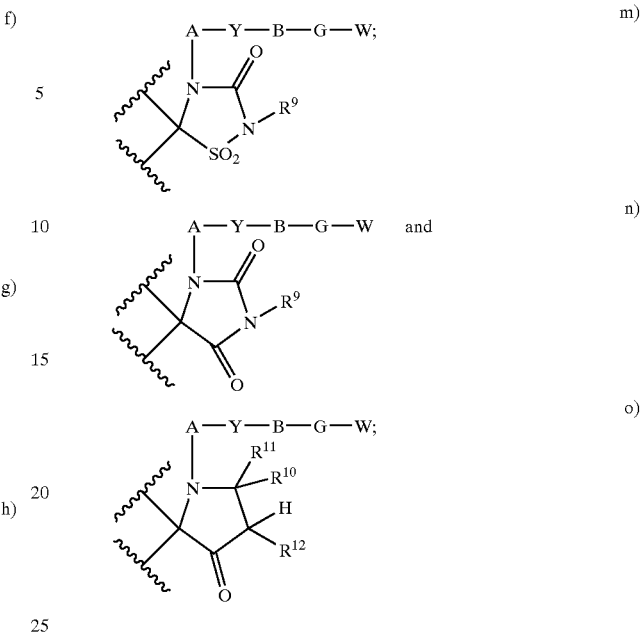

where in each dashed line represents an optional double bond;

wherein each of $R^1$, $R^2$, $R^3$, $R^4$, $R^5$, $R^6$, $R^7$, $R^8$, $R^9$, $R^{10}$, $R^{11}$, $R^{12}$ and $R^{13}$ is independently selected from the group consisting of hydrogen, $(C_1-C_4)$alkyl, $(C_1-C_4)$alkenyl, $(C_1-C_4)$alkynyl, $(C_6-C_{10})$aryl, $(C_1-C_{10})$heteroaryl, $(C_3-C_7)$cycloalkyl and $(C_1-C_{10})$heterocyclyl;

wherein each of said $R^1$, $R^2$, $R^3$, $R^4$, $R^5$, $R^6$, $R^7$, $R^8$, $R^9$, $R^{10}$, $R^{11}$, $R^{12}$ and $R^{13}$ $(C_1-C_4)$alkyl may be optionally substituted by one to three substituents independently selected from the group consisting of F, Cl, Br, CN, OH, —(C=O)—OH, —(C=O)—O—$(C_1-C_4)$alkyl, —(C=O)—$NH_2$, —(C=O)—NH—$(C_1-C_4)$alkyl, —(C=O)—N[$(C_1-C_4)$alkyl]$_2$, $(C_1-C_4)$perfluoroalkyl, $(C_1-C_4)$perfluoroalkoxy, $(C_1-C_4)$alkoxy, —$NH_2$, —$NO_2$, $(C_1-C_4)$alkyl-NH—, [$(C_1-C_4)$alkyl]$_2$-N— and $(C_3-C_7)$cycloalkoxy;

wherein each of said $R^1$, $R^2$, $R^3$, $R^4$, $R^5$, $R^6$, $R^7$, $R^8$, $R^9$, $R^{10}$, $R^{11}$, $R^{12}$ and $R^{13}$ $(C_6-C_{10})$aryl, $(C_1-C_{10})$heteroaryl, $(C_3-C_7)$cycloalkyl and $(C_1-C_{10})$heterocyclyl may be optionally substituted on any of the ring carbon atom capable of supporting an additional substituent with one to three substituents per ring independently selected from F, Cl, Br, CN, OH, —(C=O)—OH, —(C=O)—O—$(C_1-C_4)$alkyl, —(C=O)—$NH_2$, —(C=O)—NH—$(C_1-C_4)$alkyl, —(C=O)—N[$(C_1-C_4)$alkyl]$_2$, $(C_1-C_4)$perfluoroalkyl, $(C_1-C_4)$perfluoroalkoxy, $(C_1-C_4)$alkoxy, —$NH_2$, —$NO_2$, $(C_1-C_4)$alkyl-NH—, [$(C_1-C_4)$alkyl]$_2$-N— and $(C_3-C_7)$cycloalkyloxy;

wherein each of said $R^1$, $R^2$, $R^3$, $R^4$, $R^5$, $R^6$, $R^7$, $R^8$, $R^9$, $R^{10}$, $R^{11}$, $R^{12}$ and $R^{13}$ $(C_1-C_{10})$heteroaryl and $(C_1-C_{10})$heterocyclyl may optionally be substituted on any ring nitrogen atom able to support an additional substituent with one to two substituents per ring independently selected from the group consisting of $(C_1-C_4)$alkyl and $(C_1-C_4)$alkyl-(C=O)—;

wherein each of said each of said $R^1$, $R^2$, $R^3$, $R^4$, $R^5$, $R^6$, $R^7$, $R^8$, $R^9$, $R^{10}$, $R^{11}$, $R^{12}$ and $R^{13}$ $(C_3-C_7)$cycloalkyl and $(C_1-C_{10})$heterocyclyl may be also optionally substituted on any of the ring carbon atom capable of supporting two additional substituents with one to two oxo groups per ring;

A is $(C_6-C_{10})$aryl or $(C_1-C_{10})$heteroaryl;

Y is selected from the group consisting of a bond, —O—, —S—, >C=O, >SO$_2$, >S=O, —CH$_2$O—, —OCH$_2$—, —CH$_2$S—, —SCH$_2$—, —CH$_2$SO—, —CH$_2$SO$_2$—, —SOCH$_2$—, —SO$_2$CH$_2$—, >NR$^{14}$, —[N(R$^{14}$)]CH$_2$—, —CH$_2$[N(R$^{14}$)]—, —CH$_2$—, —CH=CH—, —C≡C—, —[N(R$^{14}$)]—SO$_2$— and —SO$_2$[N(R$^{14}$)]—;

R$^{14}$ is selected from the group consisting of hydrogen and $(C_1-C_4)$alkyl;

B is selected from the group consisting of $(C_6-C_{10})$aryl, $(C_3-C_7)$cycloalkyl, $(C_1-C_{10})$heterocyclyl and $(C_1-C_{10})$heteroaryl; wherein one or two carbon-carbon single bonds of said B $(C_3-C_7)$cycloalkyl or $(C_1-C_{10})$heterocyclyl may optionally be replaced by carbon-carbon double bonds;

wherein G is bonded to one ring carbon atom of B;

wherein each of said A or B may be independently optionally substituted on any of the ring carbon atom capable of supporting an additional substituent by one or two substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_7)$cycloalkyloxy;

G is —[R$^{15}$—(CR$^{16}$R$^{17}$)$_p$]—; wherein the group —B—G—W has the formula —B—[R$^{15}$—(CR$^{16}$R$^{17}$)$_p$]—W or —B—[(CR$^{16}$R$^{17}$)$_p$—R$^{15}$]—W;

p is an integer from zero to four;

R$^{15}$ is independently selected from the group consisting of $(C_3-C_7)$cycloalkyl, $(C_6-C_{10})$aryl, $(C_1-C_{10})$heteroaryl and $(C_1-C_{10})$heterocyclyl;

wherein each of said R$^{15}$ $(C_3-C_7)$cycloalkyl, $(C_6-C_{10})$aryl, $(C_1-C_{10})$heteroaryl and $(C_1-C_{10})$heterocyclyl may be optionally substituted on any of the ring carbon atom capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, —NH$_2$, —NO$_2$, $(C_1-C_4)$alkyl-NH—, [$(C_1-C_4)$alkyl]$_2$-N—; $(C_3-C_7)$cycloalkyloxy, —(C=O)—OH, —(C=O)—O—$(C_1-C_4)$alkyl, —(C=O)—NH$_2$, —(C=O)—NH—$(C_1-C_4)$alkyl, and —(C=O)—N[$(C_1-C_4)$alkyl]$_2$;

wherein each of said R$^{15}$ $(C_3-C_7)$cycloalkyl and $(C_1-C_{10})$heterocyclyl may optionally be substituted on any ring carbon atom capable of supporting two additional substituents with one to two oxo groups per ring;

wherein each of said R$^{15}$ $(C_1-C_{10})$heteroaryl and $(C_1-C_{10})$heterocyclyl may optionally be substituted on any ring nitrogen atom able to support an additional substituent independently selected from the group consisting of $(C_1-C_4)$alkyl and $(C_1-C_4)$alkyl-(C=O)—;

each of R$^{16}$ and R$^{17}$ is independently selected from the group consisting of hydrogen and $(C_1-C_4)$alkyl;

or R$^{16}$ and R$^{17}$ may optionally be taken together with the carbon to which they are attached to form a 3 to 8-membered carbocyclic ring;

W is selected from the group consisting of $(C_1-C_4)$alkoxy $(C_1-C_4)$alkyl, $(C_3-C_7)$cycloalkyl, $(C_6-C_{10})$aryl, $(C_1-C_{10})$heteroaryl and $(C_1-C_{10})$heterocyclyl;

wherein each of said W $(C_3-C_7)$cycloalkyl, $(C_6-C_{10})$aryl, $(C_1-C_{10})$heteroaryl and $(C_1-C_{10})$heterocyclyl may be optionally substituted on any of the ring carbon atom capable of supporting an additional substituent by one to three substituents per ring independently selected from F, Cl, Br, CN, OH, $(C_1-C_4)$alkyl, $(C_1-C_4)$alkoxy$(C_1-C_4)$alkyl, $(C_1-C_4)$perfluoroalkyl, $(C_1-C_4)$perfluoroalkoxy, $(C_1-C_4)$alkoxy, and $(C_3-C_7)$cycloalkyloxy;

wherein each of said W $(C_3-C_7)$cycloalkyl and $(C_1-C_{10})$heterocyclyl may optionally be substituted on any ring carbon atom capable of supporting two additional substituents with one to two oxo groups per ring;

wherein each of said W $(C_1-C_{10})$heteroaryl and $(C_1-C_{10})$heterocyclyl may optionally be substituted on any ring nitrogen atom able to support an additional substituent independently selected from the group consisting of $(C_1-C_4)$alkyl and $(C_1-C_4)$alkyl-(C=O)—;

or the pharmaceutically acceptable salts thereof.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, para-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine (meglumine), and the lower alkanolammonium and other base salts of pharmaceutically acceptable organic amines.

The compounds of this invention include all stereoisomers (e.g., cis and trans isomers) and all optical isomers of compounds of the formula I (e.g., R and S enantiomers), as well as racemic, diastereomeric and other mixtures of such isomers.

The compounds of the invention may also exist in different tautomeric forms. This invention relates to all tautomers of formula I.

The compounds of this invention may contain olefin-like double bonds. When such bonds are present, the compounds of the invention exist as cis and trans configurations and as mixtures thereof.

Some compounds of formula I contain chiral centers and therefore exist in different enantiomeric forms. This invention relates to all optical isomers, enantiomers, diastereomers and stereoisomers of the compounds of formula I and mixtures thereof. The compounds of the invention also exist in different tautomeric forms. This invention relates to all tautomers of formula I. Those skilled in the art are well aware that the pyrimidine-2,4,6-trione nucleus exists as a mixture of tautomers in solution. The various ratios of the tautomers in solid and liquid form is dependent on the various substituents on the molecule as well as the particular crystallization technique used to isolate a compound.

Unless otherwise indicated, the term "substituent" or "substituents" refers to a replacement of at least one atom of an individual member of a variable (e.g., R$^1$, R$^2$, and R$^3$) of the compound of the formula I by another atom or group of atoms. For example, an $(C_1-C_6)$alkyl substituent may replace a hydrogen atom of the R$^1$ $(C_6-C_{10})$aryl.

Unless otherwise indicated, the term "$(C_1-C_4)$alkyl" or "$(C_1-C_6)$alkyl", as well as the $(C_1-C_4)$alkyl or $(C_1-C_6)$alkyl component of other terms referred to herein (e.g., the "$(C_1-C_6)$alkyl component of $(C_1-C_6)$alkyl-O—"), may be linear or branched (such as methyl, ethyl, n-propyl, isopropyl, n-butyl, iso-butyl, secondary-butyl, tertiary-butyl) hydrocarbon chain of 1 to 4, or 1 to 6, carbon atoms.

Unless otherwise indicated, the term "halo" means fluoro, chloro, bromo or iodo.

Unless otherwise indicated, the term "$(C_2-C_6)$alkenyl" means straight or branched hydrocarbon chain of 2 to 6 carbon atoms having at least one double bond including, but not limited to ethenyl, 1-propenyl, 2-propenyl (allyl), isopropenyl, 2-methyl-1-propenyl, 1-butenyl, or 2-butenyl.

Unless otherwise indicated, the term "$(C_2-C_6)$alkynyl" is used herein to mean straight or branched hydrocarbon chain of 2 to 6 carbon atoms having one triple bond including, but not limited to, ethynyl (—C≡C—H), propynyl (—CH$_2$—C≡C—H or —C≡C—CH$_3$), or butynyl (—CH$_2$—CH$_2$—C≡C—H, or —CH$_2$—C≡C—CH$_3$, or —C≡C—CH$_2$CH$_3$).

Unless otherwise indicated, the term "$(C_3-C_7)$cycloalkyl" refers to a mono or bicyclic carbocyclic ring of 3 to 7 carbon atoms including, but not limited to, cyclopropyl, cyclobutyl, cyclopentyl, cyclohexyl, cycloheptyl and bicyclo[2.2.1]heptanyl; wherein said $(C_3-C_7)$cycloalkyl may optionally contain 1 or 2 double bonds including, but not limited to, cyclopentenyl, cyclohexenyl and cycloheptenyl.

Unless otherwise indicated, the term "$(C_6-C_{10})$aryl" refers to an aromatic ring such as phenyl, naphthyl, tetrahydronaphthyl, or indanyl.

Unless otherwise indicated, the term "oxo" refers to a carbonyl group (ie., =O).

Unless otherwise indicated, the term "$(C_1-C_{10})$heteroaryl" refers to aromatic or multicyclic rings wherein at least one ring is aromatic, wherein said aromatic or multicyclic rings contain one or more heteroatoms selected from the group consisting of O, S and N. Examples of $(C_1-C_{10})$heteroaryl include, but are not limited to, benzimidazolyl, benzofuranyl, benzofurazan,yl, 2H-1-benzopyranyl, benzothiadiazine, benzothiazinyl, benzothiazolyl, benzothiophenyl, benzoxazolyl, chromanyl, cinnolinyl, furazanyl, furopyridinyl, furyl, imidazolyl, indazolyl, indolinyl, indolizinyl, indolyl, 3H-indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, pyridinyl, pyrimidinyl, pyrazolyl, pyrrolyl, quinazolinyl, quinolinyl, quinoxalinyl, tetrazolyl, thiazolyl, thiadiazolyl, thienyl, triazinyl and triazolyl. Unless otherwise indicated, the foregoing $(C_1-C_{10})$heteroaryl can be C-attached or N-attached where such is possible.

Unless otherwise indicated, the term "$(C_1-C_{10})$heterocyclyl" refers to a ring containing 1 to 10 carbon atoms and 1 to 4 heteroatoms selected from the group consisting of N, O and S. Examples of $(C_1-C_{10})$heterocyclyl include, but not limited to, 3-azabicyclo[3.1.0]hexanyl, 3-azabicyclo[4.1.0]-heptanyl, azetidinyl, dihydrofuranyl, dihydropyranyl, dihydrothienyl, dioxanyl, 1,3-dioxolanyl, 1,4-dithianyl, hexahydroazepinyl, hexahydropyrimidine, imidazolidinyl, imidazolinyl, isoxazolidinyl, morpholinyl, oxetanyl oxazolidinyl, piperazinyl, piperidinyl, 2H-pyranyl, 4H-pyranyl, pyrazolidinyl, pyrazolinyl, pyrrolidinyl, 2-pyrrolinyl, 3-pyrrolinyl, quinolizinyl, tetrahydrofuranyl, tetrahydropyranyl, 1,2,3,6-tetrahydropyridinyl, tetrahydrothienyl, tetrahydrothiopyranyl, thiomorpholinyl, thioxanyl or trithianyl. Unless otherwise indicated, the foregoing $(C_1-C_{10})$heterocyclyl can be C-attached or N-attached where such is possible. For example, piperidinyl can be piperidin-1-yl (N-attached) or piperidin-4-yl (C-attached).

In one embodiment of the invention, the heterocyclic ring X has the formula a):

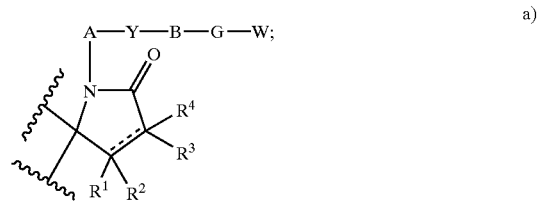

and wherein each of $R^1$, $R^2$, $R^3$, and $R^4$ is independently selected from the group consisting of hydrogen, $(C_1-C_4)$alkyl, $(C_1-C_4)$alkenyl, $(C_1-C_4)$alkynyl, $(C_6-C_{10})$aryl, $(C_1-C_{10})$heteroaryl, $(C_3-C_7)$cycloalkyl and $(C_1-C_{10})$heterocyclyl.

In one embodiment of the invention, the heterocyclic ring X has the formula $a_1$) (i.e. the heterocyclic ring X of formula a), wherein in the heterocyclic ring X the dashed line is a double bond):

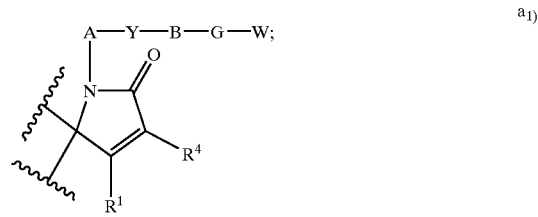

and wherein each of $R^1$ and $R^4$ is independently selected from the group consisting of hydrogen, $(C_1-C_4)$alkyl, $(C_1-C_4)$alkenyl, $(C_1-C_4)$alkynyl, $(C_6-C_{10})$aryl, $(C_1-C_{10})$heteroaryl, $(C_3-C_7)$cycloalkyl and $(C_1-C_{10})$heterocyclyl.

In another embodiment of the invention, the heterocyclic ring X has the formula b:

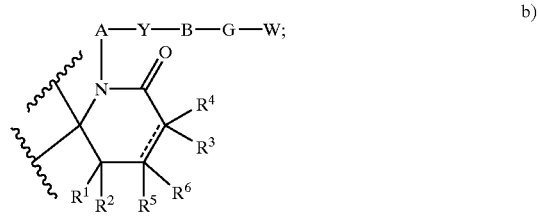

and wherein each of $R^1$, $R^2$, $R^3$, $R^4$, $R^5$, and $R^6$ is independently selected from the group consisting of hydrogen, $(C_1-C_4)$alkyl, $(C_1-C_4)$alkenyl, $(C_1-C_4)$alkynyl, $(C_6-C_{10})$aryl, $(C_1-C_{10})$heteroaryl, $(C_3-C_7)$cycloalkyl and $(C_1-C_{10})$heterocyclyl.

In another embodiment of the invention, the heterocyclic ring X has the formula $b_1$) (i.e. the heterocyclic ring X of formula b), wherein in the heterocyclic ring X the dashed line is a double bond):

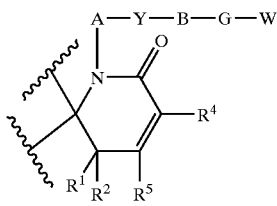

and wherein each of $R^1$, $R^2$, $R^4$, and $R^5$ is independently selected from the group consisting of hydrogen, $(C_1-C_4)$ alkyl, $(C_1-C_4)$alkenyl, $(C_1-C_4)$alkynyl, $(C_6-C_{10})$aryl, $(C_1-C_{10})$heteroaryl, $(C_3-C_7)$cycloalkyl and $(C_1-C_{10})$ heterocyclyl.

In another embodiment of the invention, the heterocyclic ring X has the formula c):

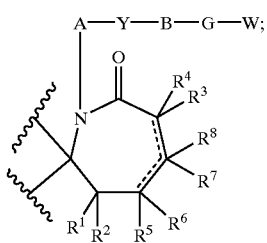

and wherein each of $R^1$, $R^2$, $R^3$, $R^4$, $R^5$, $R^6$, $R^7$, and $R^8$ is independently selected from the group consisting of hydrogen, $(C_1-C_4)$alkyl, $(C_1-C_4)$alkenyl, $(C_1-C_4)$alkynyl, $(C_6-C_{10})$aryl, $(C_1-C_{10})$heteroaryl, $(C_3-C_7)$cycloalkyl and $(C_1-C_{10})$heterocyclyl.

In another embodiment of the invention, the heterocyclic ring X has the formula $c_1$) or $c_2$) (i.e. the heterocyclic ring X of formula c), wherein in the heterocyclic ring X the dashed line is a double bond):

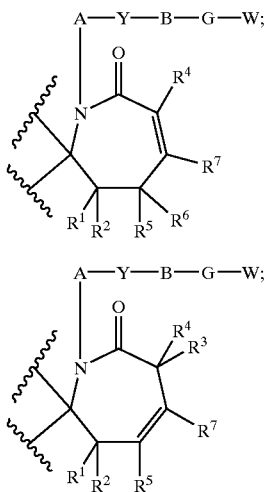

and wherein each of $R^1$, $R^2$, $R^3$, $R^4$, $R^5$, $R^6$, and $R^7$ is independently selected from the group consisting of hydrogen, $(C_1-C_4)$alkyl, $(C_1-C_4)$alkenyl, $(C_1-C_4)$alkynyl, $(C_6-C_{10})$aryl, $(C_1-C_{10})$heteroaryl, $(C_3-C_7)$cycloalkyl and $(C_1-C_{10})$heterocyclyl.

In another embodiment of the invention, the heterocyclic ring X has the formula d):

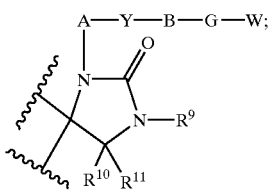

wherein each of $R^{10}$ and $R^{11}$ is independently selected from the group consisting of hydrogen, $(C_1-C_4)$alkyl, $(C_1-C_4)$alkenyl, $(C_1-C_4)$alkynyl, $(C_6-C_{10})$aryl, $(C_1-C_{10})$heteroaryl, $(C_3-C_7)$cycloalkyl and $(C_1-C_{10})$heterocyclyl; and $R^9$ is selected from hydrogen and $(C_1-C_4)$alkyl.

In another embodiment of the invention, the heterocyclic ring X has the formula e):

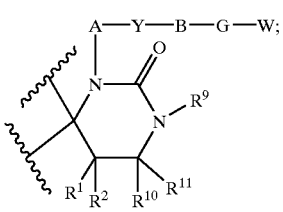

wherein each of $R^1$, $R^2$, $R^{10}$ and $R^{11}$ is independently selected from the group consisting of hydrogen, $(C_1-C_4)$ alkyl, $(C_1-C_4)$alkenyl, $(C_1-C_4)$alkynyl, $(C_6-C_{10})$aryl, $(C_1-C_{10})$heteroaryl, $(C_3-C_7)$cycloalkyl and $(C_1-C_{10})$ heterocyclyl; and $R^9$ is selected from hydrogen and $(C_1-C_4)$ alkyl.

In another embodiment of the invention, the heterocyclic ring X has the formula f):

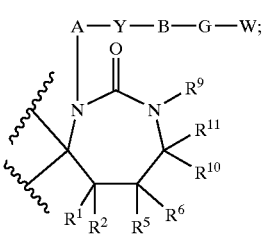

wherein each of $R^1$, $R^2$, $R^5$, $R^6$, $R^{10}$ and $R^{11}$ is independently selected from the group consisting of hydrogen, $(C_1-C_4)$alkyl, $(C_1-C_4)$alkenyl, $(C_1-C_4)$alkynyl, $(C_6-C_{10})$ aryl, $(C_1-C_{10})$heteroaryl, $(C_3-C_7)$cycloalkyl and $(C_1-C_{10})$ heterocyclyl; and $R^9$ is selected from hydrogen and $(C_1-C_4)$ alkyl.

In another embodiment of the invention, the heterocyclic ring X has the formula g):

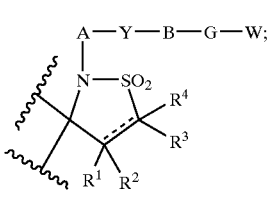

and wherein each of $R^1$, $R^2$, $R^3$, and $R^4$ is independently selected from the group consisting of hydrogen, $(C_1-C_4)$ alkyl, $(C_1-C_4)$alkenyl, $(C_1-C_4)$alkynyl, $(C_6-C_{10})$aryl, $(C_1-C_{10})$heteroaryl, $(C_3-C_7)$cycloalkyl and $(C_1-C_{10})$heterocyclyl.

In another embodiment of the invention, the heterocyclic ring X has the formula $g_1$) (i.e. the heterocyclic ring X of formula g), wherein in the heterocyclic ring X the dashed line is a double bond):

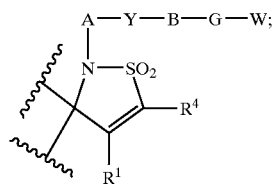

$g_1$)

and wherein each of $R^1$ and $R^4$ is independently selected from the group consisting of hydrogen, $(C_1-C_4)$alkyl, $(C_1-C_4)$alkenyl, $(C_1-C_4)$alkynyl, $(C_6-C_{10})$aryl, $C_1-C_{10}$ heteroaryl, $(C_3-C_7)$cycloalkyl and $(C_1-C_{10})$heterocyclyl.

In another embodiment of the invention, the heterocyclic ring X has the formula h):

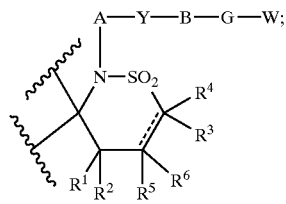

h)

and wherein each of $R^1$, $R^2$, $R^3$, $R^4$, $R^5$, and $R^6$ is independently selected from the group consisting of hydrogen, $(C_1-C_4)$alkyl, $(C_1-C_4)$alkenyl, $(C_1-C_4)$alkynyl, $(C_6-C_{10})$aryl, $(C_1-C_{10})$heteroaryl, $(C_3-C_7)$cycloalkyl and $(C_1-C_{10})$heterocyclyl.

In another embodiment of the invention, the heterocyclic ring X has the formula $h_1$) (i.e. the heterocyclic ring X of formula h), wherein in the heterocyclic ring X the dashed line is a double bond):

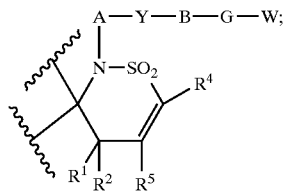

$h_1$)

and wherein each of $R^1$, $R^2$, $R^4$, and $R^5$ is independently selected from the group consisting of hydrogen, $(C_1-C_4)$ alkyl, $(C_1-C_4)$alkenyl, $(C_1-C_4)$alkynyl, $(C_6-C_{10})$aryl, $(C_1-C_{10})$heteroaryl, $(C_3-C_7)$cycloalkyl and $(C_1-C_{10})$heterocyclyl.

In another embodiment of the invention, the heterocyclic ring X has the formula i):

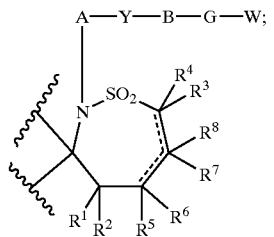

i)

and wherein each of $R^1$, $R^2$, $R^3$, $R^4$, $R^5$, $R^6$, $R^7$, and $R^8$ is independently selected from the group consisting of hydrogen, $(C_1-C_4)$alkyl, $(C_1-C_4)$alkenyl, $(C_1-C_4)$alkynyl, $(C_6-C_{10})$aryl, $(C_1-C_{10})$heteroaryl, $(C_3-C_7)$cycloalkyl and $(C_1-C_{10})$heterocyclyl.

In another embodiment of the invention, the heterocyclic ring X has the formula $i_1$) or $i_2$) (i.e. the heterocyclic ring X of formula i), wherein in the heterocyclic ring X the dashed line is a double bond):

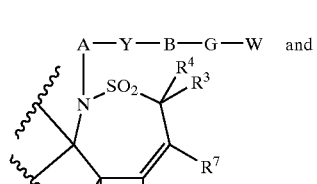

$i_1$)

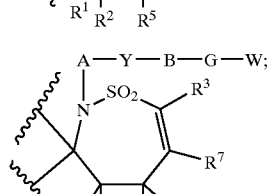

$i_2$)

and wherein each of $R^1$, $R^2$, $R^3$, $R^4$, $R^5$, $R^6$, $R^7$, and $R^8$ is independently selected from the group consisting of hydrogen, $(C_1-C_4)$alkyl, $(C_1-C_4)$alkenyl, $(C_1-C_4)$alkynyl, $(C_6-C_{10})$aryl, $(C_1-C_{10})$heteroaryl, $(C_3-C_7)$cycloalkyl and $(C_1-C_{10})$heterocyclyl.

In a preferred embodiment of the invention, the heterocyclic ring X has the formula j):

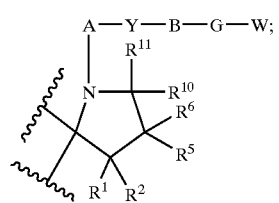

j)

and wherein each of $R^1$, $R^2$, $R^5$, $R^6$, $R^{10}$, and $R^{11}$ is independently selected from the group consisting of hydrogen, $(C_1-C_4)$alkyl, $(C_1-C_4)$alkenyl, $(C_1-C_4)$alkynyl, $(C_6-C_{10})$aryl, $(C_1-C_{10})$heteroaryl, $(C_3-C_7)$cycloalkyl and $(C_1-C_{10})$heterocyclyl.

In another preferred embodiment of the invention, the heterocyclic ring X has the formula k):

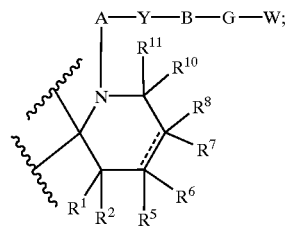

k)

and wherein each of $R^1$, $R^2$, $R^5$, $R^6$, $R^7$, $R^8$, $R^{10}$, and $R^{11}$ is independently selected from the group consisting of hydrogen, $(C_1-C_4)$alkyl, $(C_1-C_4)$alkenyl, $(C_1-C_4)$alkynyl, $(C_6-C_{10})$aryl, $(C_1-C_{10})$heteroaryl, $(C_3-C_7)$cycloalkyl and $(C_1-C_{10})$heterocyclyl.

In another embodiment of the invention, the heterocyclic ring X has the formula $k_1$ (i.e. the heterocyclic ring X of formula k), wherein in the heterocyclic ring X the dashed line is a double bond):

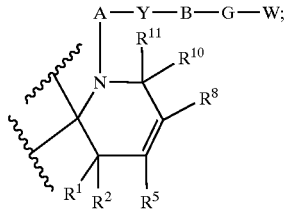

$k_1$)

and wherein each of $R^1$, $R^2$, $R^5$, $R^8$, $R^{10}$, and $R^{11}$ is independently selected from the group consisting of hydrogen, $(C_1-C_4)$alkyl, $(C_1-C_4)$alkenyl, $(C_1-C_4)$alkynyl, $(C_6-C_{10})$aryl, $(C_1-C_{10})$heteroaryl, $(C_3-C_7)$cycloalkyl and $(C_1-C_{10})$heterocyclyl.

In another preferred embodiment of the invention, the heterocyclic ring X has the formula l):

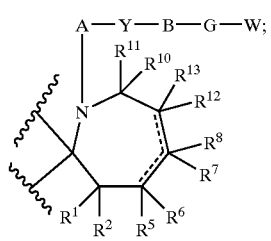

l)

and wherein each of $R^1$, $R^2$, $R^5$, $R^6$, $R^7$, $R^8$, $R^{10}$, $R^{11}$, $R^{12}$ and $R^{13}$ is independently selected from the group consisting of hydrogen, $(C_1-C_4)$alkyl, $(C_1-C_4)$alkenyl, $(C_1-C_4)$alkynyl, $(C_6-C_{10})$aryl, $(C_1-C_{10})$heteroaryl, $(C_3-C_7)$cycloalkyl and $(C_1-C_{10})$heterocyclyl.

In another embodiment of the invention, the heterocyclic ring X has the formula $l_1$) or $l_2$) (i.e. the heterocyclic ring X of formula l), wherein in the heterocyclic ring X the dashed line is a double bond):

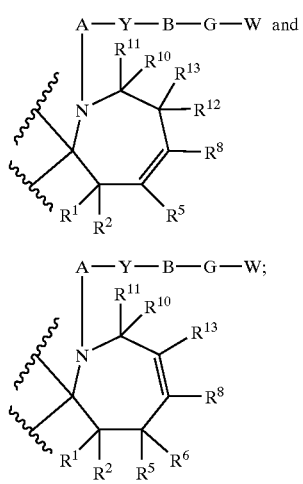

$l_1$)

$l_2$)

and wherein each of $R^1$, $R^2$, $R^5$, $R^6$, $R^7$, $R^8$, $R^{10}$, $R^{11}$, $R^{12}$ and $R^{13}$ is independently selected from the group consisting of hydrogen, $(C_1-C_4)$alkyl, $(C_1-C_4)$alkenyl, $(C_1-C_4)$ alkynyl, $(C_6-C_{10})$aryl, $(C_1-C_{10})$heteroaryl, $(C_3-C_7)$ cycloalkyl and $(C_1-C_{10})$heterocyclyl.

In another embodiment of the invention, the heterocyclic ring X has the formula m):

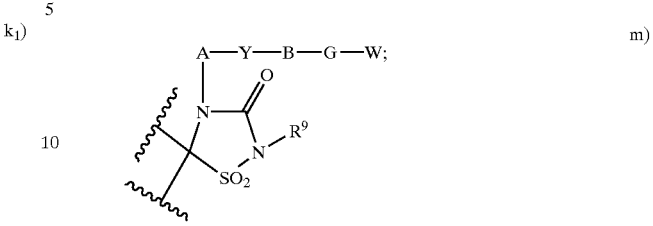

m)

and wherein $R^9$ is selected from hydrogen, $(C_1-C_4)$alkyl, $(C_1-C_4)$alkenyl, $(C_1-C_4)$alkynyl, $(C_6-C_{10})$aryl, $(C_1-C_{10})$heteroaryl, $(C_3-C_7)$cycloalkyl and $(C_1-C_{10})$heterocyclyl.

In another embodiment of the invention, the heterocyclic ring X has the formula n):

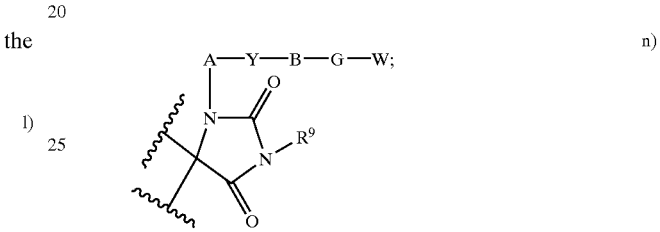

n)

and wherein $R^9$ is selected from hydrogen, $(C_1-C_4)$alkyl, $(C_1-C_4)$alkenyl, $(C_1-C_4)$alkynyl, $(C_6-C_{10})$aryl, $(C_1-C_{10})$heteroaryl, $(C_3-C_7)$cycloalkyl and $(C_1-C_{10})$heterocyclyl.

In another embodiment of the invention, the heterocyclic ring X has the formula o):

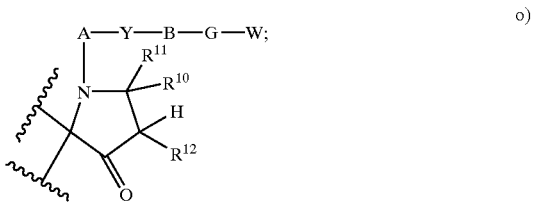

o)

and wherein each of $R^{10}$, $R^{11}$, and $R^{12}$ is independently selected from the group consisting of hydrogen, $(C_1-C_4)$ alkyl, $(C_1-C_4)$alkenyl, $(C_1-C_4)$alkynyl, $(C_6-C_{10})$aryl, $(C_1-C_{10})$heteroaryl, $(C_3-C_7)$cycloalkyl and $(C_1-C_{10})$ heterocyclyl.

In each of the above embodiments of the invention, no more than a total of one of the $R^1$, $R^2$, $R^3$, $R^4$, $R^5$, $R^6$, $R^7$, $R^8$, $R^9$, $R^{10}$, $R^{11}$, $R^{12}$ and $R^{13}$ in any one ring X [i.e., ring a), $a_1$), b), $b_1$), c), $c_1$), $c_2$), d), e), f), g), $g_1$), h), $h_1$), i), $i_1$), $i_2$), j), k), $k_1$), l), $l_1$), $l_2$), m), n), and o)] may be $(C_6-C_{10})$aryl, $(C_1-C_{10})$heteroaryl, $(C_3-C_7)$cycloalkyl and $(C_1-C_{10})$ heterocyclyl.

In another embodiment of each of the above embodiments of the invention, one or two of $R^5$, $R^6$, $R^7$ and $R^8$ is a group other than hydrogen.

In a preferred embodiment of each of the above embodiments of the invention, each of $R^1$, $R^2$, $R^3$, $R^4$, $R^5$, $R^6$, $R^7$, $R^8$, $R^9$, $R^{10}$, $R^{11}$, $R^{12}$ and $R^{13}$ is independently selected from hydrogen and $(C_1-C_4)$alkyl.

In another preferred embodiment of each of the above embodiments of the invention, one or two of $R^1$, $R^2$, $R^3$, $R^4$, $R^{10}$, $R^{11}$, $R^{12}$ and $R^{13}$ is a group other than hydrogen.

In a more preferred embodiment of each of the above embodiments of the invention, each of $R^1$, $R^2$, $R^3$, $R^4$, $R^5$, $R^6$, $R^7$, $R^8$, $R^9$, $R^{10}$, $R^{11}$, $R^{12}$ and $R^{13}$ is hydrogen.

In one embodiment of the invention, W is $(C_1-C_4)$alkoxy $(C_1-C_4)$alkyl, preferably W is methoxymethyl, methoxyethyl, methoxypropyl, methoxybutyl, ethoxymethyl, ethoxyethyl, ethoxypropyl, or ethoxybutyl; more preferably methoxymethyl.

In another embodiment of the invention, W is $(C_3-C_7)$ cycloalkyl, preferably cyclopropyl, cyclobutyl, cyclopentyl, cyclohexyl, or cycloheptyl, optionally substituted on any of the ring carbon atom capable of supporting an additional substituent by one to three substituents per ring independently selected from F, Cl, Br, CN, OH, $(C_1-C_4)$alkyl, $(C_1-C_4)$alkoxy$(C_1-C_4)$alkyl, $(C_1-C_4)$perfluoroalkyl, $(C_1-C_4)$perfluoroalkoxy, $(C_1-C_4)$alkoxy, and $(C_3-C_7)$ cycloalkyloxy, preferably selected from F, Cl, Br, CN, OH, $(C_1-C_4)$alkyl, $(C_1-C_4)$alkoxy$(C_1-C_4)$alkyl, and $(C_1-C_4)$ alkoxy, more preferably selected from F, CN, methyl, ethyl, methoxypropyl, and methoxy; and wherein said W $(C_3-C_7)$ cycloalkyl may optionally be substituted on any ring carbon atoms capable of supporting two additional substituents with one to two oxo groups per ring.

In another embodiment of the invention, W is $(C_6-C_{10})$ aryl, preferably phenyl, optionally substituted on any of the ring carbon atom capable of supporting an additional substituent by one to three substituents per ring independently selected from F, Cl, Br, CN, OH, $(C_1-C_4)$alkyl, $(C_1-C_4)$ alkoxy$(C_1-C_4)$alkyl, $(C_1-C_4)$perfluoroalkyl, $(C_1-C_4)$ perfluoroalkoxy, $(C_1-C_4)$alkoxy, and $(C_3-C_7)$ cycloalkyloxy; preferably selected from F, Cl, CN, $(C_1-C_4)$ alkyl, $(C_1-C_4)$alkoxy$(C_1-C_4)$alkyl, and $(C_1-C_4)$alkoxy; more preferably selected from F, Cl, CN, methyl, ethyl, methoxy, and methoxymethyl.

In another embodiment of the invention, W is unsubstituted phenyl.

In another embodiment of the invention, W is $(C_1-C_{10})$ heteroaryl selected from the group consisting of furyl, imidazolyl, isothiazolyl, isoxazolyl, oxadiazolyl, oxazolyl, pyrazinyl, pyridazinyl, pyridinyl, pyrimidinyl, pyrazolyl, pyrrolyl, tetrazolyl, thiazolyl, thiadiazolyl, thienyl, triazinyl and triazolyl; preferably selected from the group consisting of optionally substituted pyrazinyl, pyridazinyl, pyridinyl, pyrimidinyl, pyrazolyl, isoxazolyl, oxadiazolyl, and oxazolyl; more preferably selected from the group consisting of optionally substituted pyrazinyl, pyridazinyl, pyridinyl, and pyrimidinyl; most preferably selected from the group consisting of pyridinyl and pyrimidinyl; wherein said $(C_1-C_{10})$heteroaryl may be optionally substituted on any of the ring carbon atom capable of supporting an additional substituent by one to three substituents per ring independently selected from F, Cl, Br, CN, OH, $(C_1-C_4)$ alkyl, $(C_1-C_4)$alkoxy$(C_1-C_4)$alkyl, $(C_1-C_4)$perfluoroalkyl, $(C_1-C_4)$perfluoroalkoxy, $(C_1-C_4)$alkoxy, and $(C_3-C_7)$ cycloalkyloxy; preferably selected from F, Cl, CN, $CF_3$, $(C_1-C_4)$alkyl, $(C_1-C_4)$alkoxy$(C_1-C_4)$alkyl, and $(C_1-C_4)$ alkoxy; more preferably selected from F, Cl, CN, $CF_3$, methyl, ethyl, methoxymethyl, and methoxy; and wherein said W $(C_1-C_{10})$heteroaryl may be also optionally substituted on any ring nitrogen atom able to support an additional substituent independently selected from the group consisting of $(C_1-C_4)$alkyl and $(C_1-C_4)$alkyl-(C=O)—.

In another embodiment of the invention, W is $(C_1-C_{10})$ heterocyclyl selected from the group consisting of optionally substituted azetidinyl, hexahydroazepinyl, morpholinyl, piperazinyl, piperidinyl, pyrrolidinyl, thiomorpholinyl, tetrahydrofuranyl, tetrahydropyranyl, and oxetanyl; preferably selected from the group consisting of optionally substituted azetidinyl, morpholinyl, piperazinyl, piperidinyl, pyrrolidinyl, thiomorpholinyl, tetrahydrofuranyl, tetrahydropyranyl, and oxetanyl; more preferably selected from the group consisting of optionally substituted azetidinyl, morpholinyl, piperazinyl, piperidinyl, pyrrolidinyl, tetrahydrofuranyl, and tetrahydropyranyl; wherein said W $(C_1-C_{10})$heterocyclyl may be optionally substituted on any of the ring carbon atom capable of supporting an additional substituent by one to three substituents per ring independently selected from F, Cl, Br, CN, OH, $(C_1-C_4)$alkyl, $(C_1-C_4)$alkoxy$(C_1-C_4)$alkyl, $(C_1-C_4)$ perfluoroalkyl, $(C_1-C_4)$perfluoroalkoxy, $(C_1-C_4)$alkoxy, and $(C_3-C_7)$cycloalkyloxy; preferably selected from F, Cl, $CF_3$, CN, $(C_1-C_4)$alkyl, $(C_1-C_4)$alkoxy$(C_1-C_4)$alkyl, and $(C_1-C_4)$alkoxy; more preferably selected from F, CN, Cl, , methyl, ethyl, and methoxy; wherein said W $(C_1-C_{10})$ heterocyclyl may also optionally be substituted on any ring carbon atom capable of supporting two additional substituents with one to two oxo groups per ring; and wherein said $(C_1-C_{10})$heterocyclyl may also optionally be substituted on any ring nitrogen atom able to support an additional substituent independently selected from the group consisting of $(C_1-C_4)$alkyl and $(C_1-C_4)$alkyl-(C=O)—.

In another embodiment of the invention, W is unsubstituted $(C_1-C_{10})$heterocyclyl.

In each of the above embodiments of the invention, A is $(C_1-C_{10})$heteroaryl selected from the group consisting of benzimidazolyl, benzofuranyl, benzofurazanyl, 2H-1-benzopyranyl, benzothiadiazine, benzothiazinyl, benzothiazolyl, benzothiophenyl, benzoxazolyl, chromanyl, cinnolinyl, furazanyl, furopyridinyl, furyl, imidazolyl, indazolyl, indolinyl, indolizinyl, indolyl, 3H-indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, pyridinyl, pyrimidinyl, pyrazolyl, pyrrolyl, quinazolinyl, quinolinyl, quinoxalinyl, tetrazolyl, thiazolyl, thiadiazolyl, thienyl, triazinyl and triazolyl, wherein said $(C_1-C_{10})$heteroaryl is optionally substituted on any of the ring carbon atom capable of supporting an additional substituent by one or two substituents per ring independently selected from F, Cl, Br, CN, OH, $(C_1-C_4)$alkyl, $(C_1-C_4)$perfluoroalkyl, $(C_1-C_4)$ perfluoroalkoxy, $(C_1-C_4)$alkoxy and $(C_3-C_7)$cycloalkyloxy; preferably A is selected from the group consisting of pyrazinyl, pyridazinyl, pyridinyl, imidazolyl, isothiazolyl, isoxazolyl, oxazolyl, oxadiazolyl, pyrazolyl, and pyrimidinyl; more preferably A is pyrazinyl, pyridazinyl, pyridyl and pyrimidinyl; most preferably A is pyridinyl. Within each of the aforesaid embodiments, Y is selected from the group consisting of a bond, —O—, —S—, —CH$_2$—, >SO$_2$, —OCH$_2$— and —CH$_2$O—; preferably Y is —O—, —OCH$_2$— or —CH$_2$O—; more preferably Y is —O—.

In another embodiment of each of the above embodiments of the invention, A is $(C_6-C_{10})$aryl, such as phenyl or naphthyl, wherein said is $(C_6-C_{10})$aryl is optionally substituted on any of the ring carbon atom capable of supporting an additional substituent by one or two substituents per ring independently selected from F, Cl, Br, CN, OH, $(C_1-C_4)$ alkyl, $(C_1-C_4)$perfluoroalkyl, $(C_1-C_4)$perfluoroalkoxy, $(C_1-C_4)$alkoxy and $(C_3-C_7)$cycloalkyloxy; preferably A is phenyl. Within each of the aforesaid embodiments, Y is selected from the group consisting of a bond, —O—, —S—, —CH$_2$—, >SO$_2$, —OCH$_2$— and —CH$_2$O—; preferably Y is —O—, —OCH$_2$— or —CH$_2$O—; more preferably Y is —O—.

In another embodiment of the invention, B is $(C_6-C_{10})$ aryl, preferably phenyl, optionally substituted on any of the ring carbon atom capable of supporting an additional substituent by one or two substituents per ring independently selected from F, Cl, Br, CN, OH, $(C_1-C_4)$alkyl, $(C_1-C_4)$ perfluoroalkyl, $(C_1-C_4)$perfluoroalkoxy, $(C_1-C_4)$alkoxy and $(C_3-C_7)$cycloalkyloxy.

In another embodiment of the invention, B is $(C_3-C_7)$ cycloalkyl; preferably cyclopentyl or cyclohexyl, optionally substituted on any of the ring carbon atom capable of supporting an additional substituent by one or two substituents per ring independently selected from F, Cl, Br, CN, OH, $(C_1-C_4)$alkyl, $(C_1-C_4)$perfluoroalkyl, $(C_1-C_4)$ perfluoroaikoxy, $(C_1-C_4)$alkoxy and $(C_3-C_7)$cycloalkyloxy.

In another embodiment of the invention, B is $(C_1-C_{10})$ heteroaryl selected from the group consisting of benzimidazolyl, benzofuranyl, benzofurazanyl, 2H-1-benzopyranyl, benzothiadiazine, benzothiazinyl, benzothiazolyl, benzothiophenyl, benzoxazolyl, chromanyl, cinnolinyl, furazanyl, furopyridinyl, furyl, imidazolyl, indazolyl, indolinyl, indolizinyl, indolyl, 3H-indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, pyridinyl, pyrimidinyl, pyrazolyl, pyrrolyl, quinazolinyl, quinolinyl, quinoxalinyl, tetrazolyl, thiazolyl, thiadiazolyl, thienyl, triazinyl and triazolyl; preferably selected from the group consisting of furyl, imidazolyl, isothiazolyl, isoxazolyl, pyrazinyl, pyridazinyl, pyridinyl, pyrimidinyl, pyrazolyl, pyrrolyl, thiazolyl, thiadiazolyl, thienyl, triazinyl and triazolyl; more preferably selected from the group consisting of furyl, imidazolyl, isothiazolyl, isoxazolyl, pyrazinyl, pyridazinyl, pyridinyl, pyrimidinyl, pyrazolyl, pyrrolyl, thiazolyl, thiadiazolyl, thienyl, triazinyl and triazolyl; most preferably selected from the group consisting of pyrazinyl, pyridazinyl, pyridinyl, and pyrimidinyl; wherein said B $(C_1-C_{10})$heteroaryl may be optionally substituted on any of the ring carbon atom capable of supporting an additional substituent by one or two substituents per ring independently selected from F, Cl, Br, CN, OH, $(C_1-C_4)$alkyl, $(C_1-C_4)$ perfluoroalkyl, $(C_1-C_4)$perfluoroalkoxy, $(C_1-C_4)$alkoxy and $(C_3-C_7)$cycloalkyloxy.

In another embodiment of the invention, B is $(C_1-C_{10})$ heterocyclyl optionally substituted on any of the ring carbon atom capable of supporting an additional substituent by one or two substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_7)$ cycloalkyloxy.

In another embodiment of the invention, the group —B—G—W has the formula —B—$[R^{15}$—$(CR^{16}R^{17})_p]$—W.

In another embodiment of the invention, the group —B—G—W has the formula —B—$[(CR^{16}R^{17})_p$—$R^{15}]$—W.

In another embodiment of the invention, the group —B—G—W has the formula —$(C_6-C_{10})$aryl-$[(C_1-C_{10})$ heteroaryl-$(CR^{16}R^{17})_p]$—$(C_6-C_{10})$aryl; wherein p is zero; wherein each of said B $(C_6-C_{10})$aryl and W $(C_6-C_{10})$aryl is optionally substituted on any of the ring carbon atom capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$ perfluoroalkoxy, $(C_1-C_4)$alkoxy, $(C_1-C_4)$alkoxy$(C_1-C_4)$ alkyl, —$NH_2$, —$NO_2$, $(C_1-C_4)$alkyl-NH—, $[(C_1-C_4)$ alkyl$]_2$-N— and $(C_3-C_7)$cycloalkyloxy; and wherein said G $(C_1-C_{10})$heteroaryl is optionally substituted on any of the ring carbon atom capable of supporting an additional substituent by one to three substituents per ring independently selected from F, Cl, Br, CN, OH, $(C_1-C_4)$alkyl, $(C_1-C_4)$ perfluoroalkyl, $(C_1-C_4)$perfluoroalkoxy, $(C_1-C_4)$alkoxy, $(C_1-C_4)$alkoxy$(C_1-C_4)$alkyl, —$NH_2$, $(C_1-C_4)$alkyl-NH—, $[(C_1-C_4)$alkyl$]_2$-N— and $(C_3-C_7)$cycloalkyloxy.

In another embodiment of the invention, both A and B are substituted on any of the ring carbon atom capable of supporting an additional substituent by one or two substituents per ring independently selected from F, Cl, Br, CN, OH, $(C_1-C_4)$alkyl, $(C_1-C_4)$perfluoroalkyl, $(C_1-C_4)$ perfluoroalkoxy, $(C_1-C_4)$alkoxy and $(C_3-C_7)$cycloalkyloxy; preferably selected from the group consisting of F, Cl, CN, methyl, perfluoromethyl, perfluoromethoxy, methoxy, and ethoxy.

In another preferred embodiment of the invention, either A or B is unsubstituted.

In another preferred embodiment of the invention, both A and B are unsubstituted.

In another embodiment of the invention, G is $(C_3-C_7)$ cycloalkyl optionally substituted on any of the ring carbon atom capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy $(C_1-C_4)$alkyl, —$NH_2$, —$NO_2$, $(C_1-C_4)$alkyl-NH—, $[(C_1-C_4)$alkyl$]_2$-N—; $(C_3-C_7)$cycloalkyloxy, —(C=O)— OH, —(C=O)—O—$(C_1-C_4)$alkyl, —(C=O)—$NH_2$, —(C=O)—NH—$(C_1-C_4)$alkyl, and —(C=O)—N $[(C_1-C_4)$alkyl$]_2$; and wherein said $(C_3-C_7)$cycloalkyl may optionally be substituted on any ring carbon atom capable of supporting two additional substituents with one to two oxo groups per ring.

In another embodiment of the invention, G is $(C_6-C_{10})$ aryl optionally substituted on any of the ring carbon atom capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$ perfluoroalkoxy, $(C_1-C_4)$alkoxy, $(C_1-C_4)$alkoxy$(C_1-C_4)$ alkyl, —$NH_2$, —$NO_2$, $(C_1-C_4)$alkyl-NH—, $[(C_1-C_4)$ alkyl$]_2$-N—; $(C_3-C_7)$cycloalkyloxy, —(C=O)—OH, —(C=O)—O—$(C_1-C_4)$alkyl, —(C=O)—$NH_2$, —(C=O)—NH—$(C_1-C_4)$alkyl, and —(C=O)—N $[(C_1-C_4)$alkyl$]_2$; preferably G is phenyl optionally substituted on any of the ring carbon atom capable of supporting an additional substituent by one to three substituents per ring independently selected from F, Cl, CN, $(C_1-C_4)$alkyl, $(C_1-C_4)$alkoxy, $(C_1-C_4)$alkoxy$(C_1-C_4)$alkyl, and $(C_3-C_7)$ cycloalkyloxy; more preferably G is phenyl optionally substituted on any of the ring carbon atom capable of supporting an additional substituent by one substituent per ring independently selected from F, Cl, CN, methyl, ethyl, isopropyl, methoxy, methoxymethyl, methoxyethyl, and cyclopentyloxy. In another embodiment of the invention, G is unsubstituted $(C_6-C_{10})$aryl; preferably G is unsubstituted phenyl.

In another embodiment of the invention, G is $(C_1-C_{10})$ heteroaryl selected from the group consisting of benzimidazolyl, benzofuranyl, benzofurazanyl, 2H-1-benzopyranyl, benzothiadiazine, benzothiazinyl, benzothiazolyl, benzothiophenyl, benzoxazolyl, chromanyl, cinnolinyl, furazanyl, furopyridinyl, furyl, imidazolyl, indazolyl, indolinyl, indolizinyl, indolyl, 3H-indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, pyridinyl, pyrimidinyl, pyrazolyl, pyrrolyl, quinazolinyl, quinolinyl, quinoxalinyl, tetrazolyl, thiazolyl, thiadiazolyl, thienyl, triazinyl and triazolyl; wherein said ($C_1$–$C_{10}$)heteroaryl is optionally substituted on any of the ring carbon atom capable of supporting an additional substituent by one or two substituents per ring independently selected from F, Cl, Br, CN, OH, ($C_1$–$C_4$)alkyl, ($C_1$–$C_4$)perfluoroalkyl, ($C_1$–$C_4$)perfluoroalkoxy, ($C_1$–$C_4$)alkoxy, ($C_1$–$C_4$)alkoxy($C_1$–$C_4$)alkyl, —$NH_2$, —$NO_2$, ($C_1$–$C_4$)alkyl-NH—, [($C_1$–$C_4$)alkyl]$_2$-N—; ($C_3$–$C_7$)cycloalkyloxy, —(C=O)—OH, —(C=O)—O—($C_1$–$C_4$)alkyl, —(C=O)—$NH_2$, —(C=O)—NH—($C_1$–$C_4$)alkyl, and —(C=O)—N[($C_1$–$C_4$)alkyl]$_2$; preferably G is ($C_1$–$C_{10}$)heteroaryl selected from the group consisting of furyl, imidazolyl, isothiazolyl, isoxazolyl, oxadiazolyl, oxazolyl, pyrazinyl, pyridazinyl, pyridinyl, pyrimidinyl, pyrazolyl, pyrrolyl, tetrazolyl, thiazolyl, thiadiazolyl, thienyl, triazinyl and triazolyl; optionally substituted on any of the ring carbon atom capable of supporting an additional substituent by one or two substituents per ring independently selected from F, Cl, CN, ($C_1$–$C_4$)alkyl, ($C_1$–$C_4$)perfluoroalkyl, ($C_1$–$C_4$)perfluoroalkoxy, ($C_1$–$C_4$)alkoxy and ($C_3$–$C_7$)cycloalkyloxy; more preferably G is ($C_1$–$C_{10}$)heteroaryl selected from the group consisting of furyl, imidazolyl, isothiazolyl, isoxazolyl, oxadiazolyl, oxazolyl, pyrazolyl, pyrrolyl, tetrazolyl, thiazolyl, thiadiazolyl, thienyl, and triazolyl optionally substituted on any of the ring carbon atom capable of supporting an additional substituent by one or two substituents per ring independently selected from F, Cl, CN, methyl, ethyl, isopropyl, methoxy, methoxymethyl, methoxyethyl, and cyclopentyloxy; most preferably G is oxazolyl, isoxazolyl, pyrazolyl, or oxadiazolyl optionally substituted on any of the ring carbon atom capable of supporting an additional substituent by one to two substituents per ring independently selected from F, Cl, CN, methyl, ethyl, isopropyl, methoxy, methoxymethyl, methoxyethyl, and cyclopentyloxy.

In another embodiment of the invention, G is oxazol-2-yl or oxazol-5-yl optionally substituted on any of the ring carbon atom capable of supporting an additional substituent by one to two substituents per ring independently selected from F, Cl, CN, methyl, ethyl, isopropyl, methoxy, methoxymethyl, methoxyethyl, and cyclopentyloxy.

In another embodiment of the invention, G is isooxazol-5-yl or isooxazol-3-yl optionally substituted on any of the ring carbon atom capable of supporting an additional substituent by one to two substituents per ring independently selected from F, Cl, CN, methyl, ethyl, isopropyl, methoxy, methoxymethyl, methoxyethyl, and cyclopentyloxy.

In another embodiment of the invention, G is oxadiazol-2-yl, oxadiazol-3-yl, or oxadiazol-5-yl optionally substituted on any of the ring carbon atom capable of supporting an additional substituent by one to two substituents per ring independently selected from F, Cl, CN, methyl, ethyl, isopropyl, methoxy, methoxymethyl, methoxyethyl, and cyclopentyloxy.

In another embodiment of the invention, G is pyrazolyl optionally substituted on any of the ring carbon atom capable of supporting an additional substituent by one to two substituents per ring independently selected from F, Cl, CN, methyl, ethyl, isopropyl, methoxy, methoxymethyl, methoxyethyl, and cyclopentyloxy.

In another embodiment of the invention, G is unsubstituted ($C_1$–$C_{10}$)heteroaryl selected from the group consisting of benzimidazolyl, benzofuranyl, benzofurazanyl, 2H-1-benzopyranyl, benzothiadiazine, benzothiazinyl, benzothiazolyl, benzothiophenyl, benzoxazolyl, chromanyl, cinnolinyl, furazanyl, furopyridinyl, furyl, imidazolyl, indazolyl, indolinyl, indolizinyl, indolyl, 3H-indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, pyridinyl, pyrimidinyl, pyrazolyl, pyrrolyl, quinazolinyl, quinolinyl, quinoxalinyl, tetrazolyl, thiazolyl, thiadiazolyl, thienyl, triazinyl and triazolyl; preferably G is unsubstituted furyl, imidazolyl, isothiazolyl, isoxazolyl, oxadiazolyl, pyrazinyl, pyridazinyl, pyridinyl, pyrimidinyl, pyrazolyl, pyrrolyl, oxazolyl, tetrazolyl, thiazolyl, thiadiazolyl, thienyl, triazinyl and triazolyl; more preferably G is unsubstituted furyl, imidazolyl, isothiazolyl, isoxazolyl, oxadiazolyl, pyrazinyl, pyrazolyl, pyrrolyl, oxazolyl, tetrazolyl, thiazolyl, thiadiazolyl, thienyl, triazinyl and triazolyl; most preferably G is unsubstituted isoxazolyl, oxadiazolyl, pyrazolyl, or oxazolyl.

In another embodiment of the invention, G is ($C_1$–$C_{10}$) heterocyclyl optionally substituted on any of the ring carbon atom capable of supporting an additional substituent by one to three substituents per ring independently selected from F, Cl, Br, CN, OH, ($C_1$–$C_4$)alkyl, ($C_1$–$C_4$)perfluoroalkyl, ($C_1$–$C_4$)perfluoroalkoxy, ($C_1$–$C_4$)alkoxy, ($C_1$–$C_4$)alkoxy($C_1$–$C_4$)alkyl, —$NH_2$, —$NO_2$, ($C_1$–$C_4$)alkyl-NH—, [($C_1$–$C_4$)alkyl]$_2$-N—; ($C_3$–$C_7$)cycloalkyloxy, —(C=O)—OH, —(C=O)—O—($C_1$–$C_4$)alkyl, —(C=O)—$NH_2$, —(C=O)—NH—($C_1$–$C_4$)alkyl, and —(C=O)—N[($C_1$–$C_4$)alkyl]$_2$; and wherein said ($C_1$–$C_{10}$)heterocyclyl may optionally be substituted on any ring carbon atom capable of supporting two additional substituents with one to two oxo groups per ring.

In another embodiment of the invention, G is $R^{15}$—(C$R^{16}R^{17}$)$_p$—; wherein p is an integer from one to four, preferably from one to two; and wherein each of $R^{16}$ or $R^{17}$ is independently hydrogen, methyl, ethyl, propyl, or isopropyl.

In another embodiment of the invention, G is $R^{15}$—(C$R^{16}R^{17}$)$_p$—; wherein p is an integer from one to four, preferably from one to two; and wherein $R^{16}$ and $R^{17}$ are taken together with the carbon to which they are attached to form a 3 to 8-membered carbocyclic ring selected from the group consisting of cyclopropyl, cyclobutyl, cyclopentyl, cyclohexyl, cycloheptyl, cyclooctyl, cyclononyl, cyclopentenyl, and cyclohexenyl.

In another embodiment of the invention, G is ($C_3$–$C_7$)cycloalkyl-(C$R^{16}R^{17}$)$_p$—; wherein p is an integer from one to four, preferably from one to two; wherein said ($C_3$–$C_7$)cycloalkyl is optionally substituted on any of the ring carbon atom capable of supporting an additional substituent by one to three substituents per ring independently selected from F, Cl, Br, CN, OH, ($C_1$–$C_4$)alkyl, ($C_1$–$C_4$)perfluoroalkyl, ($C_1$–$C_4$)perfluoroalkoxy, ($C_1$–$C_4$)alkoxy, ($C_1$–$C_4$)alkoxy($C_1$–$C_4$)alkyl, —$NH_2$, —$NO_2$, ($C_1$–$C_4$)alkyl-NH—, [($C_1$–$C_4$)alkyl]$_2$-N—; ($C_3$–$C_7$)cycloalkoxy —(C=O)—OH, —(C=O)—O—($C_1$–$C_4$)alkyl, —(C=O)—$NH_2$, —(C=O)—NH—($C_1$–$C_4$)alkyl, and —(C=O)—N[($C_1$–$C_4$)alkyl]$_2$; wherein said $R^{15}$ ($C_3$–$C_7$)cycloalkyl may optionally be substituted on any ring carbon atom capable of supporting two additional substituents with one to two oxo groups per ring; and wherein each of $R^{16}$ and $R^{17}$ is independently hydrogen.

In another embodiment of the invention, G is ($C_6$–$C_{10}$) aryl-(C$R^{16}R^{17}$)$_p$—; wherein p is an integer from one to four, preferably from one to two; wherein said ($C_6$–$C_{10}$)aryl is optionally substituted on any of the ring carbon atom capable of supporting an additional substituent by one to three substituents per ring independently selected from F, Cl, Br, CN, OH, ($C_1$–$C_4$)alkyl, ($C_1$–$C_4$)perfluoroalkyl, ($C_1$–$C_4$) perfluoroalkoxy, ($C_1$–$C_4$)alkoxy, ($C_1$–$C_4$)alkoxy($C_1$–$C_4$) alkyl, —$NH_2$, —$NO_2$, ($C_1$–$C_4$)alkyl-NH—, [($C_1$–$C_4$) alkyl]$_2$-N—; ($C_3$–$C_7$)cycloalkyloxy, —(C=O)—OH, —(C=O)—O—($C_1$–$C_4$)alkyl, —(C=O)—$NH_2$, —(C=O)—NH—($C_1$–$C_4$)alkyl, and —(C=O)—N [($C_1$–$C_4$)alkyl]$_2$; and wherein each of $R^{16}$ and $R^{17}$ is independently hydrogen.

In another embodiment of the invention, G is ($C_1$–$C_{10}$) heteroaryl-($CR^{16}R^{17}$)$_p$—; wherein p is an integer from one to four, preferably from one to two; wherein said ($C_1$–$C_{10}$) heteroaryl is selected from the group consisting of benzimidazolyl, benzofuranyl, benzofurazanyl, 2H-1-benzopyranyl, benzothiadiazine, benzothiazinyl, benzothiazolyl, benzothiophenyl, benzoxazolyl, chromanyl, cinnolinyl, furazanyl, furopyridinyl, furyl, imidazolyl, indazolyl, indolinyl, indolizinyl, indolyl, 3H-indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyridazinyl, pyridinyl, pyrimidinyl, pyrazolyl, pyrrolyl, quinazolinyl, quinolinyl, quinoxalinyl, tetrazolyl, thiazolyl, thiadiazolyl, thienyl, triazinyl and triazolyl; preferably selected from the group consisting of optionally substituted imidazolyl, isothiazolyl, isoxazolyl, oxadiazolyl, oxazolyl, pyrazinyl, pyridazinyl, pyridinyl, pyrimidinyl and pyrazolyl; more preferably selected from the group consisting of optionally substituted oxazolyl, isooxazolyl, oxadiazolyl, and pyrazolyl; wherein said ($C_1$–$C_{10}$)heteroaryl is optionally substituted on any of the ring carbon atom capable of supporting an additional substituent by one or two substituents per ring independently selected from F, Cl, Br, CN, OH, ($C_1$–$C_4$)alkyl, ($C_1$–$C_4$) perfluoroalkyl, ($C_1$–$C_4$)perfluoroalkoxy, ($C_1$–$C_4$)alkoxy, ($C_1$–$C_4$)alkoxy($C_1$–$C_4$)alkyl, —$NH_2$, —$NO_2$, ($C_1$–$C_4$)alkyl-NH—, [($C_1$–$C_4$)alkyl]$_2$-N—; ($C_3$–$C_7$)cycloalkyloxy, —(C=O)—OH, —(C=O)—O—($C_1$–$C_4$)alkyl, —(C=O)—$NH_2$, —(C=O)13 NH—($C_1$–$C_4$)alkyl, and —(C=O)—N[($C_1$–$C_4$)alkyl]$_2$; preferably selected from F, Cl, CN, methyl, ethyl, isopropyl, methoxy, methoxymethyl, methoxyethyl, and cyclopentyloxy; and wherein each of $R^{16}$ and $R^{17}$ is independently hydrogen.

In another embodiment of the invention, G is ($C_1$–$C_{10}$) heterocyclyl-($CR^{16}R^{17}$)$_p$—; wherein p is an integer from one to four, preferably from one to two; wherein said ($C_1$–$C_{10}$)heterocyclyl is optionally substituted on any of the ring carbon atom capable of supporting an additional substituent by one to three substituents per ring independently selected from F, Cl, Br, CN, OH, ($C_1$–$C_4$)alkyl, ($C_1$–$C_4$) perfluoroalkyl, ($C_1$–$C_4$)perfluoroalkoxy, ($C_1$–$C_4$)alkoxy, ($C_1$–$C_4$)alkoxy($C_1$–$C_4$)alkyl, —$NH_2$, —$NO_2$, ($C_1$–$C_4$)alkyl-NH—, [($C_1$–$C_4$)alkyl]$_2$-N—; ($C_3$–$C_7$)cycloalkoxy, —(C=O)—OH, —(C=O)—O—($C_1$–$C_4$)alkyl, —(C=O)—$NH_2$, —(C=O)—NH—($C_1$–$C_4$)alkyl, and —(C=O)—N[($C_1$–$C_4$)alkyl]$_2$; and wherein said ($C_1$–$C_{10}$) heterocyclyl may optionally be substituted on any ring carbon atom capable of supporting two additional substituents with one to two oxo groups per ring; and wherein each of $R^{16}$ and $R^{17}$ is independently hydrogen.

In another embodiment of the invention, the heterocyclic ring X has the formula j), k) or l), as defined above; wherein A is ($C_1$–$C_{10}$)heteroaryl selected from the group consisting of pyrazinyl, pyridazinyl, pyridyl and pyrimidinyl; more preferably A is pyridinyl; most preferably A is pyridin-2-yl or pyridin-3-yl; wherein Y is selected from the group consisting of a bond, —O—, —S—, —$CH_2$—, >$SO_2$, —$OCH_2$— and —$CH_2O$—; more preferably Y is —O—, —$OCH_2$— or —$CH_2O$—; most preferably Y is —O—; and wherein W is selected from the group consisting of methoxypropyl, cyclopentyl, cyclohexyl, cycloheptyl, phenyl, pyrazinyl, pyridazinyl, pyridinyl, pyrimidinyl, pyrazolyl, pyrrolyl, morpholinyl, piperazinyl, piperidinyl, pyrrolidinyl, thiomorpholinyl, tetrahydrofuranyl, tetrahydropyranyl, and oxetanyl; preferably selected from the group consisting of phenyl, pyrazinyl, pyridazinyl, pyridinyl, and pyrimidinyl.

In another preferred embodiment of the invention, the heterocyclic ring X has the formula j), k), or l), as defined above; wherein A is ($C_1$–$C_{10}$)heteroaryl selected from the group consisting of pyrazinyl, pyridazinyl, pyridyl and pyrimidinyl; more preferably A is pyridinyl; most preferably A is pyridin-2-yl or pyridin-3-yl; most preferably wherein the pyridinyl together with the X ring and the group —Y—B—G—W has the formulae:

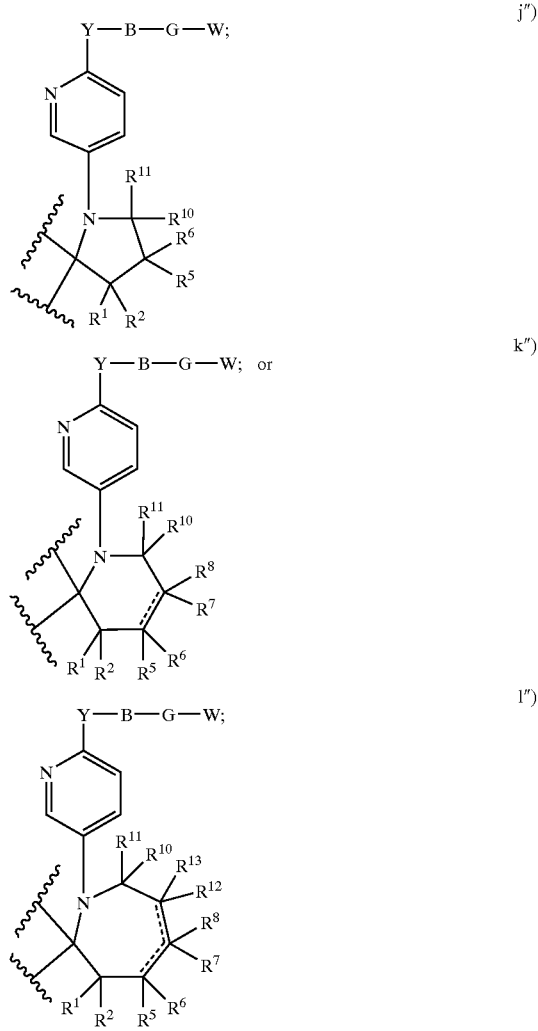

wherein Y is a bond, —O—,—S—, —$CH_2$—, >$SO_2$, —$OCH_2$— or —$CH_2O$—; preferably Y is —O—, —$OCH_2$— or —$CH_2O$—; more preferably Y is —O—; and wherein W is selected from the group consisting of optionally substituted phenyl, pyrazinyl, pyridazinyl, pyridinyl, and pyrimidinyl.

In another preferred embodiment of the invention, the heterocyclic ring X the formula j), k), or l), as defined above;

A is pyridinyl, most preferably wherein the pyridinyl together with the X ring and the group —Y—B—G—W has the formula j"), k") or l") as defined above; Y is —O—; B is phenyl; and wherein G is $(C_1-C_{10})$heteroaryl, preferably oxazolyl, isooxazolyl, oxadiazolyl, or pyrazolyl, optionally substituted on any of the ring carbon atom capable of supporting an additional substituent by one to three substituents per ring selected from the group consisting of F, Cl, Br, CN, OH, methoxy, cyclopentyloxy and cyclohexyloxy.

In a most preferred embodiment of the invention, the heterocyclic ring X the formula j), k), or l), as defined above; A is pyridinyl, most preferably wherein the pyridinyl together with the X ring and the group —Y—B—G—W has the formula j"), k") or l"), as defined above; Y is —O—; B is unsubstituted phenyl; G is $R^{15}$—$(CR^{16}R^{17})_p$—; wherein p is zero; and $R^{15}$ is $(C_1-C_{10})$heteroaryl, preferably oxazolyl, isooxazolyl, oxadiazolyl, and pyrazolyl, optionally substituted on any of the ring carbon atom capable of supporting an additional substituent by one to three substituents per ring selected from the group consisting of F, Cl, CN, and methoxy.

Compounds of the invention are selected from the group consisting of:

3-(2-{4-[5-(6,8,10-Trioxo-1,7,9-triaza-spiro[4.5]dec-1-yl)-pyridin-2-yloxy]-phenyl}-oxazol-4-yl)-benzonitrile;

1-(6-{4-[4-(2-Fluoro-phenyl)-oxazol-2-yl]-phenoxy}-pyridin-3-yl)-1,7,9-triaza-spiro[4.5]decane-6,8,10-trione;

1-(6-{4-[4-(3-Fluoro-phenyl)-oxazol-2-yl]-phenoxy}-pyridin-3-yl)-1,7,9-triaza-spiro[4.5]decane-6,8,10-trione;

1-(6-{4-[4-(4-Fluoro-phenyl)-oxazol-2-yl]-phenoxy}-pyridin-3-yl)-1,7,9-triaza-spiro[4.5]decane-6,8,10-trione;

1-(6-{4-[3-(4-Fluoro-phenyl)-[1,2,4]oxadiazol-5-yl]-phenoxy}-pyridin-3-yl)-1,7,9-triaza-spiro[4.5]decane-6,8,10-trione;

1-(6-{4-[5-(4-Fluoro-phenyl)-oxazol-2-yl]-phenoxy}-pyridin-3-yl)-1,7,9-triaza-spiro[4.5]decane-6,8,10-trione;

1-(6-{4-[5-(4-Fluoro-phenyl)-[1,3,4]oxadiazol-2-yl]-phenoxy}-pyridin-3-yl)-1,7,9-triaza-spiro[4.5]decane-6,8,10-trione;

1-(6-{4-[2-(4-Fluoro-phenyl)-oxazol-5-yl]-phenoxy}-pyridin-3-yl)-1,7,9-triaza-spiro[4.5]decane-6,8,10-trione;

1-(6-{4-[2-(4-Fluoro-phenyl)-oxazol-4-yl]-phenoxy}-pyridin-3-yl)-1,7,9-triaza-spiro[4.5]decane-6,8,10-trione;

1-(6-4-[4-(4-Fluoro-phenyl)-4,5-dihydro-oxazol-2-yl]-phenoxyl-pyridin-3-yl)-1,7,9-triaza-spiro[4.5]decane-6,8,10-trione;

1-(6-{4-[1-(4-Fluoro-phenyl)-1H-pyrazol-3-yl]-phenoxy}-pyridin-3-yl)-1,7,9-triaza-spiro[4.5]decane-6,8,10-trione;

1-(6-{4-[5-(4-Fluoro-phenyl)-2H-pyrazol-3-yl]-phenoxy}-pyridin-3-yl)-1,7,9-triaza-spiro[4.5]decane-6,8,10-trione;

1-(6-{4-[5-(4-Fluoro-phenyl)-[1,2,4]oxadiazol-3-yl]-phenoxy}-pyridin-3-yl)-1,7,9-triaza-spiro[4.5]decane-6,8,10-trione;

1-(6-{4-[5-(4-Fluoro-phenyl)-isoxazol-3-yl]-phenoxy}-pyridin-3-yl)-1,7,9-triaza-spiro[4.5]decane-6,8,10-trione;

1-(6-{4-[3-(4-Fluoro-phenyl)-isoxazol-5-yl]-phenoxy}-pyridin-3-yl)-1,7,9-triaza-spiro[4.5]decane-6,8,10-trione;

1-{6-[4-(4-Pyridin-3-yl-oxazol-2-yl)-phenoxy]-pyridin-3-yl}-1,7,9-triaza-spiro[4.5]decane-6,8,10-trione;

1-{6-[4-(3-Pyridin-3-yl-[1,2,4]oxadiazol-5-yl)-phenoxy]-pyridin-3-yl}-1,7,9-triaza-spiro[4.5]decane-6,8,10-trione;

1-{6-[4-(5-Pyridin-3-yl-oxazol-2-yl)-phenoxy]-pyridin-3-yl}-1,7,9-triaza-spiro[4.5]decane-6,8,10-trione;

1-{6-[4-(5-Pyridin-3-yl-[1,3,4]oxadiazol-2-yl)-phenoxy]-pyridin-3-yl}-1,7,9-triaza-spiro[4.5]decane-6,8,10-trione;

1-{6-[4-(2-Pyridin-3-yl-oxazol-5-yl)-phenoxy]-pyridin-3-yl}-1,7,9-triaza-spiro[4.5]decane-6,8,10-trione;

1-{6-[4-(2-Pyridin-3-yl-oxazol-4-yl)-phenoxy]-pyridin-3-yl}-1,7,9-triaza-spiro[4.5]decane-6,8,10-trione;

1-{6-[4-(4-Pyridin-3-yl-4,5-dihydro-oxazol-2-yl)-phenoxy]-pyridin-3-yl}-1,7,9-triaza-spiro[4.5]decane-6,8,10-trione;

1-{6-[4-(1-Pyridin-3-yl-1H-pyrazol-3-yl)-phenoxy]-pyridin-3-yl}-1,7,9-triaza-spiro[4.5]decane-6,8,10-trione;

1-{6-[4-(5-Pyridin-3-yl-2H-pyrazol-3-yl)-phenoxy]-pyridin-3-yl}-1,7,9-triaza-spiro[4.5]decane-6,8,10-trione;

1-{6-[4-(5-Pyridin-3-yl-[1,2,4]oxadiazol-3-yl)-phenoxy]-pyridin-3-yl}-1,7,9-triaza-spiro[4.5]decane-6,8,10-trione;

1-{6-[4-(5-Pyridin-3-yl-isoxazol-3-yl)-phenoxy]-pyridin-3-yl}-1,7,9-triaza-spiro[4.5]decane-6,8,10-trione;

1-{6-[4-(3-Pyridin-3-yl-isoxazol-5-yl)-phenoxy]-pyridin-3-yl}-1,7,9-triaza-spiro[4.5]decane-6,8,10-trione;

1-{6-[4-(4-Pyridin-4-yl-oxazol-2-yl)-phenoxy]-pyridin-3-yl}-1,7,9-triaza-spiro[4.5]decane-6,8,10-trione;

1-{6-[4-(3-Pyridin-4-yl-[1,2,4]oxadiazol-5-yl)-phenoxy]-pyridin-3-yl}-1,7,9-triaza-spiro[4.5]decane-6,8,10-trione;

1-{6-[4-(5-Pyridin-4-yl-oxazol-2-yl)-phenoxy]-pyridin-3-yl}-1,7,9-triaza-spiro[4.5]decane-6,8,10-trione;

1-{6-[4-(5-Pyridin-4-yl-[1,3,4]oxadiazol-2-yl)-phenoxy]-pyridin-3-yl}-1,7,9-triaza-spiro[4.5]decane-6,8,10-trione;

1-{6-[4-(2-Pyridin-4-yl-oxazol-5-yl)-phenoxy]-pyridin-3-yl}-1,7,9-triaza-spiro[4.5]decane-6,8,10-trione;

1-{6-[4-(2-Pyridin-4-yl-oxazol-4-yl)-phenoxy]-pyridin-3-yl}-1,7,9-triaza-spiro[4.5]decane-6,8,10-trione;

1-{6-[4-(4-Pyridin-4-yl-4,5-dihydro-oxazol-2-yl)-phenoxy]-pyridin-3-yl}-1,7,9-triaza-spiro[4.5]decane-6,8,10-trione;

1-{6-[4-(1-Pyridin-4-yl-1H-pyrazol-3-yl)-phenoxy]-pyridin-3-yl}-1,7,9-triaza-spiro[4.5]decane-6,8,10-trione;

1-{6-[4-(5-Pyridin-4-yl-2H-pyrazol-3-yl)-phenoxy]-pyridin-3-yl}-1,7,9-triaza-spiro[4.5]decane-6,8,10-trione;

1-{6-[4-(5-Pyridin-4-yl-[1,2,4]oxadiazol-3-yl)-phenoxy]-pyridin-3-yl}-1,7,9-triaza-spiro[4.5]decane-6,8,10-trione;

1-{6-[4-(5-Pyridin-4-yl-isoxazol-3-yl)-phenoxy]-pyridin-3-yl}-1,7,9-triaza-spiro[4.5]decane-6,8,10-trione;

1-{6-[4-(3-Pyridin-4-yl-isoxazol-5-yl)-phenoxy]-pyridin-3-yl}-1,7,9-triaza-spiro[4.5]decane-6,8,10-trione;

6-(2-{4-[5-(6,8,10-Trioxo-1,7,9-triaza-spiro[4.5]dec-1-yl)-pyridin-2-yloxy]-phenyl}-oxazol-4-yl)-nicotinonitrile;

6-(5-{4-[5-(6,8,10-Trioxo-1,7,9-triaza-spiro[4.5]dec-1-yl)-pyridin-2-yloxy]-phenyl}-[1,2,4]oxadiazol-3-yl)-nicotinonitrile;

6-(2-{4-[5-(6,8,10-Trioxo-1,7,9-triaza-spiro[4.5]dec-1-yl)-pyridin-2-yloxy]-phenyl}-oxazol-5-yl)-nicotinonitrile;

6-(5-{4-[5-(6,8,10-Trioxo-1,7,9-triaza-spiro[4.5]dec-1-yl)-pyridin-2-yloxy]-phenyl}-[1,3,4]oxadiazol-2-yl)-nicotinonitrile;

6-(5-{4-[5-(6,8,10-Trioxo-1,7,9-triaza-spiro[4.5]dec-1-yl)-pyridin-2-yloxy]-phenyl}-oxazol-2-yl)-nicotinonitrile;

6-(4-{4-[5-(6,8,10-Trioxo-1,7,9-triaza-spiro[4.5]dec-1-yl)-pyridin-2-yloxy]-phenyl}-oxazol-2-yl)-nicotinonitrile;

6-(2-{4-[5-(6,8,10-Trioxo-1,7,9-triaza-spiro[4.5]dec-1-yl)-pyridin-2-yloxy]-phenyl}-4,5-dihydro-oxazol-4-yl)-nicotinonitrile;

6-(3-{4-[5-(6,8,10-Trioxo-1,7,9-triaza-spiro[4.5]dec-1-yl)-pyridin-2-yloxy]-phenyl}-pyrazol-1-yl)-nicotinonitrile;

6-(5-{4-[5-(6,8,10-Trioxo-1,7,9-triaza-spiro[4.5]dec-1-yl)-pyridin-2-yloxy]-phenyl}-1H-pyrazol-3-yl)-nicotinonitrile;

6-(3-{4-[5-(6,8,10-Trioxo-1,7,9-triaza-spiro[4.5]dec-1-yl)-pyridin-2-yloxy]-phenyl}-[1,2,4]oxadiazol-5-yl)-nicotinonitrile;

6-(3-{4-[5-(6,8,10-Trioxo-1,7,9-triaza-spiro[4.5]dec-1-yl)-pyridin-2-yloxy]-phenyl}-isoxazol-5-yl)-nicotinonitrile;

6-(5-{4-[5-(6,8,10-Trioxo-1,7,9-triaza-spiro[4. 5]dec-1-yl)-pyridin-2-yloxy]-phenyl}-isoxazol-3-yl)-nicotinonitrile;

1-{6-[4-(4-p-Tolyl-oxazol-2-yl)-phenoxy]-pyridin-3-yl}-1,7,9-triaza-spiro[4.5]decane-6,8,10-trione;

1-{6-[4-(3-p-Tolyl-[1,2,4]oxadiazol-5-yl)-phenoxy]-pyridin-3-yl}-1,7,9-triaza-spiro[4.5]decane-6,8,10-trione;

1-{6-[4-(5-p-Tolyl-oxazol-2-yl)-phenoxy]-pyridin-3-yl}-1,7,9-triaza-spiro[4.5]decane-6,8,10-trione;

1-{6-[4-(5-p-Tolyl-[1,3,4]oxadiazol-2-yl)-phenoxy]-pyridin-3-yl}-1,7,9-triaza-spiro[4.5]decane-6,8,10-trione;

1-{6-[4-(2-p-Tolyl-oxazol-5-yl)-phenoxy]-pyridin-3-yl}-1,7,9-triaza-spiro[4.5]decane-6,8,10-trione;

1-{6-[4-(2-p-Tolyl-oxazol-4-yl)-phenoxy]-pyridin-3-yl}-1,7,9-triaza-spiro[4.5]decane-6,8,10-trione;

1-{6-[4-(4-p-Tolyl-4,5-dihydro-oxazol-2-yl)-phenoxy]-pyridin-3-yl}-1,7,9-triaza-spiro[4.5]decane-6,8,10-trione;

1-{6-[4-(1-p-Tolyl-1H-pyrazol-3-yl)-phenoxy]-pyridin-3-yl}-1,7,9-triaza-spiro[4.5]decane-6,8,10-trione;

1-{6-[4-(5-p-Tolyl-2H-pyrazol-3-yl)-phenoxy]-pyridin-3-yl}-1,7,9-triaza-spiro[4.5]decane-6,8,10-trione;

1-{6-[4-(5-p-Tolyl-[1,2,4]oxadiazol-3-yl)-phenoxy]-pyridin-3-yl}-1,7,9-triaza-spiro[4.5]decane-6,8,10-trione;

1-{6-[4-(5-p-Tolyl-isoxazol-3-yl)-phenoxy]-pyridin-3-yl}-1,7,9-triaza-spiro[4.5]decane-6,8,10-trione;

1-{6-[4-(3-p-Tolyl-isoxazol-5-yl)-phenoxy]-pyridin-3-yl}-1,7,9-triaza-spiro[4.5]decane-6,8,10-trione;

1-(6-{4-[4-(4-Chloro-phenyl)-oxazol-2-yl]-phenoxy}-pyridin-3-yl)-1,7,9-triaza-spiro[4.5]decane-6,8,10-trione;

1-(6-{4-[3-(4-Chloro-phenyl)-[1,2,4]oxadiazol-5-yl]-phenoxy}-pyridin-3-yl)-1,7,9-triaza-spiro[4.5]decane-6,8,10-trione;

1-(6-{4-[5-(4-Chloro-phenyl)-oxazol-2-yl]-phenoxy}-pyridin-3-yl)-1,7,9-triaza-spiro[4.5]decane-6,8,10-trione;

1-(6-{4-[5-(4-Chloro-phenyl)-[1,3,4]oxadiazol-2-yl]-phenoxy}-pyridin-3-yl)-1,7,9-triaza-spiro[4.5]decane-6,8,10-trione;

1-(6-{4-[2-(4-Chloro-phenyl)-oxazol-5-yl]-phenoxy}-pyridin-3-yl)-1,7,9-triaza-spiro[4.5]decane-6,8,10-trione;

1-(6-{4-[2-(4-Chloro-phenyl)-oxazol-4-yl]-phenoxy}-pyridin-3-yl)-1,7,9-triaza-spiro[4.5]decane-6,8,10-trione;

1-(6-{4-[4-(4-Chloro-phenyl)-4,5-dihydro-oxazol-2-yl]-phenoxy}-pyridin-3-yl-1,7,9-triaza-spiro[4.5]decane-6,8,10-trione;

1-(6-{4-[1-(4-Chloro-phenyl)-1H-pyrazol-3-yl]-phenoxy}-pyridin-3-yl)-1,7,9-triaza-spiro[4.5]decane-6,8,10-trione;

1-(6-{4-[5-(4-Chloro-phenyl)-2H-pyrazol-3-yl]-phenoxy}-pyridin-3-yl)-1,7,9-triaza-spiro[4.5]decane-6,8,10-trione;

1-(6-{4-[5-(4-Chloro-phenyl)-[1,2,4]oxadiazol-3-yl]-phenoxy}-pyridin-3-yl)-1,7,9-triaza-spiro[4.5]decane-6,8,10-trione;

1-(6-{4-[5-(4-Chloro-phenyl)-isoxazol-3-yl]-phenoxy}-pyridin-3-yl)-1,7,9-triaza-spiro[4.5]decane-6,8,10-trione;

1-(6-{4-[3-(4-Chloro-phenyl)-isoxazol-5-yl]-phenoxy}-pyridin-3-yl)-1,7,9-triaza-spiro[4.5]decane-6,8,10-trione;

1-(6-{4-[4-(4-Methoxy-phenyl)-oxazol-2-yl]-phenoxy}-pyridin-3-yl)-1,7,9-triaza-spiro[4.5]decane-6,8,10-trione;

1-(6-{4-[3-(4-Methoxy-phenyl)-[1,2,4]oxadiazol-5-yl]-phenoxy}-pyridin-3-yl)-1,7,9,-triaza-spiro[4.5]decane-6,8,10-trione;

1-(6-{4-[5-(4-Methoxy-phenyl)-oxazol-2-yl]-phenoxy}-pyridin-3-yl)-1,7,9-triaza-spiro[4.5]decane-6,8,10-trione;

1-(6-{4-[5-(4-Methoxy-phenyl)-[1,3,4]oxadiazol-2-yl]-phenoxy}-pyridin-3-yl)-1,7,9-triaza-spiro[4.5]decane-6,8,10-trione;

1-(6-{4-[2-(4-Methoxy-phenyl)-oxazol-5-yl]-phenoxy}-pyridin-3-yl)-1,7,9-triaza-spiro[4.5]decane-6,8,10-trione;

1-(6-{4-[2-(4-Methoxy-phenyl)-oxazol-4-yl]-phenoxy}-pyridin-3-yl)-1,7,9-triaza-spiro[4.5]decane-6,8,10-trione;

1-(6-{4-[4-(4-Methoxy-phenyl)-4,5-dihydro-oxazol-2-yl]-phenoxy}-pyridin-3-yl)-1,7,9-triaza-spiro[4.5]decane-6,8,10-trione;

1-(6-{4-[1-(4-Methoxy-phenyl)-1H-pyrazol-3-yl]-phenoxy}-pyridin-3-yl)-1,7,9-triaza-spiro[4.5]decane-6,8,10-trione;

1-(6-{4-[5-(4-Methoxy-phenyl)-2H-pyrazol-3-yl]-phenoxy}-pyridin-3-yl)-1,7,9-triaza-spiro[4.5]decane-6,8,10-trione;

1-(6-{4-[5-(4-Methoxy-phenyl)-[1,2,4]oxadiazol-3-yl]-phenoxy}-pyridin-3-yl)-1,7,9-triaza-spiro[4.5]decane-6,8,10-trione;

1-(6-{4-[5-(4-Methoxy-phenyl)-isoxazol-3-yl]-phenoxy}-pyridin-3-yl)-1,7,9-triaza-spiro[4.5]decane-6,8,10-trione;

1-(6-{4-[3-(4-Methoxy-phenyl)-isoxazol-5-yl]-phenoxy}-pyridin-3-yl)-1,7,9-triaza-spiro[4.5]decane-6,8,10-trione;

4-(2-{4-[5-(6,8,10-Trioxo-1,7,9-triaza-spiro[4.5]dec-1-yl)-pyridin-2-yloxy]-phenyl}-oxazol-4-yl)-benzonitrile;

4-(5-{4-[5-(6,8,10-Trioxo-1,7,9-triaza-spiro[4.5]dec-1-yl)-pyridin-2-yloxy]-phenyl}-[1,2,4]oxadiazol-3-yl)-benzonitrile;

4-(2-{4-[5-(6,8,10-Trioxo-1,7,9-triaza-spiro[4.5]dec-1-yl)-pyridin-2-yloxy]-phenyl}-oxazol-5-yl)-benzonitrile;

4-(5-{4-[5-(6,8,10-Trioxo-1,7,9-triaza-spiro[4.5]dec-1-yl)-pyridin-2-yloxy]-phenyl}-[1,3,4]oxadiazol-2-yl)-benzonitrile;

4-(5-{4-[5-(6,8,10-Trioxo-1,7,9-triaza-spiro[4.5]dec-1-yl)-pyridin-2-yloxy]-phenyl}-oxazol-2-yl)-benzonitrile;

4-(4-{4-[5-(6,8,10-Trioxo-1,7,9-triaza-spiro[4.5]dec-1-yl)-pyridin-2-yloxy]-phenyl}-oxazol-2-yl)-benzonitrile;

4-(2-{4-[5-(6,8,10-Trioxo-1,7,9-triaza-spiro[4.5]dec-1-yl)-pyridin-2-yloxy]-phenyl}-4,5-dihydro-oxazol-4-yl)-benzonitrile;

4-(3-{4-[5-(6,8,10-Trioxo-1,7,9-triaza-spiro[4.5]dec-1-yl)-pyridin-2-yloxy]-phenyl-pyrazol-1-yl)-benzonitrile;

4-(5-{4-[5-(6,8,10-Trioxo-1,7,9-triaza-spiro[4.5]dec-1-yl)-pyridin-2-yloxy]-phenyl}-1H-pyrazol-3-yl)-benzonitrile;

4-(3-{4-[5-(6,8,10-Trioxo-1,7,9-triaza-spiro[4.5]dec-1-yl)-pyridin-2-yloxy]-phenyl}-[1,2,4]oxadiazol-5-yl)-benzonitrile;

4-(3-{4-[5-(6,8,10-Trioxo-1,7,9-triaza-spiro[4.5]dec-1-yl)-pyridin-2-yloxy]-phenyl}-isoxazol-5-yl)-benzonitrile;

4-(5-{4-[5-(6,8,10-Trioxo-1,7,9-triaza-spiro[4.5]dec-1-yl)-pyridin-2-yloxy]-phenyl}-isoxazol-3-yl)-benzonitrile;

1-{6-[4-(4-Pyridin-2-yl-oxazol-2-yl)-phenoxy]-pyridin-3-yl}-1,7,9-triaza-spiro[4.5]decane-6,8,10-trione;

1-{6-[4-(3-Pyridin-2-yl-[1,2,4]oxadiazol-5-yl)-phenoxy]-pyridin-3-yl}-1,7,9-triaza-spiro[4.5]decane-6,8,10-trione;

1-{6-[4-(5-Pyridin-2-yl-oxazol-2-yl)-phenoxy]-pyridin-3-yl}-1,7,9-triaza-spiro[4.5]decane-6,8,10-trione;

1-{6-[4-(5-Pyridin-2-yl-[1,3,4]oxadiazol-2-yl)-phenoxy]-pyridin-3-yl}-1,7,9-triaza-spiro[4.5]decane-6,8,10-trione;

1-{6-[4-(2-Pyridin-2-yl-oxazol-5-yl)-phenoxy]-pyridin-3-yl}-1,7,9-triaza-spiro[4.5]decane-6,8,10-trione;

1-{6-[4-(2-Pyridin-2-yl-oxazol-4-yl)-phenoxy]-pyridin-3-yl}-1,7,9-triaza-spiro[4.5]decane-6,8,10-trione;

1-{6-[4-(4-Pyridin-2-yl-4,5-dihydro-oxazol-2-yl)-phenoxy]-pyridin-3-yl}-1,7,9-triaza-spiro[4.5]decane-6,8,10-trione;

1-{6-[4-(1-Pyridin-2-yl-1H-pyrazol-3-yl)-phenoxy]-pyridin-3-yl}-1,7,9-triaza-spiro[4.5]decane-6,8,10-trione;

1-{6-[4-(5-Pyridin-2-yl-2H-pyrazol-3-yl)-phenoxy]-pyridin-3-yl}-1,7,9-triaza-spiro[4.5]decane-6,8,10-trione;
1-{6-[4-(5-Pyridin-2-yl-[1,2,4]oxadiazol-3-yl)-phenoxy]-pyridin-3-yl}-1,7,9-triaza-spiro[4.5]decane-6,8,10-trione;
1-{6-[4-(5-Pyridin-2-yl-isoxazol-3-yl)-phenoxy]-pyridin-3-yl}-1,7,9-triaza-spiro[4.5]decane-6,8,10-trione;
1-{6-[4-(3-Pyridin-2-yl-isoxazol-5-yl)-phenoxy]-pyridin-3-yl}-1,7,9-triaza-spiro[4.5]decane-6,8,10-trione;
1-{6-[4-(4-Pyridazin-3-yl-oxazol-2-yl)-phenoxy]-pyridin-3-yl}-1,7,9-triaza-spiro[4.5]decane-6,8,10-trione;
1-{6-[4-(3-Pyridazin-3-yl-[1,2,4]oxadiazol-5-yl)-phenoxy]-pyridin-3-yl}-1,7,9-triaza-spiro[4.5]decane-6,8,10-trione;
1-{6-[4-(5-Pyridazin-3-yl-oxazol-2-yl)-phenoxy]-pyridin-3-yl}-1,7,9-triaza-spiro[4.5]decane-6,8,10-trione;
1-{6-[4-(5-Pyridazin-3-yl-[1,3,4]oxadiazol-2-yl)-phenoxy]-pyridin-3-yl}-1,7,9-triaza-spiro[4.5]decane-6,8,10-trione;
1-{6-[4-(2-Pyridazin-3-yl-oxazol-5-yl)-phenoxy]-pyridin-3-yl}-1,7,9-triaza-spiro[4.5]decane-6,8,10-trione;
1-{6-[4-(2-Pyridazin-3-yl-oxazol-4-yl)-phenoxy]-pyridin-3-yl}-1,7,9-triaza-spiro[4.5]decane-6,8,10-trione;
1-{6-[4-(4-Pyridazin-3-yl-4,5-dihydro-oxazol-2-yl)-phenoxy]-pyridin-3-yl}-1,7,9-triaza-spiro[4.5]decane-6,8,10-trione;
1-{6-[4-(1-Pyridazin-3-yl-1H-pyrazol-3-yl)-phenoxy]-pyridin-3-yl}-1,7,9-triaza-spiro[4.5]decane-6,8,10-trione;
1-{6-[4-(5-Pyridazin-3-yl-2H-pyrazol-3-yl)-phenoxy]-pyridin-3-yl}-1,7,9-triaza-spiro[4.5]decane-6,8,10-trione;
1-{6-[4-(5-Pyridazin-3-yl-[1,2,4]oxadiazol-3-yl)-phenoxy]-pyridin-3-yl}-1,7,9-triaza-spiro[4.5]decane-6,8,10-trione;
1-{6-[4-(5-Pyridazin-3-yl-isoxazol-3-yl)-phenoxy]-pyridin-3-yl}-1,7,9-triaza-spiro[4.5]decane-6,8,10-trione;
1-{6-[4-(3-Pyridazin-3-yl-isoxazol-5-yl)-phenoxy]-pyridin-3-yl}-1,7,9-triaza-spiro[4.5]decane-6,8,10-trione;
1-(6-{4-[4-(3-Methoxy-propyl)-oxazol-2-yl]-phenoxy}-pyridin-3-yl)-1,7,9-triaza-spiro[4.5]decane-6,8,10-trione;
1-(6-{4-[3-(3-Methoxy-propyl)-[1,2,4]oxadiazol-5-yl]-phenoxy}-pyridin-3-yl)-1,7,9-triaza-spiro[4.5]decane-6,8,10-trione;
1-(6-{4-[5-(3-Methoxy-propyl)-oxazol-2-yl]-phenoxy}-pyridin-3-yl)-1,7,9-triaza-spiro[4.5]decane-6,8,10-trione;
1-(6-{4-[5-(3-Methoxy-propyl)-[1,3,4]oxadiazol-2-yl]-phenoxy}-pyridin-3-yl)-1,7,9-triaza-spiro[4.5]decane-6,8,10-trione;
1-(6-{4-[2-(3-Methoxy-propyl)-oxazol-5-yl]-phenoxy}-pyridin-3-yl)-1,7,9-triaza-spiro[4.5]decane-6,8,10-trione;
1-(6-{4-[2-(3-Methoxy-propyl)-oxazol-4-yl]-phenoxy}-pyridin-3-yl)-1,7,9-triaza-spiro[4.5]decane-6,8,10-trione;
1-(6-{4-[4-(3-Methoxy-propyl)-4,5-dihydro-oxazol-2-yl]-phenoxy1-pyridin-3-yl}-1,7,9-triaza-spiro[4.5]decane-6,8,10-trione;
1-(6-{4-[1-(3-Methoxy-propyl)-1H-pyrazol-3-yl]-phenoxy}-pyridin-3-yl)-1,7,9-triaza-spiro[4.5]decane-6,8,10-trione;
1-(6-{4-[5-(3-Methoxy-propyl)-2H-pyrazol-3-yl]-phenoxy}-pyridin-3-yl)-1,7,9-triaza-spiro[4.5]decane-6,8,10-trione;
1-(6-{4-[5-(3-Methoxy-propyl)-[1,2,4]oxadiazol-3-yl]-phenoxy}-pyridin-3-yl)-1,7,9-triaza-spiro[4.5]decane-6,8,10-trione;
1-(6-{4-[5-(3-Methoxy-propyl)-isoxazol-3-yl]-phenoxy}-pyridin-3-yl)-1,7,9-triaza-spiro[4.5]decane-6,8,10-trione; and
1-(6-{4-[3-(3-Methoxy-propyl)-isoxazol-5-yl]-phenoxy}-pyridin-3-yl)-1,7,9-triaza-spiro[4.5]decane-6,8,10-trione; or
the pharmaceutically acceptable salts thereof.

Other compounds of the invention are selected from the group consisting of:
1-{6-[4-(3-o-Tolyl-[1,2,4]oxadiazol-5-yl)-phenoxy]-pyridin-3-yl}-1,7,9-triaza-spiro[4.5]decane-6,8,10-trione;
1-{6-[4-(3-m-Tolyl-[1,2,4]oxadiazol-5-yl)-phenoxy]-pyridin-3-yl}-1,7,9-triaza-spiro[4.5]decane-6,8,10-trione;
1-(6-{4-[3-(2-Chloro-phenyl)-[1,2,4]oxadiazol-5-yl]-phenoxy}-pyridin-3-yl)-1,7,9-triaza-spiro[4.5]decane-6,8,10-trione;
1-(6-{4-[3-(3-Fluoro-phenyl)-[1,2,4]oxadiazol-5-yl]-phenoxy}-pyridin-3-yl)-1,7,9-triaza-spiro[4.5]decane-6,8,10-trione;
1-(6-{4-[3-(3-phenyl)-[1,2,4]oxadiazol-5-yl]-phenoxy}-pyridin-3-yl)-1,7,9-triaza-spiro[4.5]decane-6,8,10-trione;
1-{6-[4-(5-Phenyl-[1,3,4]oxadiazol-2-yl)-phenoxy]-pyridin-3-yl}-1,7,9-triaza-spiro[4.5]decane-6,8,10-trione;
1-{6-[4-(4-Phenyl-4,5-dihydro-oxazol-2-yl)-phenoxy]-pyridin-3-yl}-1,7,9-triaza-spiro[4.5]decane-6,8,10-trione;
1-{6-[4-(4-Phenyl-oxazol-2-yl)-phenoxy]-pyridin-3-yl}-1,7,9-triaza-spiro[4.5]decane-6,8,10-trione;
1-{6-[4-(5-Phenyl-[1,2,4]oxadiazol-3-yl)-phenoxy]-pyridin-3-yl}-1,7,9-triaza-spiro[4.5]decane-6,8,10-trione;
1-{6-[4-(5-Phenyl-oxazol-2-yl)-phenoxy]-pyridin-3-yl}-1,7,9-triaza-spiro[4.5]decane-6,8,10-trione; and
1-{6-[4-(4-(4-fluorophenyl)-oxazol-2-yl)-phenoxy]-pyridin-3-yl}-1,7,9-triaza-spiro[4.5]decane-6,8,10-trione; or
the pharmaceutically acceptable salts thereof.

Other compounds of the invention are selected from the group consisting of:
1-(6-{4-[4-(4-Fluoro-phenyl)-oxazol-2-yl]-phenoxy}-pyridin-3-yl)-1,8,10-triaza-spiro[5.5]undecane-7,9,11-trione;
4-(2-{4-[5-(7,9,11-Trioxo-1,8,10-triaza-spiro[5.5]undec-1-yl)-pyridin-2-yloxy]-phenyl}-oxazol-4-yl)-benzonitrile;
1-(6-{4-[4-(4-Fluoro-phenyl)-oxazol-2-yl]-phenoxy}-pyridin-3-yl)-1,7,9-triaza-spiro[4.5]decane-2,6,8,10-tetraone;
4-(2-{4-[5-(2,6,8,10-Tetraoxo-1,7,9-triaza-spiro[4.5]dec-1-yl)-pyridin-2-yloxy]-phenyl}-oxazol-4-yl)-benzonitrile;
1-(6-{4-[4-(4-Fluoro-phenyl)-oxazol-2-yl]-phenoxy}-pyridin-3-yl)-3-methyl-1,3,7,9-tetraaza-spiro[4.5]decane-2,6,8,10-tetraone;
4-(2-{4-[5-(3-Methyl-2,6,8,10-tetraoxo-1,3,7,9-tetraaza-spiro[4.5]dec-1-yl)-pyridin-2-yloxy]-phenyl}-oxazol-4-yl)-benzonitrile;
1-(6-{4-[4-(4-Fluoro-phenyl)-oxazol-2-yl]-phenoxy}-pyridin-3-yl)-2,2-dioxo-2l6-thia-1,7,9-triaza-spiro[4.5]decane-6,8,10-trione;
4-(2-{4-[5-(2,2,6,8,10-Pentaoxo-2l6-thia-1,7,9-triaza-spiro[4.5]dec-1-yl)-pyridin-2-yloxy]-phenyl}-oxazol-4-yl)-benzonitrile;
1-(6-{4-[4-(4-Fluoro-phenyl)-oxazol-2-yl]-phenoxy}-pyridin-3-yl)-3-methyl-1,3,7,9-tetraaza-spiro[4.5]decane-2,4,6,8,10-pentaone
4-(2-{4-[5-(3-Methyl-2,4,6,8,10-pentaoxo-1,3,7,9-tetraaza-spiro[4.5]dec-1-yl)-pyridin-2-yloxy]-phenyl}-oxazol-4-yl)-benzonitrile;
4-(6-{4-[4-(4-Fluoro-phenyl)-oxazol-2-yl]-phenoxy}-pyridin-3-yl)-2-methyl-1l6-thia-2,4,7,9-tetraaza-spiro[4.5]decane-3,6,8,10-tetraone;
4-(2-{4-[5-(2-Methyl-1,1,3,6,8,10-hexaoxo-1l6-thia-2,4,7,9-tetraaza-spiro[4.5]dec-4-yl)-pyridin-2-yloxy]-phenyl}-oxazol-4-yl)-benzonitrile;
1-(6-{4-[4-(4-Fluoro-phenyl)-oxazol-2-yl]-phenoxy}-pyridin-3-yl)-1,7,9-triaza-spiro[4.5]decane-4,6,8,10-tetraone;

4-(2-{4-[5-(4,6,8,10-Tetraoxo-1,7,9-triaza-spiro[4.5]dec-1-yl)-pyridin-2-yloxy]-phenyl}-oxazol-4-yl)-benzonitrile;

7-(6-{4-[4-(4-Fluoro-phenyl)-oxazol-2-yl]-phenoxy}-pyridin-3-yl)-2,4,7-triaza-spiro[5.6]dodecane-1,3,5-trione; and 4-(2-{4-[5-(1,3, 5-Trioxo-2,4,7-triaza-spiro[5.6]dodec-7-yl)-pyridin-2-yloxy]-phenyl}-oxazol-4-yl)-benzonitrile; or the pharmaceutically acceptable salts thereof.

Preferred compounds of the invention are selected from the group consisting of:

1-(6-{4-[4-(4-Fluoro-phenyl)-oxazol-2-yl]-phenoxy}-pyridin-3-yl)-1,7,9-triaza-spiro[4.5]decane-6,8,10-trione;

4-(2-{4-[5-(6,8,10-Trioxo-1,7,9-triaza-spiro[4.5]dec-1-yl)-pyridin-2-yloxy]-phenyl}-oxazol-4-yl)-benzonitrile;

3-(2-{4-[5-(6,8,10-Trioxo-1,7,9-triaza-spiro[4.5]dec-1-yl)-pyridin-2-yloxy]-phenyl}-oxazol-4-yl)-benzonitrile;

1-(6-{4-[4-(2-Fluoro-phenyl)-oxazol-2-yl]-phenoxy}-pyridin-3-yl)-1,7,9-triaza-spiro[4.5]decane-6,8,10-trione; and 1-(6-{4-[4-(3-Fluoro-phenyl)-oxazol-2-yl]-phenoxy}-pyridin-3-yl)-1,7,9-triaza-spiro[4.5]decane-6,8,10-trione; or the pharmaceutically acceptable salts thereof.

The present invention also relates to a pharmaceutical composition for the treatment of a condition selected from the group consisting of connective tissue disorders, inflammatory disorders, immunology/allergy disorders, infectious diseases, respiratory diseases, cardiovascular diseases, eye diseases, metabolic diseases, central nervous system (CNS) disorders, liver/kidney diseases, reproductive health disorders, gastric disorders, skin disorders and cancers and other diseases characterized by metalloproteinase activity in a mammal, including a human, comprising an amount of a compound of formula I or a pharmaceutically acceptable salt thereof effective in such treatments and a pharmaceutically acceptable carrier.

The present invention also relates to a pharmaceutical composition for the treatment of a condition which can be treated by the inhibition of matrix metalloproteinases in a mammal, including a human, comprising an amount of a compound of formula I effective in such treatment and a pharmaceutically acceptable carrier.

The present invention also relates to a method for the inhibition of matrix metalloproteinases in a mammal, including a human, comprising administering to said mammal an effective amount of a compound of formula I.

The present invention also relates to a method for treating a condition selected from the group consisting of connective tissue disorders, inflammatory disorders, immunology/allergy disorders, infectious diseases, respiratory diseases, cardiovascular diseases, eye diseases, metabolic diseases, central nervous system (CNS) disorders, liver/kidney diseases, reproductive health disorders, gastric disorders, skin disorders and cancers and other diseases characterized by matrix metalloproteinase activity in a mammal, including a human, comprising administering to said mammal an amount of a compound of formula I or a pharmaceutically acceptable salt thereof effective in treating such a condition.

The present invention also relates to a method for the inhibition of matrix metalloproteinases or other metalloproteinases involved in matrix degradation, in a mammal, including a human, comprising administering to said mammal an effective amount of a compound of formula I or a pharmaceutically acceptable salt thereof.

The present inventors have also discovered that it is possible to identify inhibitors of formula I with differential metalloprotease activity (preferably MMP-13 inhibitory activity). One group of preferred inhibitors of formula I the inventors have been able to identify include those which selectively inhibit MMP-13 preferentially over MMP-1. The compounds of the invention also possess selectivity over a related group of enzymes known as reprolysins, such as TACE and aggrecanase. Another group of preferred inhibitors of formula I the inventors have been able to identify include those which selectively inhibit MMP-13 preferentially over MMP-1 and MMP-14. Another group of preferred inhibitors of formula I the inventors have been able to identify include those which selectively inhibit MMP-13 preferentially over MMP-1 and 12. Another group of preferred inhibitors of formula I the inventors have been able to identify include those which selectively inhibit MMP-13 preferentially over MMP-1, 12 and 14. Another group of preferred inhibitors of formula I the inventors have been able to identify include those which selectively inhibit MMP-13 preferentially over MMP-1, 2, 3, 7, 9 and 14. Most preferred compounds of the invention selectively inhibit MMP-13 preferentially over any two or more of MMP-1, 2, 3, 7, 9, 12 and 14 and mammalian reprolysins.

The present invention also relates to a method for treating a medical condition of the type that is characterized by the destruction of articular cartilage in a mammalian subject, which method comprises administering to the subject having said condition a therapeutically effective amount of a suitably substituted pyrimidine-2,4,6-trione, wherein said suitably substituted pyrimidine-2,4,6-trione exhibits: i) a ratio of MMP-1 $IC_{50}$/MMP-13 $IC_{50}$ of about 50, and ii) a ratio of MMP-14 $IC_{50}$/MMP-13 $IC_{50}$ of about 50; wherein said MMP-1 $IC_{50}$ is measured by a recombinant MMP-1 assay; wherein each of said MMP-13 $IC_{50}$ is measured by a recombinant MMP-13 assay; and wherein said MMP-14 $IC_{50}$ is measured by a recombinant MMP-14 assay.

The present invention also relates to a method for treating a medical condition of the type that is characterized by the destruction of articular cartilage in a mammalian subject, which method comprises administering to the subject having said condition a therapeutically effective amount of a suitably substituted pyrimidine-2,4,6-trione, wherein said suitably substituted pyrimidine-2,4,6-trione additionally exhibits iii) a ratio of MMP-12 $IC_{50}$/MMP-13 $IC_{50}$ of about 50; wherein said MMP-12 $IC_{50}$ is measured by a recombinant MMP-12 assay; and wherein said MMP-13 $IC_{50}$ is measured by a recombinant MMP-13 assay.

The present invention also relates to a method for treating a medical condition of the type that is characterized by the destruction of articular cartilage in a mammalian subject, which method comprises administering to the subject having said condition a therapeutically effective amount of a suitably substituted pyrimidine-2,4,6-trione, wherein said suitably substituted pyrimidine-2,4,6-trione additionally exhibits iv) a ratio of MMP-2 $IC_{50}$/MMP-13 $IC_{50}$ of about 50, and v) a ratio of MMP-3 $IC_{50}$/MMP-13 $IC_{50}$ of about 50; vi) a ratio of MMP-7 $IC_{50}$/MMP-13 $IC_{50}$ of about 50, and vii) a ratio of MMP-9 $IC_{50}$/MMP-13 $IC_{50}$ of about 50; wherein said MMP-2 $IC_{50}$ is measured by a recombinant MMP-2 assay; wherein said MMP-3 $IC_{50}$ is measured by a recombinant MMP-3 assay; wherein said MMP-7 $IC_{50}$ is measured by a recombinant MMP-7 assay; wherein said MMP-9 $IC_{50}$ is measured by a recombinant MMP-9 assay; and each of said MMP-13 $IC_{50}$ is measured by a recombinant MMP-13 assay.

The present invention also relates to a method for treating a medical condition of the type that is characterized by the destruction of articular cartilage in a mammalian subject, which method comprises administering to the subject having said condition a therapeutically effective amount of a suitably substituted pyrimidine-2,4,6-trione, wherein said suitably substituted pyrimidine-2,4,6-trione exhibits an MMP-13 IC$_{50}$ of less than about 100 nM, preferably of less than about 50 nM; more preferably of less than about 20 nM.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

"Connective tissue disorders" as used herein refers to disorders such as degenerative cartilage loss following traumatic joint injury, osteoarthritis, osteoporosis, Paget's disease, loosening of artificial joint implants, periodontal disease and gingivitis.

"Destruction of articular cartilage" as used herein refers to connective tissue disorders resulting in articular cartilage destruction, preferably joint injury, reactive arthritis, acute pyrophosphate arthritis (pseudogout), psoriatic arthritis, or juvenile rheumatoid arthritis, more preferably osteoarthritis.

"Inflammatory disorders" as used herein refers to disorders such as rheumatoid arthritis, ankylosing spondylitis, psoriatic arthritis, psoriasis, chondrocalcinosis, gout, inflammatory bowel disease, ulcerative colitis, Crohn's disease, fibromyalgia, and cachexia.

"Immunology/allergy disorders" as used herein refers to disorders such as organ transplant toxicity, allergic reactions, allergic contact hypersensitivity, autoimmune disorders such as those disorders associated with granulomatous inflammation/tissue remodeling (such as asthma), immunosuppression and sarcoid.

"Infectious diseases," including those mediated by viruses, bacteria, fungi or mycobacterial infection, as used herein refers to disorders such as septic arthritis, AIDS, fever; Prion diseases, myasthenia gravis, Malaria, sepsis, hemodynamic shock and septic shock.

"Respiratory diseases" as used herein refers to disorders such as chronic obstructive pulmonary disease (including emphysema), acute respiratory distress syndrome, asthma, hyperoxic alveolar injury and idiopathic pulmonary fibrosis and other fibrotic lung diseases.

"Cardiovascular diseases" as used herein refers to disorders such as atherosclerosis including atherosclerotic plaque rupture; aortic aneurysm including abdominal aortic aneurysm and brain aortic aneurysm; congestive heart failure; myocardial and cerebral infarction; stroke; cerebral ischemia; coagulation and acute phase response; left ventricular dilation; post ischemic reperfusion injury; angiofibromas; hemangiomas; and restenosis.

"Eye diseases" as used herein refers to disorders such as aberrant angiogenesis, ocular angiogenesis, ocular inflammation, keratoconus, Sjogren's syndrome, myopia, ocular tumors, corneal graft rejection, corneal injury, neovascular glaucoma, corneal ulceration, corneal scarring, macular degeneration (including "Age Related Macular Degeneration (ARMD) including both wet and dry forms), proliferative vitreoretinopathy and retinopathy of prematurity.

"Metabolic diseases" as used herein refers to disorders such as diabetes (including non-insulin dependent diabetes mellitus, diabetic retinopathy, insulin resistance, diabetic ulceration).

"Central Nervous System" (CNS) disorders as used herein refers to disorders such as head trauma, spinal cord injury, Inflammatory diseases of the central nervous system, neurodegenerative disorders (acute and chronic), Alzheimer's disease, demyelinating diseases of the nervous system, Huntington's disease, Parkinson's disease, peripheral neuropathy, pain, cerebral amyloid angiopathy, nootropic or cognition enhancement, amyotrophic lateral sclerosis, multiple sclerosis, migraine, depression and anorexia.

"Liver/Kidney diseases" as used herein refers to disorders such as nephrotic syndromes such as glomerulonephritis and glomerular disease of the kidney, proteinuria, cirrhosis of the liver and interstitial nephritis.

"Reproductive Health disorders" as used herein refers to disorders such as endometriosis, contraception (male/female), dysmenorrhea, dysfunctional uterine bleeding, premature rupture of fetal membranes and abortifactant.

"Gastric disorders" as used herein refers to disorders such as colonic anastomosis and gastric ulcers.

"Skin disorders" as used herein refers to disorders such as skin aging, pressure sores, psoriasis, eczema, dermatitis, radiation damage, tissue ulceration, decubital ulcers, epidermolysis bullosa, abnormal wound healing (topical and oral formulations), burns and scleritis.

"Cancers" as used herein refers to disorders such as solid tumor cancer including colon cancer, breast cancer, lung cancer and prostrate cancer, tumor invasion, tumor growth tumor metastasis, cancers of the oral cavity and pharynx (lip, tongue, mouth, pharynx), esophagus, stomach, small intestine, large intestine, rectum, liver and biliary passages, pancreas, larynx, lung, bone, connective tissue, skin, cervix uteri, corpus endometrium, ovary, testis, bladder, kidney and other urinary tissues, eye brain and central nervous system, thyroid and other endocrine gland, Hodgkin's disease, non-Hodgkin's lymphomas, multiple myeloma and hematopoietic malignancies including leukemias and lymphomas including lymphocytic, granulocytic and monocytic.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, —O—, phosphorous, fluorine and chlorine, such as $^{2}H$, $^{3}H$, $^{13}C$, $^{14}C$, $^{15}N$ $^{18}O$, $^{17}O$, $^{31}P$, $^{32}P$, $^{35}S$, $^{18}F$ and $^{36}Cl$, respectively. Compounds of the present invention, prodrugs thereof and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically-labelled compounds of Formula I of this invention and prodrugs thereof can generally be prepared by carrying out the procedures disclosed in the Schemes and/or in the Examples and Preparations below, by substituting a readily available isotopically-labelled reagent for a non-isotopically-labelled reagent.

This invention also encompasses pharmaceutical compositions containing prodrugs of compounds of the formula I. This invention also encompasses methods of treating or preventing disorders that can be treated or prevented by the inhibition of matrix metalloproteinases or the inhibition of mammalian reprolysin comprising administering prodrugs of compounds of the formula I. Compounds of formula I having free amino, amido, hydroxy, sulfonamide or carboxylic groups can be converted into prodrugs. Prodrugs include compounds wherein an amino acid residue, or a polypeptide chain of two or more (e.g., two, three or four) amino acid residues which are covalently joined through peptide bonds to free amido, amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters, which are covalently, bonded to the above substituents of formula I through the carbonyl carbon prodrug sidechain. Prodrugs also include dimers of compounds of formula I.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonal antibodies (such as infliximab, D2E7 and CDP-870) and TNF receptor immunoglobulin molecules (such as etanercept), ICE inhibitors, MEKK1 inhibitors, COX-2 inhibitors such as celecoxib, rofecoxib, valdecoxib and etoricoxib; low dose methotrexate, lefunimide, steroids, glucosamines, chondrosamines/sulfates, gabapentin, A-agonists, IL-1 process and release inhibitors, IL-1 receptor antagonists such as Kineret®, CCR-1 antagonists, hydroxychloroquine, d-penicilamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, paracoxib, etoricoxib and rofecoxib, analgesics, steroids, glucosamines, chondrosamines/sulfates, gabapentin, A-agonists, IL-1 process and release inhibitors, CCR-1 antagonists, LTD-4, LTB-4 and 5-LO inhibitors, p38 kinase inhibitors and intraarticular therapies such as corticosteroids and hyaluronic acids such as hyalgan and synvisc.

The compounds of the present invention may also be used in combination with anticancer agents such as endostatin and angiostatin or cytotoxic drugs such as adriamycin, daunomycin, cis-platinum, etoposide, paclitaxel, docetaxel and alkaloids, such as vincristine and antimetabolites such as methotrexate.

The compounds of the present invention may also be used in combination with cardiovascular agents such as calcium channel blockers (such as amlodipine and nifedipine), lipid lowering agents such as statins (such as lovastatin, atorvastatin, pravastatin and simvastatin), adrenergics such as doxazosin and terazosin; fibrates, beta-blockers, Ace inhibitors (such as captopril, lisinopril, fosinopril, enalapril and quinaprill), Angiotensin-2 receptor antagonists such as losartan and irbesartan; nitrates, CCB's, diuretics such as digitalis and platelet aggregation inhibitors. The compounds of the present invention may also be used in combination with plaque rupture preventitive agents such as statins, zithromax, NSAIDs including aspirin, heparin, urarfarin, abciximab, TPA and platelet Inhibitors. The compounds of the present invention may also be used in combination with stroke treatment agents such as NIF, NHEI's and CCRIR antagonists.

The compounds of the present invention may also be used in combination with CNS agents such as antidepressants (such as sertraline), anti-Parkinsonian drugs (such as deprenyl, carbadopa, L-dopa, dopamine receptor agonists such as ropinirole, pergolide and pramripexble; MAOB inhibitors such as selegiline and rasagiline, catechol-O-methyltrasferase inhibitors such as tolcapone, A-2 inhibitors, dopamine reuptake inhibitors, NMDA antagonists, Nicotine agonists, NK-1 inhibitors, dopamine agonists and inhibitors of neuronal nitric oxide synthase) and anti-Alzheimer's drugs such as donepezil, tacrine, COX-2 inhibitors, propentofylline or metryfonate.

The compounds of the present invention may also be used in combination with osteoporosis agents such as roloxifene, droloxifene, lasofoxifene or fosomax and immunosuppressant agents such as FK-506 and rapamycin.

The compounds of the present invention may also be used in combination with agents for the treatment of respiratory diseases such as PDE-IV inhibitors, steroidals such as fluticasone, triamcinolone, budesonide, budesonide and beclomethasone, anticholinergics such as ipratropium, sympathomimetics such as salmeterol, albuterol and Xopenex, decongestants such as fexofenadine, loratadine and cetirizine; leukotriene antagonists such as zafirlukast and motelukast; and mast cell stabilizers such as zileuton.

The compounds of the present invention may also be used in combination with agents for the treatment of skin disorders such as tretinoin, isotretinoin, steroids such as cortisone and mometasone, antibiotics such as tetracycline, antifungals such as clotrimazole, miconazole and fluconazole and PDE-IV inhibitors.

The compounds of the present invention may also be used in combination with agents for the treatment of diabetes such as insulin, including human or humanized insulin and inhaled insulin, aldose reductase inhibitors, sorbitol dehydrogenase inhibitors, antidiabetic agents such as biguanides such as metformin; glitazones, glycosidase inhibitors such as acarbose, sulfonylureas such as glimepiride and glipizide; and thiazolidinediones such as pioglitazone, rosiglitazone and trogliazone. Preferred combinations are useful for treating the side effects of diabetes such as retinopathy, nephropathy and neuropathy, preferably retinopathy.

DETAILED DESCRIPTION OF THE INVENTION

The following reaction Schemes illustrate the preparation of the compounds of the present invention. Unless otherwise indicated each of A, Y, B, G, W, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}$ in the reaction Schemes and the discussion that follows is defined as above.

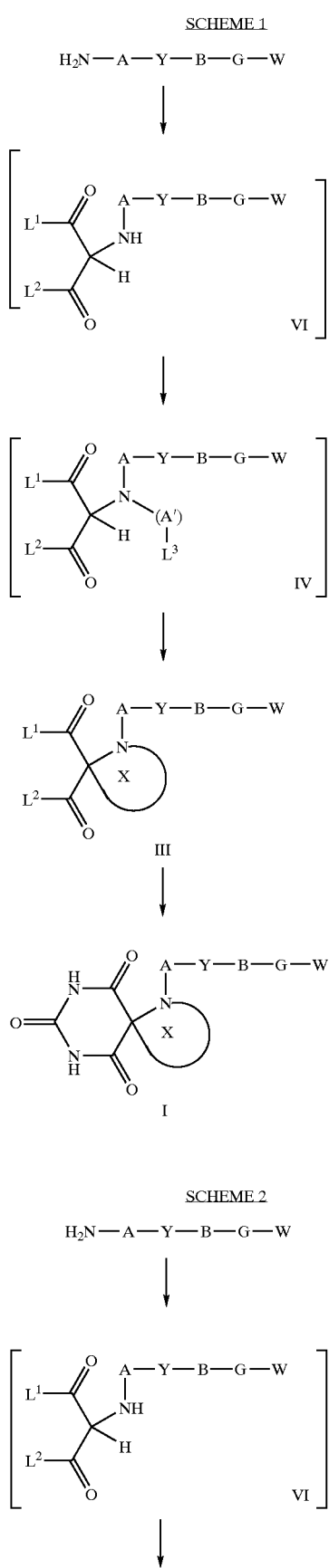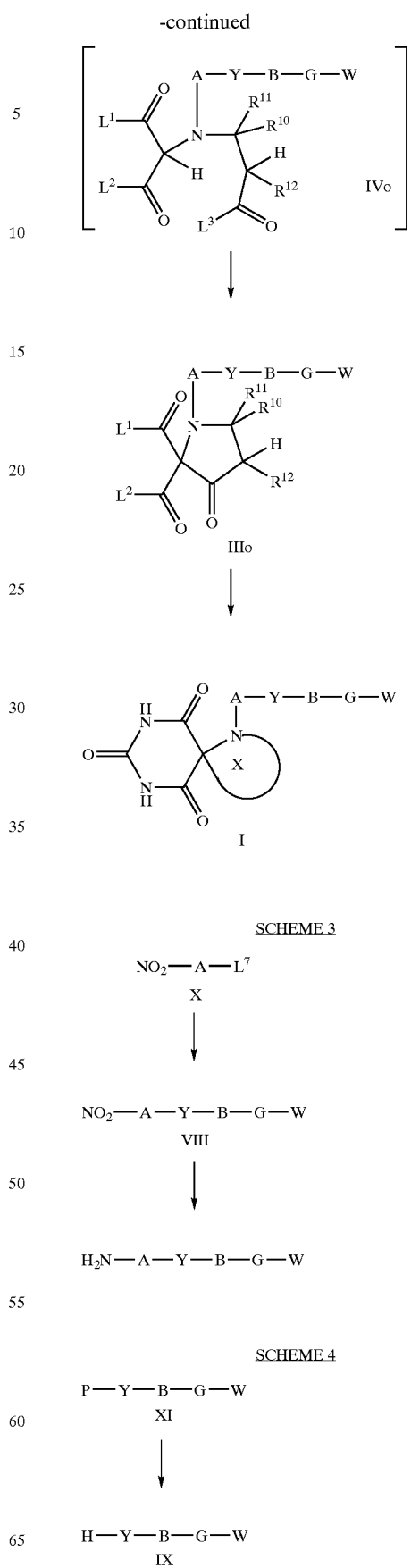

SCHEME 5
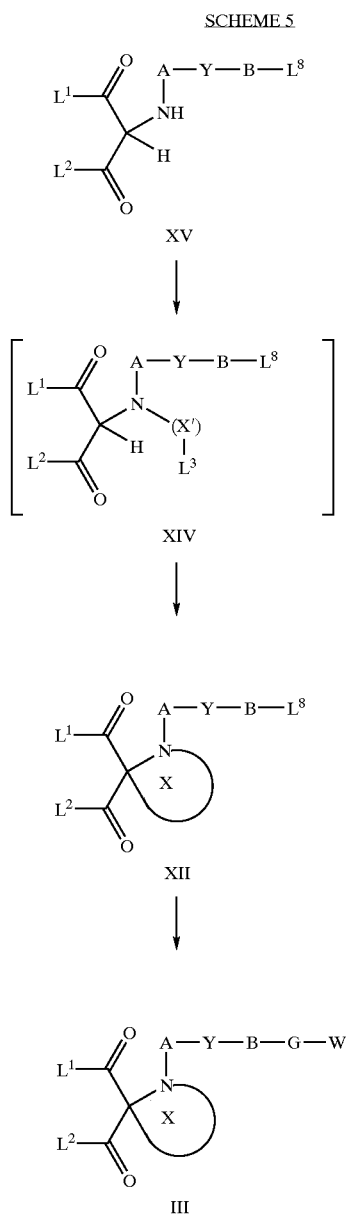
SCHEME 6
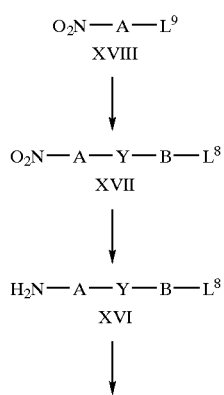
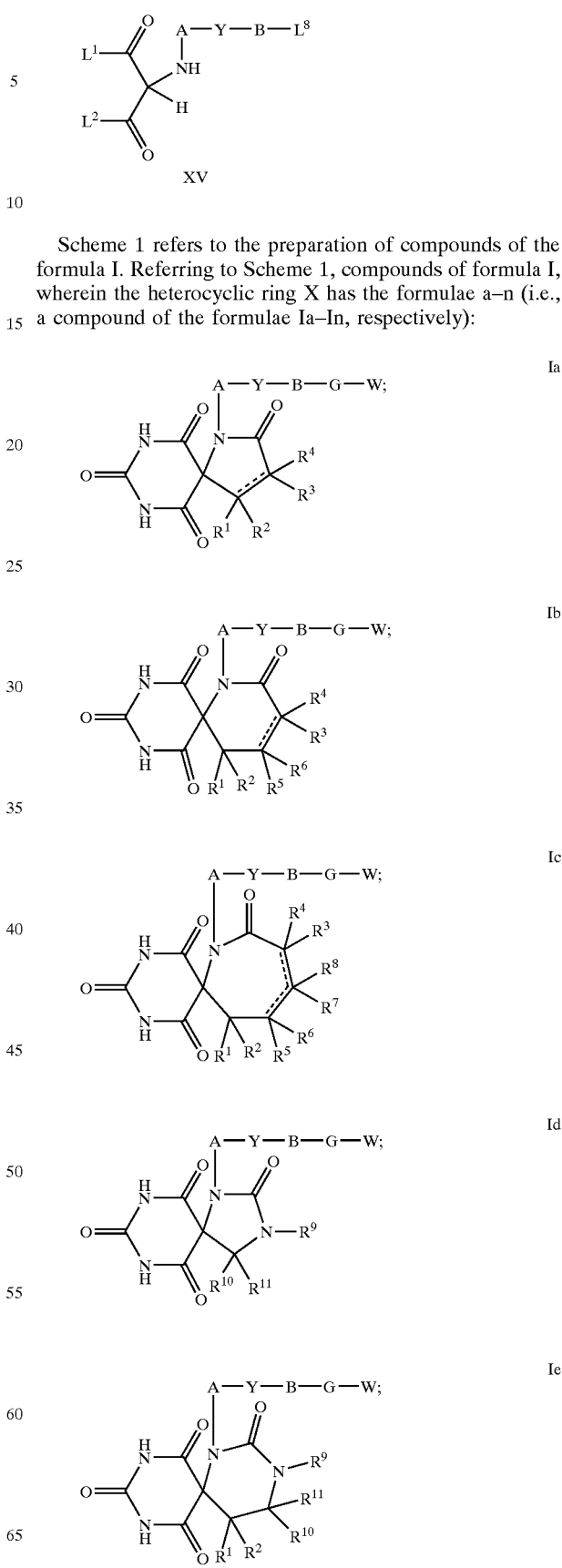
Scheme 1 refers to the preparation of compounds of the formula I. Referring to Scheme 1, compounds of formula I, wherein the heterocyclic ring X has the formulae a–n (i.e., a compound of the formulae Ia–In, respectively):

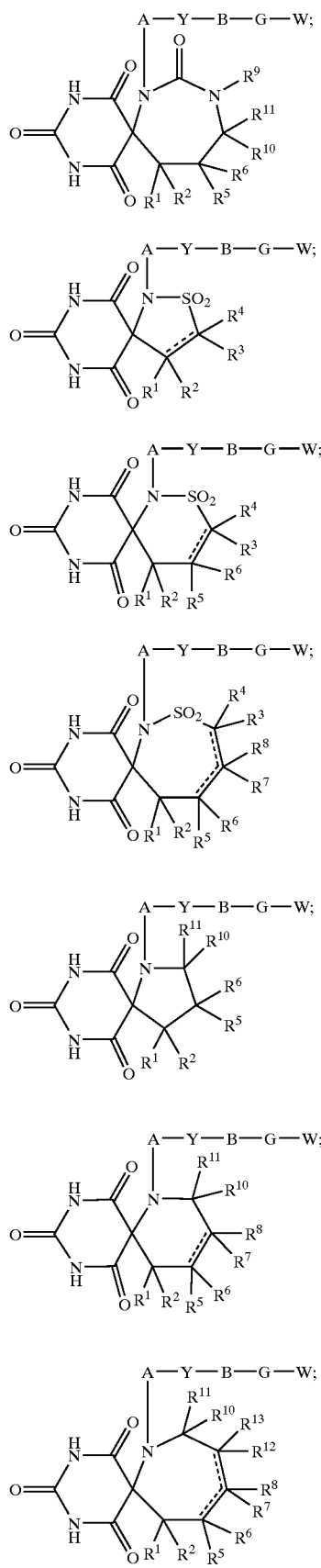
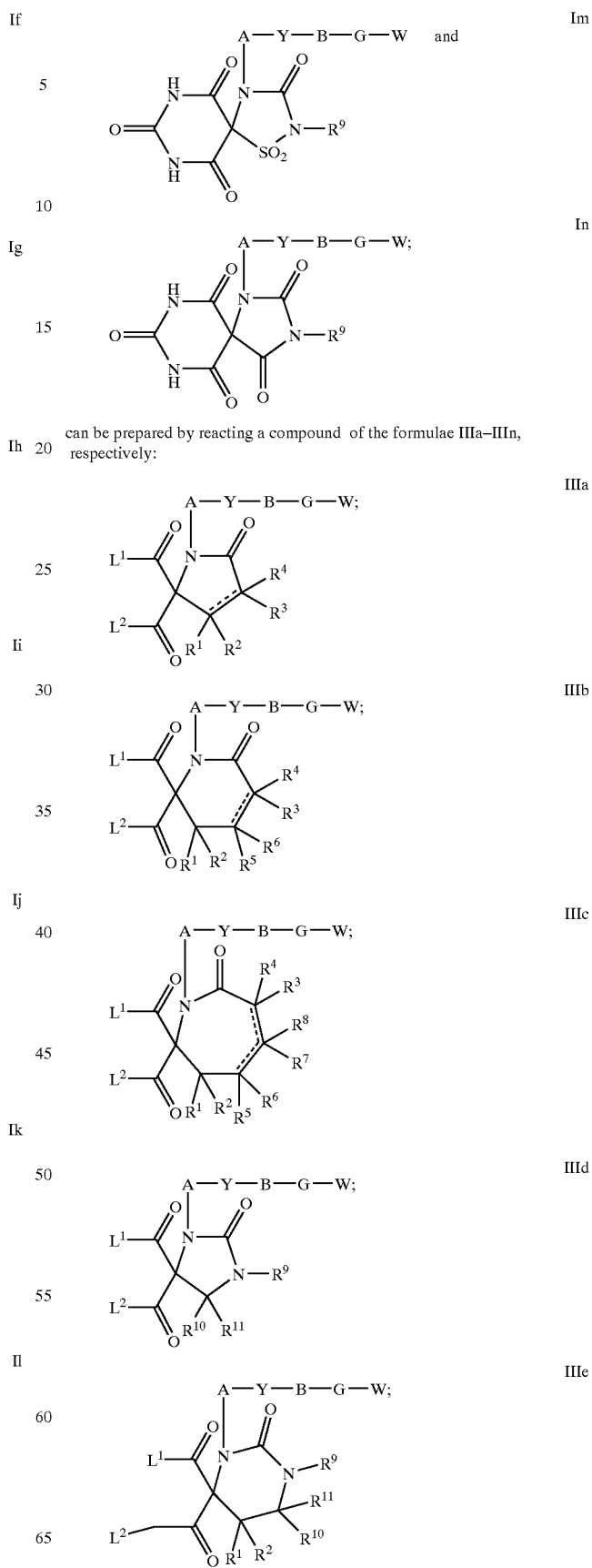
can be prepared by reacting a compound of the formulae IIIa–IIIn, respectively:

-continued

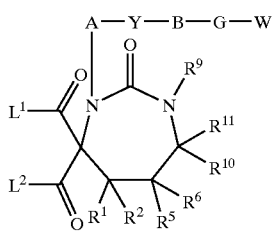
IIIf

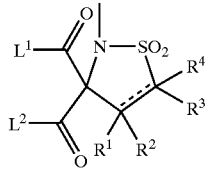
IIIg

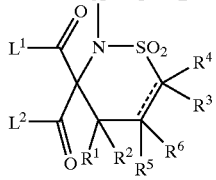
IIIh

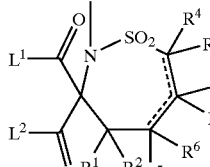
IIIi

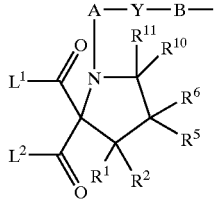
IIIj

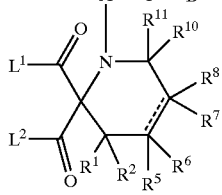
IIIk

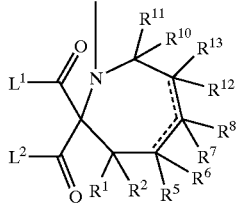
IIIl

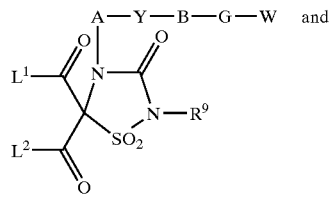
IIIm and

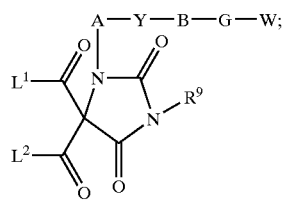
IIIn wherein $L^1$ and $L^2$ are leaving groups such as alkoxy, preferably methoxy, ethoxy or benzyloxy, more preferably methoxy or ethoxy, with a urea of formula II (i.e., $H_2N$—(CO)—$NH_2$) in the presence of a suitable base in a polar solvent. Suitable bases include alkoxide bases, such as sodium methoxide, sodium ethoxide, or potassium tert-butoxide, or sodium hydride, preferably sodium hydride. Suitable solvents include tetrahydrofuran, dimethylformamide, dimethyl sulfoxide, or alcohols (such as ethanol), preferably dimethyl sulfoxide. The aforesaid reaction is conducted at a temperature of about 20° C. to about 90° C., preferably about 25° C., for a time period of about 5 minutes to about 8 hours, preferably about 1 hour.

A compound of formulae IIIa–IIIl, respectively,

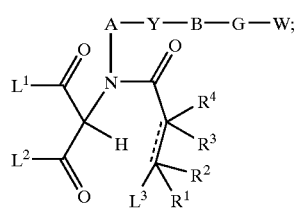
IVa

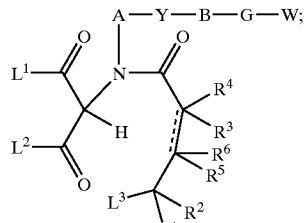
IVb

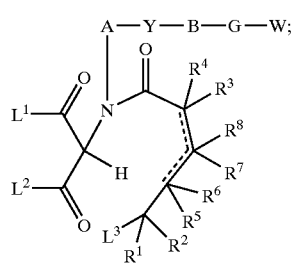
IVc

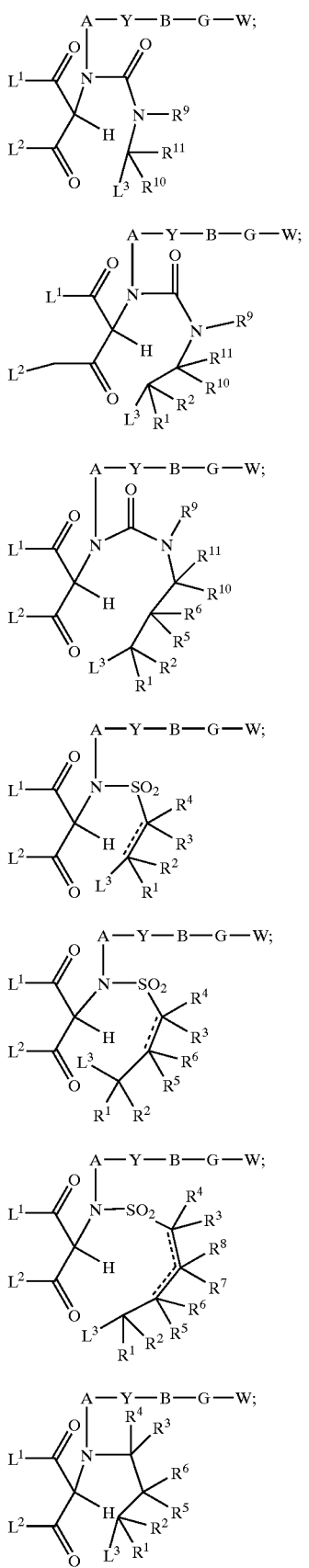

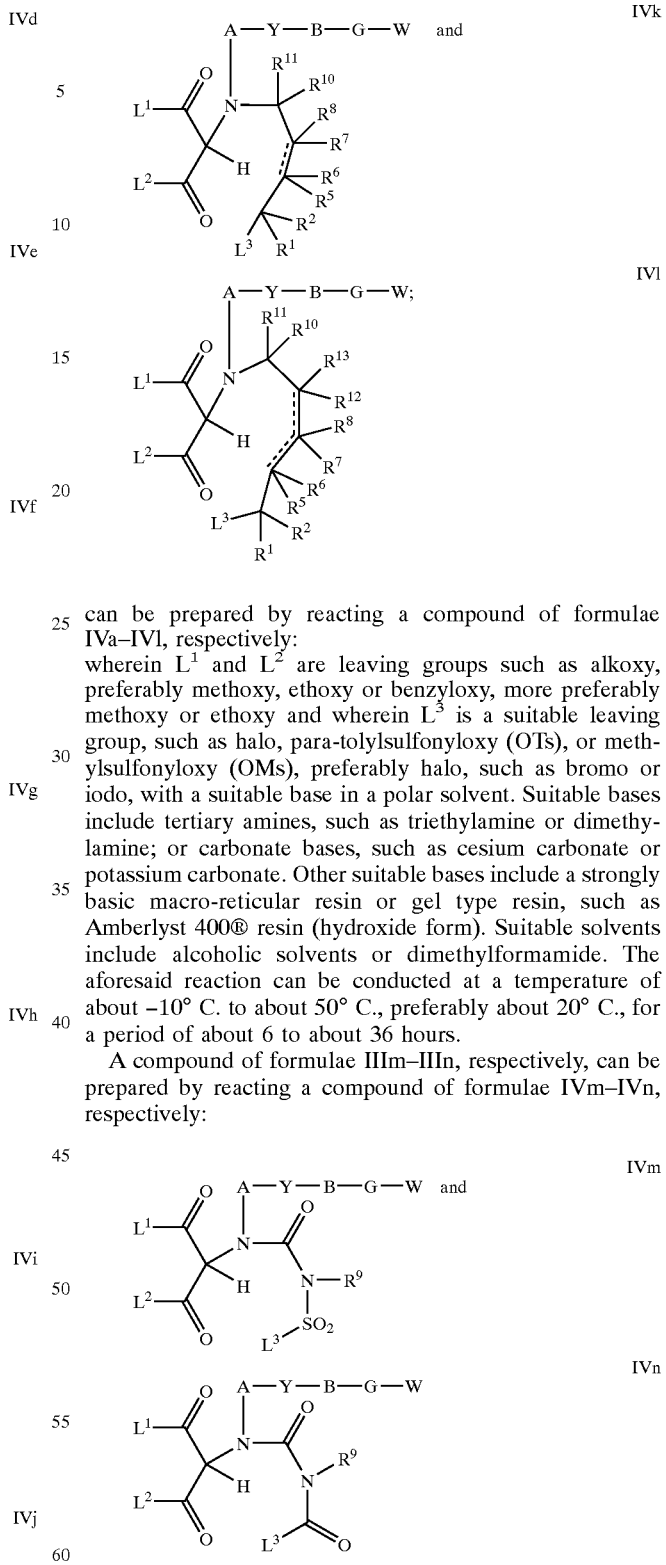

can be prepared by reacting a compound of formulae IVa–IVl, respectively:

wherein $L^1$ and $L^2$ are leaving groups such as alkoxy, preferably methoxy, ethoxy or benzyloxy, more preferably methoxy or ethoxy and wherein $L^3$ is a suitable leaving group, such as halo, para-tolylsulfonyloxy (OTs), or methylsulfonyloxy (OMs), preferably halo, such as bromo or iodo, with a suitable base in a polar solvent. Suitable bases include tertiary amines, such as triethylamine or dimethylamine; or carbonate bases, such as cesium carbonate or potassium carbonate. Other suitable bases include a strongly basic macro-reticular resin or gel type resin, such as Amberlyst 400® resin (hydroxide form). Suitable solvents include alcoholic solvents or dimethylformamide. The aforesaid reaction can be conducted at a temperature of about −10° C. to about 50° C., preferably about 20° C., for a period of about 6 to about 36 hours.

A compound of formulae IIIm–IIIn, respectively, can be prepared by reacting a compound of formulae IVm–IVn, respectively:

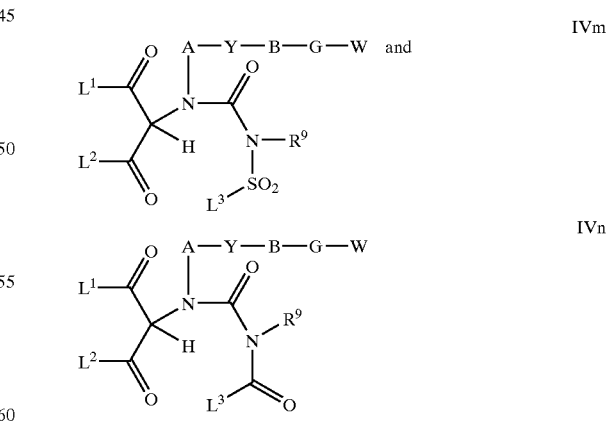

wherein $L^3$ is a suitable leaving group, with a suitable base in a polar solvent according to methods analogous to the preparation of the compounds of formulae IIIa–IIIi in the foregoing paragraph. Suitable leaving groups of the formula $L^3$ include halo, para-tolylsulfonyloxy (OTs), or methylsulfonyloxy (OMs). Preferably $L^3$ is halo, such as chloro. The aforesaid reaction can be conducted at a temperature of about 0° C. to about 50° C., preferably about 20° C., for a period of about 1 hour to about 4 hours. Suitable solvents include tetrahydrofuran, dimethylformamide and alcohol.

A compound of formulae IVa–IVi, respectively, can be prepared by reacting a compound of formula VI with a compound of general formula

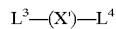   (V)

(i.e., a compound of formulae Va–Vi, respectively):

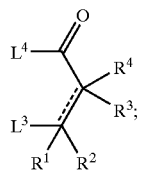  Va

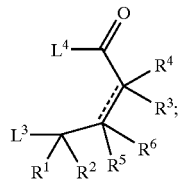  Vb

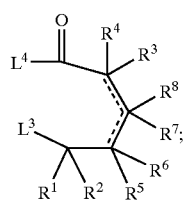  Vc

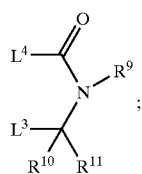  Vd

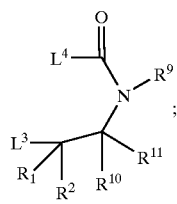  Ve

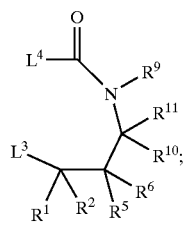  Vf

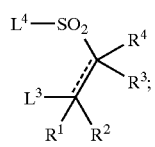  Vg

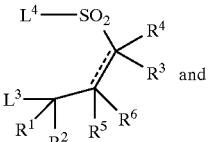  Vh and

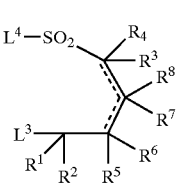  Vi wherein each of $L^3$ and $L^4$ is a suitable leaving group, such as halo, para-tolylsulfonyloxy (OTs), or methylsulfonyloxy (OMs). Preferably $L^3$ is halo, such as bromo, chloro or iodo. Preferably $L^4$ is chloro or fluoro. Optionally, the aforementioned reaction may be conducted in the presence of a tertiary amine base, such as N,N-dimethylaniline or pyridine in the presence of a polar aprotic solvent, such as dimethylformamide, tetrahydrofuran, or halogenated solvents such as methylene chloride. Alternatively the aforementioned reaction may be conducted in the presence of a carbonate base, such as cesium carbonate; in the presence of a suitable solvent, such as a hydrocarbon solvent (benzene or toluene), tetrahydrofuran, dimethylformamide, or methylene chloride. The aforementioned reaction is conducted at a temperature of about 20° C. to about 90° C., preferably about 50° C. to about 80° C., for a time period of about 30 minutes to about 6 hours.

A compound of formulae IVj–IVl, respectively, can be prepared by reacting a compound of formula VI with a compound of formula:

$L^3—(X')—L^4$   (V)

(i.e., a compound of formulae Vj–Vl, respectively):

Vj

Vk and

Vl wherein each of $L^3$ and $L^4$ is a suitable leaving group, such as halo, para-tolylsulfonyloxy (OTs) or methylsulfonyloxy (OMs), according to the methods analogous to those described in the preparation of the compounds of formulae IVa–IVi in the foregoing paragraph. Preferably $L^3$ is chloro, bromo, or iodo. Preferably $L^4$ is chloro, bromo, or iodo. The aforesaid reaction can be conducted at a temperature of about 0° C. to about 50° C., preferably about 20° C., for a time period of about 30 minutes to about 12 hours.

Compounds of formulae IVm–IVn, respectively, can be prepared by reacting a compound of formula VI with a compound of formula

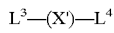

$$L^3\text{—}(X')\text{—}L^4 \quad (V)$$

(i.e., a compound of formulas Vm–Vn, respectively):

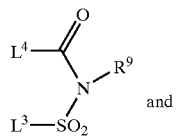

Vm and

Vn

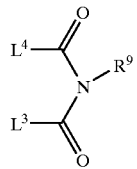

wherein each of $L^3$ and $L^4$ is a suitable leaving group, such as halo, para-tolylsulfonyloxy (OTs) or methylsulfonyloxy (OMs), according to the methods analogous to those described in the preparation of the compounds of formulae IVa–IVi in the foregoing paragraph. Preferably $L^3$ is halo, such as chloro. Preferably $L^4$ is halo, such as chloro. The aforesaid reaction can be conducted at a temperature of about 0° C. to about 80° C., preferably about 0° C. to about 40° C., for a time period of about 30 minutes to about 8 hours.

Alternatively, compounds of formulae IVd, IVe and IVf, respectively, can be prepared by reacting a compound of formula VI with a compound of formula

$$(X')\text{—}L^3 \quad (V)$$

(i.e., a compound of formulae Vd', Ve' and Vf', respectively):

Vd'
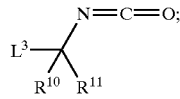

Ve'
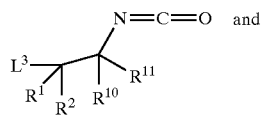
and

Vf'
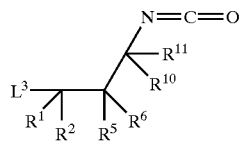

wherein $L^3$ is preferably halo, most preferably chloro, bromo, or iodo. Optionally, the aforementioned reaction can be conducted in the presence of a tertiary amine base in a suitable solvent. Suitable bases include N,N-dimethylaniline or pyridine. Suitable solvents include hydrocarbon solvent (benzene or toluene), tetrahydrofuran, or methylene chloride, preferably aromatic hydrocarbon solvent, such as benzene or toluene. The aforementioned reaction is conducted at a temperature of about 20° C. to about 90° C., preferably about 50° C. to about 80° C., for a time period of about 30 minutes to about 6 hours. Preferably, the aforementioned reaction is conducted in the absence of any aforementioned base.

Alternatively, compounds of formulae IVm and IVn, respectively, can be prepared by reacting a compound of formula VI with a compound of formula

$$(X')\text{—}L^3 \quad (V)$$

(i.e., a compound of formulae Vm' and Vn', respectively):

Vm'
$$L^3\text{—}SO_2\text{—}N\text{=}C\text{=}O \quad \text{and}$$

Vn'
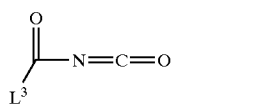

wherein $L^3$ is preferably halo, most preferably chloro. The aforementioned reaction can be conducted optionally in the presence of a tertiary amine base in a suitable solvent. Suitable bases include N,N-dimethylaniline or pyridine. Suitable solvents include a hydrocarbon solvent (benzene or toluene), tetrahydrofuran or methylene chloride, preferably aromatic hydrocarbon solvent, such as benzene or toluene. The aforesaid reaction can be conducted at a temperature of about –10° C. to about 50° C., preferably about 0° C. to about 30° C., for a time period of about 30 minutes to about 12 hours. Preferably, the aforementioned reaction is conducted in the absence of any aforementioned base.

A compound of formula VI can be prepared by reacting a compound of formula $H_2N\text{—}A\text{—}Y\text{—}B\text{—}G$ with a compound of the formula VII:

VII
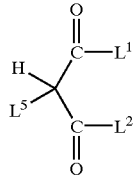

wherein $L^1$ and $L^2$ are leaving groups, such as methoxy, ethoxy, or benzyloxy; preferably ethoxy; and $L^5$ is a leaving group, such as halo, para-tolylsulfonyloxy (OTs) or methylsulfonyloxy (OMs); preferably halo; most preferably chloro or bromo. The aforesaid reaction can be performed either neat or in the presence of a suitable solvent, preferably neat, in the presence of a suitable base. Suitable solvents include tetrahydrofuran or dimethylformamide. Suitable bases include a weak tertiary amine base, preferably tertiary aniline bases, most preferably N,N-dimethylaniline. Preferably, the aforementioned reaction is conducted at a temperature of about 23° C. to about 100° C., preferably about 50° C. to about 90° C., for a time period of about 30 minutes to about 24 hours.

In the aforesaid reactions, each of the compounds of formulae IVj–IVl may be isolated, but are preferably carried on to the next step without isolation. Thus, in Scheme 1, the compound of formulae IIIj–IIIl is preferably prepared in a one-pot preparation from a compound of the formula VI.

If the compounds of the formulae IVj–IVl are not isolated, the suitable solvent for the one-pot preparation is dimethylformamide, tetrahydrofuran, or alcohols, preferably alcohols, such as ethanol. Preferably, the one-pot preparation is conducted in the presence of a suitable base. Suitable bases include an alkoxide base, preferably sodium methoxide or sodium ethoxide; or a carbonate base, such as cesium carbonate or potassium carbonate. The aforesaid one pot preparation is conducted at a temperature of about 40° C. to about 90° C., preferably about 60° C. to about 80° C., for a time period of about 15 minutes to about 12 hours.

The compounds of formula $H_2N$—A—Y—B—G—W are commercially available or can be made by methods well known to those skilled in the art. Alternatively, the compounds of formula $H_2N$—A—Y—B—G—W can be prepared as described in Scheme 3.

A compound of the formula VII can be made by methods well known in the art such as those described in PCT Patent Publication WO 98/58925 or reviewed in *The Organic Chemistry of Drug Synthesis*, D. Lednicer and L. A. Mitscher, Volume 1, pages 167 to 277 and references therein. Each of the above referenced publications and applications is hereby incorporated by reference in its entirety.

Compounds of the formula II are commercially available or can be made by methods well known to those skilled in the art.

Scheme 2 refers to the preparation of a compound of the formula I, wherein the heterocyclic ring X has the formula o, i.e., a compound of formula Io. Referring to Scheme 2, a compound of formula Io:

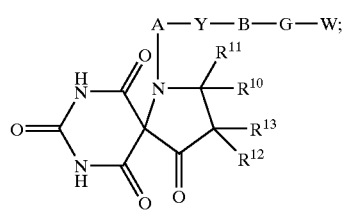

can be prepared by reacting a compound of the formula IIIo, wherein $L^1$ and $L^2$ are leaving groups, with a urea of formula II (i.e., $H_2N$—(CO)—$NH_2$) in the presence of a suitable base in a polar solvent. Suitable leaving groups include methoxy, ethoxy, or benzyloxy, preferably ethoxy. Suitable bases include alkoxide bases, such as sodium methoxide, sodium ethoxide and potassium tert-butoxide, preferably sodium ethoxide. Suitable solvents include tetrahydrofuran, dimethylformamide, or alcohols (such as ethanol), preferably tetrahydrofuran or dimethylformamide. The aforesaid reaction is conducted at a temperature of about 20° C. to about 90° C., preferably about 50° C. to about 80° C., for a time period of about 5 minutes to about 8 hours.

A compound of formula IIIo can be prepared by reacting a compound of formula IVo, wherein $L^3$ is a leaving group, with a suitable base in a polar solvent. Suitable leaving groups include alkoxy (such as methoxy, ethoxy, or benzyloxy) or halo; preferably methoxy or ethoxy. Suitable bases include alkoxide bases, preferably sodium methoxide or sodium ethoxide. Suitable solvents include alcohols, preferably ethanol. The aforesaid reaction can be conducted at a temperature of about 0° C. to about 90° C., preferably of about 60° C. to about 90° C., for a period of about 1 hour to about 36 hours.

A compound of formula IVo can be prepared by reacting a compound of formula VI with the compound of formula Vo:

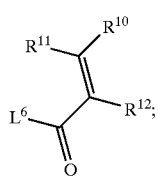

wherein $L^6$ is a suitable leaving group, in a suitable solvent. Suitable $L^6$ includes alkoxy or halo, such as chloro; preferably alkoxy; more preferably methoxy or ethoxy. Optionally, the aforesaid reaction may be conducted in the presence of a suitable tertiary amine base, such as triethylamine, N,N-dimethylaniline, or pyridine. Suitable solvents, include hydrocarbon solvents (benzene or toluene), tetrahydrofuran, or methylene chloride, preferably tetrahydrofuran. Preferably, the aforementioned reaction is conducted in tetrahydrofuran or dimethylformamide, in the presence of the aforementioned suitable tertiary amine base. The aforesaid reaction may be conducted at a temperature of about 20° C. to about 90° C., preferably about 50° C. to about 80° C., for a time period of about 30 minutes to about 6 hours.

In the aforesaid reactions, a compound of formula IVo may be isolated, but is preferably carried on to the next step without isolation. Thus, in Scheme 1, a compound of formula IIIo is preferably prepared in a one-pot preparation from a compound of the formula VI.

If the compounds of the formulae IVo are not isolated, the suitable solvent for the one-pot preparation is dimethylformamide, tetrahydrofuran, or alcohols, preferably alcohol, such as ethanol. The aforesaid one pot preparation is suitably conducted at a temperature of about 0° C. to about 70° C., preferably about 23° C. to about 60° C., for a time period of about 30 minutes to about 24 hours.

A compound of formula VI can prepared by reacting a compound of formula $H_2N$—A—Y—B—G—W with a compound of the formula VII as described Scheme 1.

Scheme 3 refers to the preparation of compounds of the formula $H_2N$—A—Y—B—G—W, which are intermediates useful in the preparation of compounds of formula I in Schemes 1 and 2. Referring to Scheme 3, compounds of formula $H_2N$—A—Y—B—G—W can be prepared by reacting a compound of formula VIII with a reducing agent, such as tin II chloride, in the presence of a suitable acid, such as hydrochloric acid, in a polar protic solvent. Suitable solvents include an alcoholic solvent, water, or mixtures thereof, preferably a mixture of ethanol and water. The aforesaid reaction can be conducted at a temperature of about 40° C. to about 10° C. for a period of about 1 to about 12 hours.

Alternatively, the compounds of formula $H_2N$—A—Y—B—G—W can be prepared by reacting a compound of formula VIII with hydrogen gas, at a pressure between atmospheric pressure and 50 psi, in the presence of a catalyst and a polar solvent. Suitable catalysts include a Raney Nickel, palladium or platinum catalyst, preferably Raney Nickel or Adams catalyst (i.e., platinum oxide). Suitable solvents include an alcoholic solvent,tetrahydrofuran, or mixtures thereof. The aforesaid reaction can be conducted at a temperature of about 20° C. to about 50° C., preferably about 23° C. The aforesaid reaction can be performed for a period of about 30 minutes to about 6 hours.

A compound of the formula VIII, wherein Y is —O—, —S—, —$CH_2$S—, —$CH_2$O—, >$NR^{14}$, —$CH_2[N(R^{14})]$— or —SO₂[N(R¹⁴)]—, can be prepared by reacting a compound of formula X, wherein the group L⁷ is fluoro or chloro, with a compound of the formula:

W—G—B—Y—H          (IX)

wherein Y is —O—, —S—, —CH₂S—, —CH₂O—, >NR¹⁴, —CH₂[N(R¹⁴)]— or —SO₂[N(R¹⁴)]—, in the presence of a base in a polar aprotic solvent. Suitable bases include an alkali metal hydride base; preferably sodium hydride. Suitable solvents include dimethylformamide, tetrahydrofuran or 1,2-dimethoxyethane; preferably dimethylformamide. The aforesaid reaction can be conducted at a temperature of about 40° C. to about 140° C., preferably about 80° C. to about 120° C., for about 1 hour to about 24 hours.

Alternatively, the aforesaid compound of formula VIII, wherein Y is —O—, —S—, —CH₂S—, —CH₂O—, >NR¹⁴, —CH₂[N(R¹⁴)]— or —SO₂[N(R¹⁴)]—, can be prepared in presence of an alkali metal hydroxide base, preferably potassium hydroxide, optionally in the presence of a phase transfer catalyst, such as a quaternary ammonium or phosphonium salt, preferably tetrabutylammonium bromide, in an aromatic hydrocarbon solvent. Preferably the solvent is benzene or toluene. The aforesaid reaction can be conducted at a temperature of about 0° C. to about 120° C., preferably at about 23° C., for about 1 hour to about 12 hours.

Alternatively, the aforesaid compound of formula VIII, wherein Y is —O—, —S—, —CH₂S—, —CH₂O—, >NR¹⁴, —CH₂[N(R¹⁴)]— or —SO₂[N(R¹⁴)]—, can be prepared under so called "Ulman coupling" conditions. Under such conditions, the aforesaid compound of formula VIII can be prepared by reacting a compound of formula X, wherein the group L⁷ is bromo or chloro, with a compound of the formula:

W—G—B—Y—H          (IX), wherein Y is —O—, —S—, —CH₂S—, —CH₂O—, >NR¹⁴, —CH₂[N(R¹⁴)]— or —SO₂[N(R¹⁴)]—, in the presence of a base and a catalyst in a polar aprotic solvent. Suitable bases include an alkali metal carbonate or hydroxide base, preferably potassium carbonate. Suitable catalysts include a copper (0) catalyst, preferably finely powdered copper bronze. Suitable solvents include dimethylformamide or 1-methyl-2-pyrrolidinone. The aforesaid reaction can be conducted at a temperature of about 80° C. to about 140° C., for about 6 hours to about 24 hours.

A compound of formula VII, wherein the group Y is in an oxidized state, i.e., >SO₂, >S=O, —CH₂SO—, —CH₂SO₂—, SOCH₂— or —SO₂CH₂—, can be prepared by reacting a corresponding compound of formula VIII, wherein the group Y is in a corresponding lower oxidation state, with a suitable oxidizing agent in a solvent. The corresponding lower oxidation state for each compound of formula VIII, wherein the group Y is >SO₂ and >S=O is a compound of formula VIII, wherein the group Y is S. The corresponding lower oxidation state for each compound of formula VIII, wherein the group Y is —CH₂SO₂— and —CH₂SO— is a compound of formula VIII, wherein the group Y is —CH₂S—. The corresponding lower oxidation state for each compound of formula VIII, wherein the group Y is —SO₂CH₂— and —SOCH₂— is a compound of formula VIII, wherein the group Y is —SCH₂— Suitable oxidizing agents include a peroxy acid, preferably peracetic acid, or an organic peroxide, preferably m-chloroperoxybenzoic acid or tert-butyl hydroperoxide.

Suitable solvents include methylene chloride or alcohol, such as ethanol. The aforesaid reaction can be conducted at a temperature of about −10° C. to about 30° C., for about 1 hour to about 8 hours.

A compound of the formula VIII, wherein Y is —OCH₂—, —SCH₂— or —[NR¹⁴](CH₂)—, respectively, can be prepared by reacting a compound of the formula X, wherein the group L⁷ is L⁸—CH₂— and wherein the group L⁸ is halo, such as chloro, bromo, iodo, mesyloxy (MsO), or tosyloxy (TsO), with a compound of formula:

W—G—B—M—H          (IX)

wherein the group M is —O—, —S—, or —NR¹⁴, respectively, in the presence of a base in a polar aprotic solvent. Suitable bases include an alkali metal carbonate base, preferably potassium carbonate or cesium carbonate. Suitable solvents include dimethylformamide or tetrahydrofuran. The aforesaid reaction can be conducted at a temperature of about 23° C. to about 80° C., preferably about 20° C. to about 50° C., for about 1 to about 24 hours.

A compound of the formula VIII, wherein Y is >C=O, —CH=CH— or —C≡C—, can be prepared by reacting a compound of formula X, wherein the group L⁷ is dihydroxyborane; zinc halide; such as zinc chloride; or trialkyl tin, such as tributyl tin, with a compound of the formula:

W—G—B—Y—L⁹          (IX)

wherein Y is >C=O, —CH=CH— or —C≡C—; and wherein the group L⁹ is halo; preferably chloro, bromo or iodo; in the presence of a catalyst in a solvent. Suitable catalysts include a palladium or nickel catalyst, preferably tetrakis triphenyl phosphine palladium (0) (Pd(PPh₃)₄). Suitable solvents include toluene, tetrahydrofuran, dimethylformamide, or dimethylsulfoxide. The aforesaid reaction can be conducted at a temperature of about 23° C. to about 110° C., for a period of about 1 hour to about 24 hours. Such reactions can be facilitated by the presence of a copper salt, such as cuprous iodide or cuprous bromide.

Alternatively, a compound of the formula VIII, wherein Y is —C≡C—, can be prepared by reacting a compound of formula X, wherein L⁷ is halo or triflate, preferably bromo or iodo, with a compound of the formula:

W—G—B—Y—H          (IX)

in the presence of a base, such as a trialkylamine base, preferably triethylamine and a palladium catalyst, preferably Pd(PPh₃)₄ in a solvent. Suitable solvents include tetrahydrofuran or dimethylformamide. The aforesaid reaction can be conducted at a temperature of about 23° C. to about 60° C. for a period of about 1 to about 24 hours.

Scheme 4 refers to the preparation of compounds of the formula IX (i.e., W—G—B—Y—H), which are intermediates useful in the preparation of compounds of formula VIII in Scheme 3. Referring to scheme 4, compounds of the formula W—G—B—Y—H, can be prepared by various deprotection reaction of compounds of the formula XI (i.e., W—G—B—Y—P), wherein P is a suitable protecting group. Conditions for these deprotections are well known to those skilled in the art and can be found in Greene and Wuts, "Protecting Groups in Organic Synthesis," (John Wiley & Sons, 3ʳᵈ Ed).

Compounds of the formula XI (W—G—B—Y—P), wherein —G— is an oxazole substituted by —W in the 5-position and by —B— in the 2-position, can be prepared by reacting an organozinc oxazole of the formula M—G—W, wherein M is zinc, (see Katritzky et al., *Tetrahedron Lett*, 1989, 6657) and a compound of the formula $L^{10}$—B—Y—P (wherein $L^{10}$ is a leaving group such as iodide or triflate) via a palladium mediated cross coupling (a so-called Negishi coupling) reaction according to methods found in *Synthesis*, 1996, 583.

Compounds of the formula XI (W—G—B—Y—P), wherein —G— is an oxazole substituted by —W in the 2-position and by —B— in the 5-position, can be prepared by reacting a compound of the formula 5-bromo-G—W (see Kashima et al. *Synthesis* 1989, 873) with a compound of the formula $L^{10}$—B—Y—P (wherein $L^{10}$ is B(OH)$_2$ via a palladium mediated cross coupling (a so-called Suzuki coupling) reaction according to Miyaura et al., *Chem. Reviews*, 1995, 95, 2457.

Compounds of the formula XI (W—G—B—Y—P), wherein —G— is a 1,2,4-oxadiazole substituted by —W in the 3-position and by —B— in the 5 position, can be prepared by reacting a compound of the formula W—$L^{11}$ (wherein $L^{11}$ is cyano) with hydroxylamine (see Gangloff et al., *Tetrahedron Lett*, 2001, 42, 1441) to form an amidoxime. The amidoxime can then be reacted with a compound of the formula $L^{10}$—B—Y—P (wherein $L^{10}$ is a carboxylic acid) in the presence of a suitable peptide coupling reagents and a suitable base in a polar aprotic solvent. Preferably, the suitable peptide coupling reagents are 2-(1H-benxotriazol-1-yl)-1,1,3,3-tetramethyluronium tetrafluoroborate and 1-hydroxybenztriazole. Suitable bases include amine bases, preferably diisopropylethylamine. Suitable polar aprotic solvents include dimethylformamide or tetrahydrofuran, preferably dimethylformamide. The aforesaid reaction can be conducted at a temperature of about 0° C. to about 140° C., preferably at about 120° C. The aforesaid reaction can be conducted for a period of about 1 hour to about 48 hours, preferably about 6 hours.

Compounds of the formula XI (W—G—B—Y—P), wherein —G— is a 1,3,4-oxadiazole substituted by —W in the 2-position and by —B— in the 5-position, can be prepared by reacting a compound of the formula $L^{10}$—B—Y—P (wherein $L^{10}$ is a carboxylic ester) with hydrazine, followed by a compound of the formula W—$L^{11}$ (wherein $L^{11}$ is an acyl chloride) to form a 1,2-diarylhydrazine. The 1,2-diarylhydrazine can then be converted to the desired products according to the methods described in Blackhall et al., *J. Chem Soc. Perkin* 2, 1980, 773.

Compounds of the formula XI (W—G—B—Y—P), wherein —G— is an oxazole substituted by —W in the 2-position and by —B— in the 4-position, can be prepared by reacting a compound of the formula $L^{10}$—B—Y—P (wherein $L^{10}$ is an α-halo ketone) with a compound of the formula W—$L^{11}$ (wherein $L^{11}$ is a primary carboxamide) according to the methods described in Maeda et al., *J. Chem Soc. Perkin* 1, 1977, 239.

Compounds of the formula XI (W—G—B—Y—P), wherein —G— is a 4,5-dihydro-oxazole substituted by —W in the 4-position and by —B— in the 2-position, can be prepared by reacting a compound of the formula $L^{10}$—B—Y—P (wherein $L^{10}$ is a carboxylic acid) with a compound of the formula W—$L^{11}$ (wherein $L^{11}$ is 1-amino-2-chloroethyl) according to standard peptide coupling conditions which are well known to those skilled in the art, followed by a cyclization reaction under basic conditions to the desired 4,5-dihydro-oxazole according to the methods described in Leffler et al., *J. Am. Chem. Soc.*, 1937, 2252.

Compounds of the formula XI (W—G—B—Y—P), wherein —G— is a 1,2,4-oxadiazole substituted by W— in the 5-position and by —B— in the 3-position can be prepared by reacting a compound of the formula $L^{10}$—B—Y—P (wherein $L^{10}$ is cyano) with hydroxylamine (see Gangloff et al., *Tetrahedron Lett*, 2001, 42, 1441) to form an amidoxime. The amidoxime can then be reacted with a compound of the formula W—$L^{11}$ (wherein $L^{11}$ is acyl chloride) to form the desired oxadiazole according to procedures found in Malamas et al., *J. Med. Chem.*, 2000, 995.

Compounds of the formula XI (W—G—B—Y—P), wherein —G— is an isoxazole substituted by —W in the 3-position and by —B— in the 5-position can be prepared by reacting a compound of the formula $L^{10}$—B—Y—P (wherein $L^{10}$ is cyano) with a compound of the formula W—$L^{11}$ (wherein $L^{11}$ is a methyl ketoxime) according to procedures found in Beam et al., *J. Het. Chem.*, 1972, 183.

Compounds of the formula XI (W—G—B—Y—P), wherein —G— is an isoxazole substituted by —W in the 5-position and by —B— in the 3-position can be prepared by deprotonation reaction of a compound of the formula $L^{10}$—B—Y—P (wherein $L^{10}$ is a terminal acetylene) with a suitable base, followed by reaction with a compound of the formula W—$L^{11}$ (wherein $L^{11}$ is an acyl chloride) to form an acetylenic ketone. The resulting acetylenic ketones can then be reacted with hydroxylamine to produce the desired isoxazole according to procedures found in Linderman et al., *Tetrahedron Lett.*, 1989, 2049. Suitable bases include an alkyl lithium base, preferably n-butyl lithium. The aforesaid deprotonation reaction can be conducted at a temperature of about −78° C. to about 60° C., preferably at about 0° C., for a period of about 0.5 hour to about 6 hours, preferably about 1 hour. The reaction with a compound of the formula W—$L^{11}$ can be conducted at a temperature of about 0° C. to about 80° C., preferably at about 25° C. ,for a period of about 1 hour to about 48 hours, preferably about 4 hours.

Other compounds of the formula X and IX (i.e., compounds of the formula W—G—B—Y—H, W—G—B—M—H, or W—G—B—$L^9$) as well as compounds of the formula W—$L^{11}$ and $L^{10}$—B—Y—P discussed above are either commercially available or can be prepared by methods well known to those skilled in the art.

Scheme 5 describes an alternative preparation of compounds of formula III (i.e., a compound of the formulae IIIa–IIIn, as defined in the description of Scheme 1 above, which are intermediates used in Scheme 1. Referring to Scheme 5, compounds of formula IIIa–IIIn may be prepared by reacting a compound of formula XIIa–XIIn, wherein each of $L^1$ and $L^2$ is a suitable leaving group, such as alkoxy, preferably methoxy, ethoxy or benzyloxy, more preferably ethoxy, and wherein $L^8$ is a leaving group, such as halo, preferably iodo; with a compound of formula XIII:

M—G—W  (XIII);

wherein M is a metal, such as zinc or copper, preferably zinc, according to procedures which are well known to one skilled in the art, such as those described in *Synthesis*, 1996, 583 and references therein.

Compounds of formula XIII may be synthesized by procedures known by those skilled in the art, for example see Katritzky et al., *Tetrahedron Lett*, 1989, 6657.

Compounds of formulae XIIa–XIII, respectively:

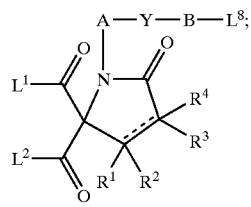
XIIa

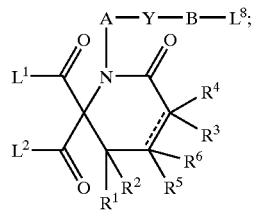
XIIb

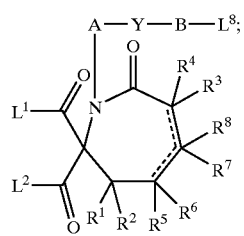
XIIc

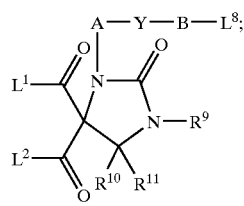
XIId

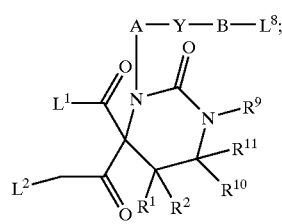
XIIe

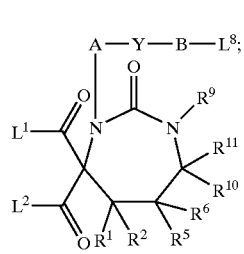
XIIf

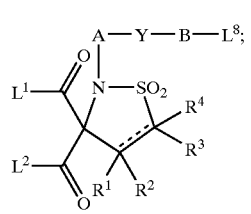
XIg

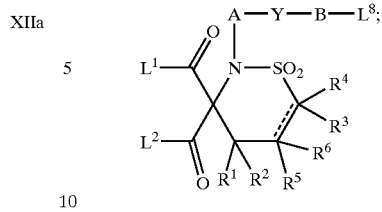
XIh

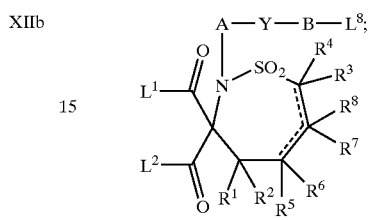
XIi

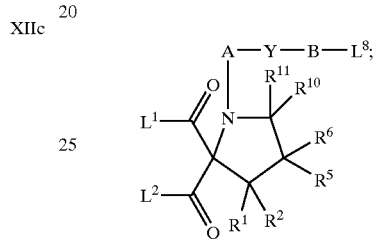
XIIj

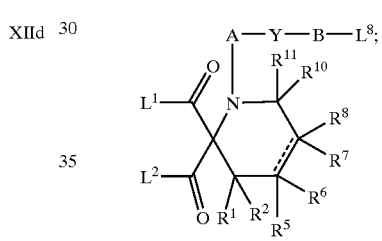
XIIk

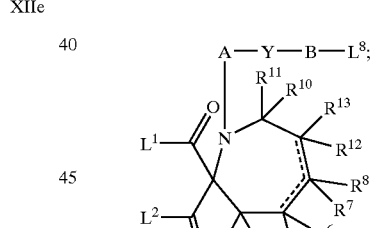
XIII wherein $L^1$ and $L^2$ are leaving groups such as alkoxy, preferably methoxy, ethoxy or benzyloxy, more preferably methoxy or ethoxy, and wherein $L^8$ is a leaving group, such as halo, preferably iodo; can be prepared by reacting a compound of formulae XIVa–XIVl, respectively:

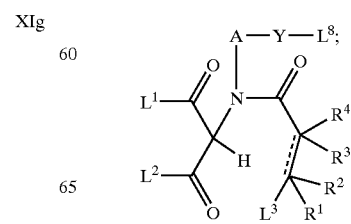
XIV(a)

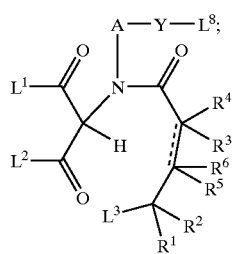
XIV(b)

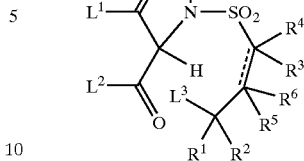
XIV(h)

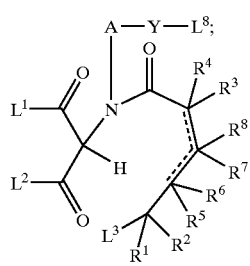
XIV(c)

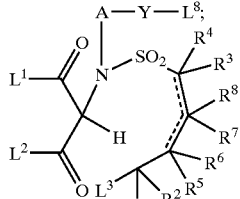
XIV(i)

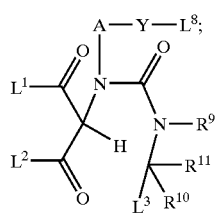
XIV(d)

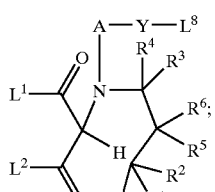
XIV(j)

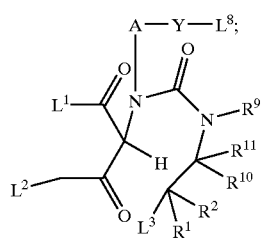
XIV(e)

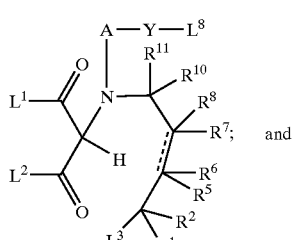
XIV(k)

and

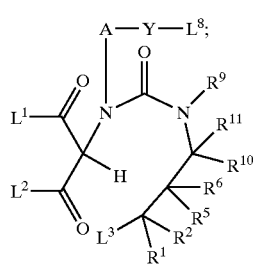
XIV(f)

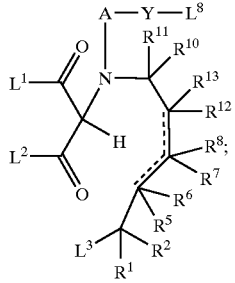
XIV(l)

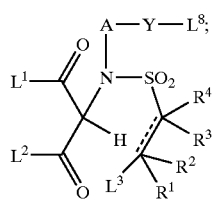
XIV(g)

wherein $L^1$ and $L^2$ are leaving groups such as alkoxy, preferably methoxy, ethoxy or benzyloxy, more preferably methoxy or ethoxy and wherein $L^3$ is a suitable leaving group, such as halo, para-tolylsulfonyloxy (OTs), or methylsulfonyloxy (OMs), preferably halo, such as bromo or iodo, with a suitable base in a polar solvent. Suitable bases include tertiary amines, such as triethylamine or dimethylamine; or carbonate bases, such as cesium carbonate or potassium carbonate. Other suitable bases include a strongly basic macro-reticular resin or gel type resin, such as Amberlyst 400® resin (hydroxide form). Suitable solvents include alcoholic solvents or dimethylformamide. The aforesaid reaction can be conducted at a temperature of about −10° C. to about 50° C., preferably about 20° C., for a period of about 6 to about 36 hours.

Compounds of formulae XII(m)–XII(n), respectively,

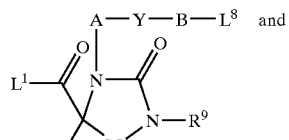
XII(m)

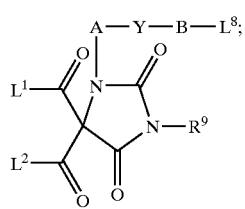
XII(n)

wherein $L^1$ and $L^2$ are leaving groups such as alkoxy, preferably methoxy, ethoxy or benzyloxy, more preferably methoxy or ethoxy, and wherein $L^8$ is a leaving group, such as halo, preferably iodo; can be prepared by reacting a compound of formulae XIV(m)–XIV(n), respectively:

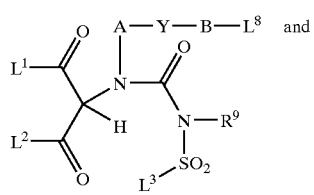
XIV(m)

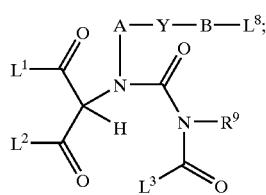
XIV(n)

wherein $L^1$ and $L^2$ are leaving groups such as alkoxy, preferably methoxy, ethoxy or benzyloxy, more preferably methoxy or ethoxy; wherein $L^8$ is a leaving group, such as halo, preferably iodo; and $L^3$ is a suitable leaving group, with a suitable base in a polar solvent according to methods analogous to the preparation of the compounds of formulae XII(a)–XII(l) in the foregoing paragraph. Suitable leaving groups of the formula $L^3$ include halo, para-tolylsulfonyloxy (OTs), or methylsulfonyloxy (OMs). Preferably $L^3$ is halo, such as chloro. The aforesaid reaction can be conducted at a temperature of about 0° C. to about 50° C., preferably about 20° C., for a period of about 1 hour to about 4 hours. Suitable solvents include tetrahydrofuran, dimethylformamide and alcohol.

Compounds of formula XIV(a)–XIV(n), as defined above, can be prepared by reacting a compound of formula XV with a compound of formula V $$L^3-(X')-L^4 \qquad (V);$$

(i.e., a compound of formulae Va–Vn, respectively, as defined in the description of Scheme 1 above); and wherein $L^3$ and $L^4$ are suitable leaving groups, such as halo, para-tolylsulfonyloxy (OTs), or methylsulfonyloxy (OMs), preferably halo, such as bromo or iodo, with a suitable base in a polar solvent. Suitable bases include tertiary amines, alkali carbonate bases such as cesium carbonate, or a strongly basic macro-reticular resin or gel type resin; preferably cesium carbonate. Suitable solvents include alcoholic solvents and dimethylformamide, preferably dimethylformamide. The aforesaid reaction can be conducted at a temperature of about −10° C. to about 50° C., preferably about 20° C. The aforesaid reaction can be conducted for a period of about 6 hours to about 36 hours.

Scheme 6 describes a preparation of compounds of formula XV, which are intermediates used in Scheme 5. Referring to Scheme 6, compounds of formula XV may be prepared by reacting a compound of formula XVI, wherein $L^8$ is a leaving group, such as halo, preferably iodo, with a compound of the formula VII, as defined above in the description of Scheme 1, in the presence of a base, optionally in the presence of a suitable solvent. Suitable solvents include tetrahydrofuran or dimethylformamide, preferably the reaction is performed neat. Suitable bases include a weak tertiary amine base, preferably tertiary aniline bases, more preferably N,N-dimethylaniline. The aforementioned reaction can be conducted at a temperature of about 23° C. to about 100° C., preferably about 50° C. to about 90° C. The aforesaid reaction can be conducted for a time period of about 30 minutes to about 24 hours, preferably about 4 hours.

Compounds of formula XVI can be prepared by reacting a compound of formula XVII with a reducing agent in the presence of a catalyst and a polar solvent. Suitable reducing agents include hydrogen gas at a pressure between atmospheric pressure and 50 psi or tin(II)chloride; preferably hydrogen gas. Suitable catalysts include a Raney Nickel or platinum catalyst, preferably Raney Nickel. Suitable solvents include an alcoholic solvent or tetrahydrofuran. The aforesaid reaction can be conducted at a temperature of about 20° C. to about 50° C., preferably about 23° C. The aforesaid reaction can be conducted for a period of about 30 minutes to about 6 hours, preferably about 2 hours.

Compounds of formula XVII, wherein Y is —O—, —S—, —CH$_2$S—, —CH$_2$O—, >NR$^{14}$, —CH$_2$[N(R$^{14}$)]—, —SO$_2$[N(R$^{14}$)]—, OCH$_2$—, —SCH$_2$— or —[NR$^{14}$](CH$_2$)—, and $L^8$ is a leaving group, such as halo, preferably iodo, can be prepared by reacting a compound of the formula XVIII, wherein $L^9$ is halo, preferably chloro, with a compound of the formula XIX:

$$Y-B-L^8 \qquad (XIX);$$

wherein $L^8$ is a leaving group, such as halo, preferably iodo, in presence of a base, optionally in the presence of a phase transfer catalyst in a hydrocarbon solvent. Suitable leaving groups include halo, preferably iodo. Preferably the solvent is benzene or toluene. Suitable bases include an alkali metal hydroxide base, such as potassium hydroxide. Suitable phase transfer catalysts include a quaternary ammonium salt, preferably tetrabutylammonium bromide, or a phosphonium salt. The aforesaid reaction can be conducted at a temperature of about 0° C. to about 120° C., preferably at about 23° C. The aforesaid reaction can be conducted for a period of about 1 hour to about 12 hours.

A compound of formula XVII, wherein Y is in an oxidized state, i.e., >SO$_2$, >S=O, —CH$_2$SO—, —CH$_2$SO$_2$—, SOCH$_2$— or —SO$_2$CH$_2$—, can be prepared by reacting a corresponding compound of formula XVII, wherein Y is in a corresponding lower oxidation state, with a suitable oxidizing agent in a solvent. The corresponding lower oxidation state for each compound of formula XVII, wherein Y is >SO$_2$ and >S=O is a compound of formula XVII, wherein Y is S. The corresponding lower oxidation state for each compound of formula XVII, wherein Y is —CH$_2$SO$_2$— and —CH$_2$SO— is a compound of formula XVII, wherein Y is —CH$_2$S—. The corresponding lower oxidation state for each compound of formula XVII, wherein Y is —SO$_2$CH$_2$— and —SOCH$_2$— is a compound of formula XVII, wherein Y is —SCH$_2$—. Suitable oxidizing agents include a peroxy acid, preferably peracetic acid, or an organic peroxide, preferably m-chloroperoxybenzoic acid or tert-butyl hydroperoxide. Suitable solvents include methylene chloride or alcohol, such as ethanol. The aforesaid reaction can be conducted at a temperature of about −10° C. to about 30° C. The aforesaid reaction can be conducted for about 1 hour to about 8 hours.

A compound of the formula XVII, wherein Y is >C=O, —CH=CH— or —C≡C—, respectively, and L$^8$ is a leaving group, such as halo, can be prepared by reacting a compound of the formula XVIII, wherein L$^9$ is dihydroxyborane; zinc halide, such as zinc chloride; or trialkyl tin, such as tributyl tin, with a compound of the formula XIX:

$$L^{10}—Y—B—L^8 \qquad (XIX)$$

wherein Y is >C=O, —CH=CH— or —C≡C—; and wherein the group L$^{10}$ is halo; preferably chloro, bromo or iodo; and L$^8$ is as defined above; in the presence of a catalyst in a solvent. Suitable catalysts include a palladium or nickel catalyst, preferably tetrakis triphenyl phosphine palludium (0) (Pd(PPh$_3$)$_4$). Suitable solvents include toluene, tetrahydrofuran, dimethylformamide, or dimethylsulfoxide. The aforesaid reaction can be conducted at a temperature of about 23° C. to about 110° C., for a period of about 1 hour to about 24 hours. Such reactions can be facilitated by the presence of a copper salt, such as cuprous iodide or cuprous bromide.

The compounds of the formula I, which are basic in nature, are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure.

Alternatively, these salts may also be prepared by mixing lower alkanolic solutions of the acidic compounds and the desired alkali metal alkoxide together and then evaporating the resulting solution to dryness in the same manner as before. In either case, stoichiometric quantities of reagents are preferably employed in order to ensure completeness of reaction and maximum product yields.

BIOLOGICAL ASSAYS

The ability of the compounds of formula I or their pharmaceutically acceptable salts (hereinafter also referred to as the compounds of the present invention) to inhibit metalloproteinases or mammalian reprolysins and, consequently, demonstrate their effectiveness for treating diseases characterized by metalloproteinase activity may be shown by the following in vitro and in vivo assay tests.

MMP Assays

MMP-13 selective inhibitors may be identified by screening the inhibitors of the present invention through-the MMP fluorescence assays described below and selecting those agents with MMP-X/MMP-13 inhibition IC$_{50}$ ratios of 100 or greater and potency of less than 100 nM, where MMP-X refers to one or more other MMPs.

Non-selective collagenase inhibitors as used herein, unless otherwise mentioned, refer to agents which exhibit less than a 100 fold selectivity for the inhibition of MMP-13 enzyme activity over MMP-X enzyme activity or a potency of more than 100 nM as defined by the IC$_{50}$ results from the MMP-13 and MMP-X fluorescence assays described below.

The ability of collagenase inhibitors to inhibit collagenase activity is well known in the art. The degree of inhibition of a particular MMP for several compounds has been well documented in the art and those skilled in the art will know how to normalize different assay results to those assays reported herein. The following assays may be used to identify matrix metalloproteinase inhibitors.

Inhibition of Human Collagenase (MMP-1)

Human recombinant collagenase is activated with trypsin. The amount of trypsin may be optimized for each lot of collagenase-1 but a typical reaction uses the following ratio: 5 μg trypsin per 100 μg of collagenase. The trypsin and collagenase may be incubated at room temperature for 10 minutes then a five fold excess (50 mg/10 mg trypsin) of soybean trypsin inhibitor is added.

Stock solutions (10 mM) of inhibitors may be made up in dimethylsulfoxide and then diluted using the following scheme:

10 mM→120 μM→12 μM→1.2 μM→0.12 μM

Twenty-five microliters of each concentration may then be added in triplicate to appropriate wells of a 96 well microfluor plate. The final concentration of inhibitor may be a 1:4 dilution after addition of enzyme and substrate. Positive controls (enzyme, no inhibitor) may be set up in wells D7-D12 and negative controls (no enzyme, no inhibitors) may be set in wells D1-D6.

Collagenase-1 may be diluted to 240 ng/ml and 25 µl is then added to appropriate wells of the microfluor plate. Final concentration of collagenase in the assay may be 60 ng/ml.

Substrate (DNP-Pro-Cha-Gly-Cys(Me)-His-Ala-Lys (NMA)-NH$_2$) may be made as a 5 mM stock in dimethylsulfoxide and then diluted to 20 µM in assay buffer. The assay may be initiated by the addition of 50 µl substrate per well of the microfluor plate to give a final concentration of 10 µM.

Fluorescence readings (360 nM excitation, 460 nm emission) may be taken at time 0 and then at 20 minute intervals. The assay may be conducted at room temperature with a typical assay time of 3 hours.

Fluorescence versus time may be then plotted for both the blank and collagenase containing samples (data from triplicate determinations is averaged). A time point that provides a good signal (at least five fold over the blank) and that is on a linear part of the curve (usually around 120 minutes) may be chosen to determine IC$_{50}$ values. The zero time may be used as a blank for each compound at each concentration and these values may be subtracted from the 120-minute data. Data may be plotted as inhibitor concentration versus % control (inhibitor fluorescence divided by fluorescence of collagenase alone×100). IC$_{50}$'s may be determined from the concentration of inhibitor that gives a signal that is 50% of the control.

If IC$_{50}$'s are reported to be less than 0.03 µM then the inhibitors may be assayed at concentrations of 0.3 µM, 0.03 µM and 0.003 µM.

Inhibition of Gelatinase (MMP-2)

Human recombinant 72 kD gelatinase (MMP-2, gelatinase A) may be activated for 16-18 hours with 1mM p-aminophenyl-mercuric acetate (from a freshly prepared 100 mM stock in 0.2 N NaOH) at 4° C., rocking gently.

10 mM dimethylsulfoxide stock solutions of inhibitors may be diluted serially in assay buffer (50 mM TRIS, pH 7.5, 200 mM NaCl, 5 mM CaCl$_2$, 20 µM ZnCl$_2$ and 0.02% BRIJ-35 (vol./vol.)) using the following scheme:

10 mM→120 µM→12 µM→1.2 µM→0.12 µM

Further dilutions may be made as necessary following this same scheme. A minimum of four inhibitor concentrations for each compound may be performed in each assay. 25 µL of each concentration may be then added to triplicate wells of a black 96 well U-bottomed microfluor plate. As the final assay volume may be 100 µL, final concentrations of inhibitor may be the result of a further 1:4 dilution (i.e. 30 µM→3 µM→0.3 µM→0.03 µM etc.). A blank (no enzyme, no inhibitor) and a positive enzyme control (with enzyme, no inhibitor) may be also prepared in triplicate.

Activated enzyme may be diluted to 100 ng/mL in assay buffer, 25 µL per well may be added to appropriate wells of the microplate. Final enzyme concentration in the assay may be 25 ng/mL (0.34 nM).

A five mM dimethylsulfoxide stock solution of substrate (Mca-Pro-Leu-Gly-Leu-Dpa-Ala-Arg-NH$_2$) may be diluted in assay buffer to 20 µM. The assay may be initiated by addition of 50 µL of diluted substrate yielding a final assay concentration of 10 µM substrate. At time zero, fluorescence reading (320 excitation; 390 emission) may be immediately taken and subsequent readings may be taken every fifteen minutes at room temperature with a PerSeptive Biosystems CytoFluor Multi-Well Plate Reader with the gain at 90 units.

The average value of fluorescence of the enzyme and blank may be plotted versus time. An early time point on the linear part of this curve may be chosen for IC$_{50}$ determinations. The zero time point for each compound at each dilution may be subtracted from the latter time point and the data then expressed as percent of enzyme control (inhibitor fluorescence divided by fluorescence of positive enzyme control×100). Data may be plotted as inhibitor concentration versus percent of enzyme control. IC$_{50}$'s may be defined as the concentration of inhibitor that gives a signal that is 50% of the positive enzyme control.

Inhibition of Stromelysin Activity (MMP-3)

Human recombinant stromelysin (MMP-3, stromelysin-1) may be activated for 20–22 hours with 2 mM p-aminophenyl-mercuric acetate (from a freshly prepared 100 mM stock in 0.2 N NaOH) at 37° C.

10 mM dimethylsulfoxide stock solutions of inhibitors may be diluted serially in assay buffer (50 mM TRIS, pH 7.5, 150 mM NaCl, 10 mM CaCl$_2$ and 0.05% BRIJ-35 (vol./vol.)) using the following scheme:

10 mM→120 µM→12 µM→1.2 µM→0.12 µM

Further dilutions may be made as necessary following this same scheme. A minimum of four inhibitor concentrations for each compound may be performed in each assay. 25 µL of each concentration may be then added to triplicate wells of a black 96 well U-bottomed microfluor plate. As the final assay volume may be 100 µL, final concentrations of inhibitor may be the result of a further 1:4 dilution (i.e. 30 µM→3 µM→0.3 µM→0.03 µM, etc.). A blank (no enzyme, no inhibitor) and a positive enzyme control (with enzyme, no inhibitor) may be also prepared in triplicate.

Activated enzyme is diluted to 200 ng/mL in assay buffer, 25 µL per well may be added to appropriate wells of the microplate. Final enzyme concentration in the assay may be 50 ng/mL (0.875 nM).

A ten mM dimethylsulfoxide stock solution of substrate (Mca-Arg-Pro-Lys-Pro-Val-Glu-Nva-Trp-Arg-Lys(Dnp)-NH$_2$) may be diluted in assay buffer to 6 µM. The assay may be initiated by addition of 50 µL of diluted substrate yielding a final assay concentration of 3 µM substrate. At time zero, fluorescence reading (320 excitation; 390 emission) may be immediately taken and subsequent readings may be taken every fifteen minutes at room temperature with a PerSeptive Biosystems CytoFluor Multi-Well Plate Reader with the gain at 90 units.

The average value of fluorescence of the enzyme and blank may be plotted versus time. An early time point on the linear part of this curve may be chosen for IC$_{50}$ determinations. The zero time point for each compound at each dilution may be subtracted from the latter time point and the data then expressed as percent of enzyme control (inhibitor fluorescence divided by fluorescence of positive enzyme control×100). Data may be plotted as inhibitor concentration versus percent of enzyme control. IC$_{50}$'s may be defined as the concentration of inhibitor that gives a signal that is 50% of the positive enzyme control.

Inhibition of Human 92 kD Gelatinase (MMP-9)

Inhibition of 92 kD gelatinase (MMP-9) activity may be assayed using the Mca-Pro-Leu-Gly-Leu-Dpa-Ala-Arg-NH$_2$ substrate (10 µM) under similar conditions as described above for the inhibition of human collagenase (MMP-1).

Human recombinant 92 kD gelatinase (MMP-9, gelatinase B) may be activated for 2 hours with 1 mM p-aminophenyl-mercuric acetate (from a freshly prepared 100 mM stock in 0.2 N NaOH) at 37 C.

10 mM dimethylsulfoxide stock solutions of inhibitors may be diluted serially in assay buffer (50 mM TRIS, pH 7.5, 200 mM NaCl, 5 mM $CaCl_2$, 20 µM $ZnCl_2$, 0.02% BRIJ-35 (vol./vol.)) using the following scheme:

10 mM→120 µM→12 µM→1.2 µM→0.12 µM

Further dilutions may be made as necessary following this same scheme. A minimum of four inhibitor concentrations for each compound may be performed in each assay. 25 µL of each concentration is then added to triplicate wells of a black 96 well U-bottomed microfluor plate. As the final assay volume may be 100 µL, final concentrations of inhibitor may be the result of a further 1:4 dilution (i.e. 30 µM→3 µM→0.3 µM→0.03 µM, etc.). A blank (no enzyme, no inhibitor) and a positive enzyme control (with enzyme, no inhibitor) may be also prepared in triplicate.

Activated enzyme may be diluted to 100 ng/mL in assay buffer, 25 µL per well may be added to appropriate wells of the microplate. Final enzyme concentration in the assay may be 25 ng/mL (0.27 nM).

A five mM dimethylsulfoxide stock solution of substrate (Mca-Pro-Leu-Gly-Leu-Dpa-Ala-Arg-$NH_2$) may be diluted in assay buffer to 20 µM. The assay may be initiated by addition of 50 µL of diluted substrate yielding a final assay concentration of 10 µM substrate. A zero time fluorescence reading (320 excitation; 390 emission) may be immediately taken and subsequent readings may be taken every fifteen minutes at room temperature with a PerSeptive Biosystems CytoFluor Multi-Well Plate Reader with the gain at 90 units.

The average value of fluorescence of the enzyme and blank may be plotted versus time. An early time point on the linear part of this curve may be chosen for $IC_{50}$ determinations. The zero time point for each compound at each dilution may be subtracted from the latter time point and the data then expressed as percent of enzyme control (inhibitor fluorescence divided by fluorescence of positive enzyme control×100). Data may be plotted as inhibitor concentration versus percent of enzyme control. $IC_{50}$'s may be defined as the concentration of inhibitor that gives a signal that is 50% of the positive enzyme control.

Inhibition of MMP-13

Human recombinant MMP-13 may be activated with 2 mM APMA (p-aminophenyl mercuric acetate) for 1.5 hours, at 37° C. and may be diluted to 400 mg/ml in assay buffer (50 mM Tris, pH 7.5, 200 mM sodium chloride, 5 mM calcium chloride, 20 µM zinc chloride, 0.02% brij). Twenty-five microliters of diluted enzyme may be added per well of a 96 well microfluor plate. The enzyme may be then diluted in a 1:4 ratio in the assay by the addition of inhibitor and substrate to give a final concentration in the assay of 100 mg/ml.

10 mM stock solutions of inhibitors may be made up in dimethyl sulfoxide and then diluted in assay buffer as per the inhibitor dilution scheme for inhibition of human collagenase (MMP-1): Twenty-five microliters of each concentration may be added in triplicate to the microfluor plate. The final concentrations in the assay may be 30 µM, 3 µM, 0.3 µM and 0.03 µM.

Substrate (Dnp-Pro-Cha-Gly-Cys(Me)-His-Ala-Lys (NMA)-$NH_2$) may be prepared as for inhibition of human collagenase (MMP-1) and 50 µl may be added to each well to give a final assay concentration of 10 µM. Fluorescence readings (360 nM excitation; 450 emission) may be taken at time 0 and every 5 minutes for 1 hour.

Positive controls may consist of enzyme and substrate with no inhibitor and blanks consist of substrate only.

$IC_{50}$'s may be determined as per inhibition of human collagenase (MMP-1). If $IC_{50}$'s are reported to be less than 0.03 µM, inhibitors may be then assayed at final concentrations of 0.3 µM, 0.03 µM, 0.003 µM and 0.0003 µM.

Collagen Film MMP-13 Assay

Rat type I collagen may be radiolabeled with $^{14}C$ acetic anhydride (T. E. Cawston and A .J. Barrett, *Anal. Biochem.*, 99, 340–345 (1979)) and used to prepare 96 well plates containing radiolabeled collagen films (Barbara Johnson-Wint, *Anal. Biochem.*, 104, 175–181 (1980)). When a solution containing collagenase were added to the well, the enzyme cleaves the insoluble collagen which unwinds and would thus solubilized. Collagenase activity may be directly proportional to the amount of collagen solubilized, determined by the proportion of radioactivity released into the supernatant as measured in a standard scintillation counter. Collagenase inhibitors may be, therefore, compounds which reduce the radioactive counts released with respect to the controls with no inhibitor present. One specific embodiment of this assay may be described in detail below.

For determining the selectivity of compounds for MMP-13 versus MMP-1 using collagen as a substrate, the following procedure may be used. Recombinant human proMMP-13 or proMMP-1 may be activated according to the procedures outlined above. The activated MMP-13 or MMP-1 may be diluted to 0.6 µg/ml with buffer (50 mM Tris pH 7.5, 150 mM NaCl, 10 mM $CaCl_2$, 1 µM $ZnCl_2$, 0.05% Brij-35, 0.02% sodium azide).

Stock solutions of test compound (10 mM) in dimethylsulfoxide may be prepared. Dilutions of the test compounds in the Tris buffer, above, may be made to 0.2, 2.0, 20, 200, 2000 and 20000 nM.

100 µl of appropriate drug dilution and 100 µl of diluted enzyme may be pipetted into wells of a 96 well plate containing collagen films labeled with $^{14}C$-collagen. The final enzyme concentration may be 0.3 µg/ml while the final drug concentration is 0.1, 1.0, 10, 100, 1000 nM. Each drug concentration and control may be analyzed in triplicate. Triplicate controls may be also run for the conditions in which no enzyme may be present and for enzyme in the absence of any compound.

The plates may be incubated at 37° C. for a time period such that around 30–50% of the available collagen may be solubilized. The time period may be determined by counting additional control wells at various time points. In most cases around 9 hours of incubation may be required. When the assay has progressed sufficiently, the supernatant from each well may be removed and counted in a scintillation counter. The background counts (determined by the counts in the wells with no enzyme) may be subtracted from each sample and the % release calculated in relation to the wells with enzyme only and no inhibitor. The triplicate values for each point may be averaged and the data graphed as percent release versus drug concentration. $IC_{50}$'s may be determined from the point at which 50% inhibition of release of radiolabeled collagen may be obtained.

To determine the identity of the active collagenases in cartilage conditioned medium, assays may be conducted using collagen as a substrate, cartilage conditioned medium containing collagenase activity and inhibitors of varying selectivity. The cartilage conditioned medium may be collected during the time at which collagen degradation may be occurring and thus may be representative of the collagenases responsible for the collagen breakdown. Assays may be conducted as outlined above except that instead of using recombinant MMP-13 or recombinant MMP-1, cartilage conditioned medium may be the enzyme source.

IL-1 Induced Cartilage Collagen Degradation from Bovine Nasal Cartilage

This assay may use bovine nasal cartilage explants which are commonly used to test the efficacy of various compounds to inhibit either IL-1 induced proteoglycan degradation or IL-1 induced collagen degradation. Bovine nasal cartilage is a tissue that is very similar to articular cartilage, i.e. chondrocytes surrounded by a matrix that is primarily type II collagen and aggrecan. The tissue may be used because it: (1) is very similar to articular cartilage, (2) is readily available, (3) is relatively homogeneous and (4) degrades with predictable kinetics after IL-1 stimulation.

Two variations of this assay may be used to assay compounds. Both variations may give similar data. The two variations may be described below:

Variation 1

Three plugs of bovine nasal cartilage (approximately 2 mm diameter×1.5 mm long) may be placed into each well of a 24 well tissue culture plate. One ml of serumless medium may be then added to each well. Compounds may be prepared as 10 mM stock solutions in dimethyl sulfoxide and then diluted appropriately in serumless medium to final concentrations, e., 50, 500 and 5000 nM. Each concentration may be assayed in triplicate.

Human recombinant IL-1α (5 ng/mL)(IL-1) may be added to triplicate control wells and to each well containing drug. Triplicate control wells may be also set up in which neither drug nor IL-1 may be added. The medium may be removed and fresh medium containing IL-1 and the appropriate drug concentrations may be added on days 6, 12, 18 and 24 or every 3–4 days if necessary. The media removed at each time point may be stored at −20° C. for later analysis. When the cartilage in the IL-1 alone wells may have been almost completely resorbed (about day 21), the experiment may be terminated. The medium may be removed and stored. Aliquots (100 μl) from each well at each time point may be pooled, digested with papain and then analyzed for hydroxyproline content. Background hydroxyproline (average of wells with no IL-1 and no drug) may be subtracted from each data point and the average calculated for each triplicate. The data may be then expressed as a percent of the IL-1 alone average value and plotted. The $IC_{50}$ may be determined from this plot.

Variation 2

The experimental set-up may be the same as outlined above in Variation 1, until day 12. On day 12, the conditioned medium from each well may be removed and frozen. Then one ml of phosphate buffered saline (PBS) containing 0.5 μg/ml trypsin may be added to each well and incubation continued for a further 48 hours at 37° C. After 48 hours incubation in trypsin, the PBS solution may be removed. Aliquots (50 μl) of the PBS/trypsin solution and the previous two time points (days 6 and 12) may be pooled, hydrolyzed and hydroxyproline content determined. Background hydroxyproline (average of wells with no IL-1 and no drug) may be subtracted from each data point and the average calculated for each triplicate. The data may be then expressed as a percent of the IL-1 alone average value and plotted. The $IC_{50}$ may be determined from this plot. In this variation, the time course of the experiment v shortened considerably. The addition of trypsin for 48 hours after 12 days of IL-1 stimulation likely releases any type II collagen that may have been damaged by collagenase activity but not yet released from the cartilage matrix. In the absence of IL-1 stimulation, trypsin treatment may produce only low background levels of collagen degradation in the cartilage explants.

Inhibition of TNF Production

The ability or inability of the compounds or the pharmaceutically acceptable salts thereof to inhibit the production of TNF may be shown by the following in vitro assay:

Human Monocyte Assay

Human mononuclear cells may be isolated from anticoagulated human blood using a one-step Ficoll-hypaque separation technique. The mononuclear cells may be washed three times in Hanks balanced salt solution (HBSS) with divalent cations and resuspended to a density of $2 \times 10^6$ /ml in HBSS containing 1% BSA. Differential counts may be determined using the Abbott Cell Dyn 3500 analyzer indicated that monocytes ranged from 17 to 24% of the total cells in these preparations.

180 μl of the cell suspension may be aliquoted into flat bottom 96 well plates (Costar). Additions of compounds and LPS (100 ng/ml final concentration) may give a final volume of 200 μl. All conditions may be performed in triplicate. After a four hour incubation at 37° C. in an humidified $CO_2$ incubator, plates may be removed and centrifuged (10 minutes at approximately 250×g) and the supernatants removed and assayed for TNF α using the R&D ELISA Kit.

Aggrecanase Assay

Primary porcine chondrocytes from articular joint cartilage may be isolated by sequential trypsin and collagenase digestion followed by collagenase digestion overnight and may be plated at $2 \times 10^5$ cells per well into 48 well plates with 5 μCi/ml $^{35}$S (1000 Ci/mmol) sulfur in type I collagen coated plates. Cells may be allowed to incorporate label into their proteoglycan matrix (approximately 1 week) at 37° C., under an atmosphere of 5% $CO_2$.

The night before initiating the assay, chondrocyte monolayers may be washed two times in DMEM/1% PSF/G and then allowed to incubate in fresh DMEM/1% FBS overnight.

The following morning chondrocytes may be washed once in DMEM/1%PSF/G. The final wash may be allowed to sit on the plates in the incubator while making dilutions.

Media and dilutions may be made as described in the Table below.

| | |
|---|---|
| Control Media | DMEM alone (control media) |
| IL-1 Media | DMEM + IL-1 (5 ng/ml) |
| Drug Dilutions | Make all compounds stocks at 10 mM in DMSO. Make a 100 μM stock of each compound in DMEM in 96 well plate. Store in freezer overnight. The next day perform serial dilutions in DMEM with IL-1 to 5 μM, 500 nM and 50 nM. |

-continued

> Aspirate final wash from wells and add 50 μl of compound from above dilutions to 450 μl of IL-1 media in appropriate wells of the 48 well plates.
> Final compound concentrations equal 500 nM, 50 nM and 5 nM. All samples completed in triplicate with Control and IL-1 alone samples on each plate.

Plates may be labeled and only the interior 24 wells of the plate may be used. On one of the plates, several columns may be designated as IL-1 (no drug) and Control (no IL-1, no drug). These control columns may be periodically counted to monitor 35S-proteoglycan release. Control and IL-1 media may be added to wells (450 μl) followed by compound (50 μl) so as to initiate the assay. Plates may be incubated at 37° C., with a 5% $CO_2$ atmosphere.

At 40–50% release (when CPM from IL-1 media were 4–5 times control media) as assessed by liquid scintillation counting (LSC) of media samples, the assay may be terminated (9–12 hours). Media may be removed from all wells and placed in scintillation tubes. Scintillate may be added and radioactive counts are acquired (LSC). To solubilize cell layers, 500 μl of papain digestion buffer (0.2 M Tris, pH 7.0, 5 mM EDTA, 5 mM DTT and 1 mg/ml papain) may be added to each well. Plates with digestion solution may be incubated at 60° C. overnight. The cell layer may be removed from the plates the next day and placed in scintillation tubes. Scintillate may be then added and samples counted (LSC).

The percent of released counts from the total present in each well may be determined. Averages of the triplicates may be made with control background subtracted from each well. The percent of compound inhibition may be based on IL-1 samples as 0% inhibition (100% of total counts).

The compounds of the present invention that were tested all have $IC_{50}$'s in at least one of the above assays of less than 100 μM preferably less than 100 nM. Certain preferred groups of compounds possess differential selectivity toward the various MMPs or ADAMs. One group of preferred compounds possesses selective activity towards MMP-13 over MMP-1. Another preferred group of compounds possesses selective activity towards MMP-13 over MMP-1, MMP-3 and MMP-7. Another preferred group of compounds possesses selective activity towards MMP-13 over MMP-1, MMP-3, MMP-7 and MMP-17. Another preferred group of compounds possesses selective activity towards MMP-13 over MMP-1, MMP-2, MMP-3, MMP-7, MMP-9 and MMP-14 Another preferred group of compounds possesses selective activity towards MMP-13 over MMP-12 and MMP-14.

For administration to mammals, including humans, for the inhibition of matrix metalloproteinases, a variety of conventional routes may be used including oral, parenteral (e.g., intravenous, intramuscular or subcutaneous), buccal, anal and topical. In general, the compounds of the invention (hereinafter also known as the active compounds) will be administered at dosages of about 0.1 and 25 mg/kg body weight of the subject to be treated per day, preferably from about 0.3 to 5 mg/kg. Preferably the active compound will be administered orally or parenterally. However, some variation in dosage may necessarily occur depending on the condition of the subject being treated. The person responsible for administration may, in any event, determine the appropriate dose for the individual subject.

The compounds of the present invention may be administered in a wide variety of different dosage forms, in general, the therapeutically effective compounds of this invention may present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc may often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes and, if so desired, emulsifying and/or suspending agents as well, together with such diluents as water, ethanol, propylene glycol, glycerin and various like combinations thereof. In the case of animals, they may be advantageously contained in an animal feed or drinking water in a concentration of 5–5000 ppm, preferably 25 to 500 ppm.

For parenteral administration (intramuscular, intraperitoneal, subcutaneous and intravenous use) a sterile injectable solution of the active ingredient may usually be prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions may be suitable intravenous injection purposes. The oily solutions may be suitable for intraarticular, intramuscular and subcutaneous injection purposes. The preparation of all these solutions under sterile conditions may be readily accomplished by standard pharmaceutical techniques well known to those skilled in the art. In the case of animals, compounds may be administered intramuscularly or subcutaneously at dosage levels of about 0.1 to 50 mg/kg/day, advantageously 0.2 to 10 mg/kg/day given in a single dose or up to 3 divided doses.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention may be conveniently delivered in the form of a solution or suspension from a pump spray container that may be squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

For topical ocular administration, direct application to the affected eye may be employed in the form of a formulation as eyedrops, aerosol, gels or ointments, or can be incorporated into collagen (such as poly-2-hydroxyethylmethacrylate and co-polymers thereof), or a hydrophilic polymer shield. The materials may also be applied as a contact lens or via a local reservoir or as a subconjunctival formulation.

For intraorbital administration a sterile injectable solution of the active ingredient is usually prepared. Solutions of a therapeutic compound of the present invention in an aqueous solution or suspension (particle size less than 10 micron) may be employed. The aqueous solutions should be suitably adjusted and buffered, preferably at a pH between 5 and 8, if necessary and the liquid diluent first rendered isotonic. Small amounts of polymers may be added to increase viscosity or for sustained release (such as cellulosic polymers, Dextran, polyethylene glycol, or alginic acid). These solutions may be suitable for intraorbital injection purposes. The preparation of all these solutions under sterile conditions is readily accomplished by standard pharmaceutical techniques well known to those skilled in the art. In the case of animals, compounds may be administered intraorbitally at dosage levels of about 0.1 to 50 mg/kg/day, advantageously 0.2 to 10 mg/kg/day given in a single dose or up to 3 divided doses.

As with the other routes of administration and corresponding dosage forms described herein, dosage forms intended for oral administration may be also suitably formulated to provide controlled-, sustained- and/or delayed release of the active ingredient. Typically, these would include delayed-release oral tablets, capsules and multiparticulates, as well as enteric-coated tablets and capsules which prevent release and adsorption of the active ingredient in the stomach of the patient and facilitate enteric delivery distal to the stomach, i.e., in the intestine. Other typical oral dosage forms may include sustained-release oral tablets, capsules and multiparticulates which provide systemic delivery of the active ingredient in a controlled manner over a prolonged period of time, e.g., a 24-hour period. Where rapid delivery of the active ingredient is required or desirable, a controlled-release oral dosage form may be prepared in the form of a fast-dissolving tablet, which would also preferably include highly soluble salt forms of the active ingredient.

The following Examples illustrate the preparation of the compounds of the present invention. Melting points were uncorrected. Commercial reagents were utilized without further purification. Chromatography refers to column chromatography performed using 32–63 mm silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure or in vacuo means that a rotary evaporator was used. NMR data were reported in parts per million (δ) and were referenced to the deuterium lock signal from the sample solvent ($CDCl_3$ unless otherwise specified).

EXAMPLE 1

1-(6-{4-[4-(4Fluoro-phenyl)-oxazol-2-yl]-phenoxy}-pyridin-3-yl)-1,7,9-triaza-spiro[4.5]decane-6,8,10-trione

| Example Number | Structure | MW | MS (APCl, m/z): [M + H]+ |
|---|---|---|---|
| 1 | 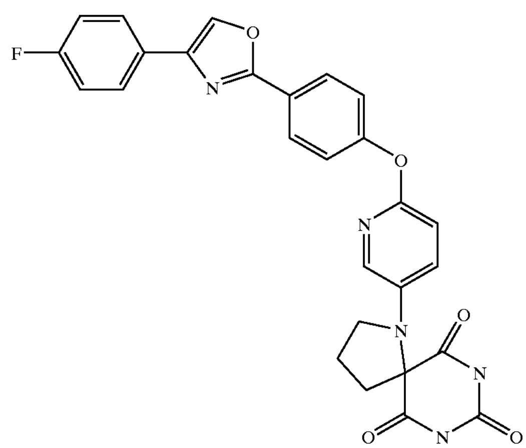 | 513 | 514.0 |

1-(6-{4-[4-(4-Fluoro-phenyl)-oxazol-2-yl]-phenoxy}-pyridin-3-yl)-pyrrolidine-2,2-dicarboxylic acid diethyl ester (5.0 grams, 9.16 mmol) and recrystallized urea (2.75 grams, 45.82 mmol) were dissolved in anhydrous dimethylsulfoxide (110 mL), and the solution was placed in a cold water bath. Sodium hydride (770 mg of a 60% dispersion in mineral oil, 19.23 mmol) was added in two portions. The cold water bath was removed after an addition of the second portion, and the resulting solution was stirred for 1 hour at room temperature. The reaction was then poured into 550 mL water and stirred for 20 minutes until cool. The aqueous layer was extracted three times with diethyl ether, and the combined organic layers were set aside. The pH of the aqueous layer was adjusted to 5 with 1 M hydrochloric acid, and the aqueous layer was extracted three times with ethyl acetate. The combined ethyl acetate layers were washed with water and a solution of saturated sodium chloride, dried over sodium sulfate, and concentrated to give 4.8 grams of crude product as a white foam. This material was chromatographed on silica gel (ISCO MPLC purification, 50 minutes, 0–100% ethyl acetate gradient, Biotage flash 40 m column) to provide 3.44 grams (73%) of the title compound as a white solid. MS m/z: ESI$^+$ 514.0 (M+H)$^+$; ESI$^-$ 512.1 (M–H)$^-$.

Preparation A: 1-(6-{4-[4-(4-Fluoro-phenyl)-oxazol-2-yl]-phenoxyl}-pyridin-3-yl)-pyrrolidine-2,2-dicarboxylic acid diethyl ester Step 1: 4-(4-Fluoro-phenyl)-oxazole (430 mg, 2.64 mmol) was added to a flame dried flask, dissolved in tetrahydrofuran (13.2 mL) and cooled to −78° C. for 20 minutes. n-Butyllithium (1.1 mL, 2.5 M, 2.77 mmol) was added and the solution was stirred for 30 minutes at −78° C. Zinc chloride (8.3 mL, 1 M, 8.3 mmol) was added, the solution was warmed from −78° C. to 0° C., and stirred for 1 hour at 0° C.

Step 2: 1-[6-(4-Iodo-phenoxy)-pyridin-3-yl]-pyrrolidine-2,2-dicarboxylic acid diethyl ester (1 grams, 2.64 mmol) was added to a separate flame dried flask, dissolved in tetrahydrofuran (7 mL) and Pd(PPh$_3$)$_4$ (152 mg, 0.13 mmol) was added to this solution.

Step 3: The organozinc reagent prepared in step 1 was added to the solution prepared in step 2 by cannula. The resulting solution was warmed to 60° C. LC/ESI indicated a complete reaction at 30 minutes. The reaction mixture was cooled to room temperature and quenched by the addition of 50 mL saturated ammonium chloride solution. The mixture was then diluted with 50 mL of ethyl acetate, and the organic layer was washed with 30 mL portions of saturated ammonium chloride, saturated sodium bicarbonate, water, and saturated brine solutions. The organic layer was dried with magnesium sulfate, filtered, and concentrated under vacuum to give 1.5 grams of crude product. The crude product obtained was chromatographed on silica gel (ISCO MPLC purification, 30 minutes, 0–50% ethyl acetate gradient, Biotage flash 40s column) to provide 1 gram (93%) of the title compound. MS m/z: ESI$^+$ 546.3 (M+H)$^+$.

Preparation B: 4-(4-Fluoro-phenyl)-oxazole

2-Bromo-1-(4-fluoro-phenyl)-ethanone (10 grams, 46 mmol), ammonium formate (11 grams, 175 mmol) and formic acid (60 mL) were added to a flask. The mixture was heated to reflux for 3.5 hours. The reaction was then cooled and quenched with 200 mL water. The pH was adjusted to 8 with 50% aqueous sodium hydroxide, and the aqueous layer was extracted with methylene chloride (3×200 mL). The combined organic extracts were dried over sodium sulfate, and concentrated under vacuum. The crude, red solid obtained was choursomatographed on silica gel (ISCO MPLC purification, 50 minutes., 0–25% ethyl acetate gradient, Biotage flash 40 m column) to provide 1.62 grams (22%) of the title compound. MS m/z: ESI$^+$ 164.1 (M+H)$^+$.

Preparation C: 2-(4-Iodo-phenoxy)-5-nitro-pyridine

2-Chloro-5-nitro-pyridine (60 grams, 0.38 mol) and 4-iodo-phenol (83.5 grams, 0.38 mol), 50% aqueous sodium hydroxide (475 mL) and toluene (475 mL) were added to a flask and stirred at room temperature for 2 hours. The reaction mixture was cooled to 0° C. and concentrated hydrochloric acid was added to adjust the pH to two. The aqueous layer was separated from the toluene layer and extracted with diethyl ether (3×400 mL). The diethyl ether and toluene solution were combined and washed with 1M sodium hydroxide (2×300 mL). The organic layer was concentrated under vacuum to yield 96.5 grams of crude product. This material was recrystallized from hexanes and ethyl acetate to provide 85.3 grams (66%) of the title compound. MS m/z: ESI$^+$ 343.0 (M+H)$^+$.

Preparation D: 6-(4-Iodo-phenoxy)-pyridin-3-ylamine 2-(4-Iodo-phenoxy)-5-nitro-pyridine (50 grams, 146.1 mmol) and 4-iodo-phenol (96.5 grams, 438.6 mmol) were dissolved in tetrahydrofuran (500 mL) and added to a Parr shaker flask which contained Raney nickel (30 grams of a 50% slurry in water). The above mixture was shaken under hydrogen gas (50 psi) for 2 hours, at which time uptake of hydrogen gas had ceased and thin liquid chromatography indicated complete consumption of starting material. The Raney nickel was then removed by filtration through a pad of celite under nitrogen. The pad was rinsed several times with methylene chloride. The filtrate was diluted with methylene chloride and the organic layer was washed with 1M sodium hydroxide (4×200 mL) and brine (1×200 mL). The organic layer was dried with magnesium sulfate, filtered and concentrated under vacuum to give 42 grams (92%) of the title compound which was used without further purification. MS m/z: ESI$^+$ 313.0 (M+H)$^+$.

Preparation E: 2-[6-(4-Iodo-phenoxy)-pyridin-3-ylamino]-malonic acid diethyl ester 6-(4-Iodo-phenoxy)-pyridin-3-ylamine (3.54 grams, 11.4 mmol), bromodiethylmalonate (2 mL, 11.4 mmol), and N,N-dimethylaniline (1.5 mL, 11.4 mmol) were combined in a flame dried flask and heated to 70° C. for 3.5 hours., at which time LC/ESI indicated a complete reaction. The mixture was cooled to room temperature, adsorbed to silica gel and chromatographed (gradient elution, 15% ethyl acetate to 25% ethyl acetate) to afford 4.14 grams (77%) of the title compound as a yellow solid. MS m/z: ESI$^+$ 471.1 (M+H)$^+$; ESI-469.3 (M–H)$^-$.

Preparation F: 1-[6-(4-Iodo-phenoxy)-pyridin-3-yl]-pyrrolidine-2,2-dicarboxylic Acid Diethyl Ester 2-[6-(4-Iodo-phenoxy)-pyridin-3-ylamino]-malonic acid diethyl ester (4.35 grams, 9.25 mmol) was added to a flame dried flask and dissolved in dimethylformamide (90 mL). 1,3 dibromopropane (938 μL, 9.25 mmol) and cesium carbonate (6 grams, 18.5 mmol) were added and the reaction mixture was stirred for approximately 24 hours to 48 hours. The solution was filtered through celite, and then concentrated under vacuum while heating to 55° C. to remove the dimethylformamide (azeotroping with toluene). The crude product obtained was chromatographed on silica gel (ISCO MPLC purification, 40 minutes, 0–50% ethyl acetate gradient, Biotage flash 40 m column) to provide 3.39 grams (72%) of the title compound. MS m/z: ESI$^+$ 511.1 (M+H)$^+$.

EXAMPLE 2

4-(2-{4-[5-(6,8,10-Trioxo-1,7,9-triaza-spiro[4.5]dec-1-yl)-pyridin-2-yloxy]-phenyl}-oxazol-4-yl)-benzonitrile

| Example Number | Structure | MW | MS (APCl, m/z): [M + H]+ |
|---|---|---|---|
| 2 | (structure) | 520 | 521.1 |

To a flame dried flask was added ethanol (6 mL) and freshly cut sodium metal (62.4 mg, 2.71 mmol). The solution was stirred until homogenous. Recrystallized urea (98 mg, 1.63 mmol) was added and the solution was stirred at room temperature for 5 minutes. 1-(6-{4-[4-(4-Cyano-phenyl)-oxazol-2-yl]-phenoxy}-pyridin-3-yl)-pyrrolidine-2,2-dicarboxylic acid diethyl ester (300 mg, 0.54 mmol) was added as a solid and the solution was heated to 80° C. for 30 minutes, then cooled to 50° C. and stirred for 16 hours. The reaction was then quenched by the addition of 10 mL water and 1N hydrochloric acid was added to adjust the pH to 5. The aqueous layer was extracted with ethyl acetate (3×20 mL). The combined ethyl acetate layers were washed with saturated sodium chloride, dried with magnesium sulfate, filtered, and concentrated under vacuum to produce 290 mg of crude product. This material was chromatographed on silica gel (ISCO MPLC purification, 30 minutes, 50–100% ethyl acetate gradient, Biotage flash 40 s column) to provide 78 mg of a product which required further purification. Reverse-phase HPLC on a portion of this material provided 15 mg of the title compound as a white solid. MS m/z: ESI+ 521.1 (M+H)+; ESI− 519.3 (M−H)−.

Preparation A: 1-(6-{4-[4-(4-Cyano-phenyl)-oxazol-2-yl]-phenoxy}-pyridin-3-yl)-pyrrolidine-2,2-dicarboxylic acid diethyl ester The title compound was prepared according to the same procedures described in Example 1, Preparation A, but using 4-oxazol-4-yl-benzonitrile. MS m/z: ESI+ 553.0 (M+H)+, ESI− 552.6 (M)−.

Preparation B: 4-Oxazol-4-yl-benzonitrile

The title compound was prepared according to the same procedures described in Example 1, Preparation B, but using 4-(2-bromo-acetyl)-benzonitrile. MS m/z: APCI+ 171.0 (M+H)+.

EXAMPLE 3

3-(2-{4-[5-(6,8,10-Trioxo-1,7,9-triaza-spiro[4.5]dec-1-yl)-pyridin-2-yloxy]-phenyl}-oxazol-4-yl)-benzonitrile

| Example Number | Structure | MW | MS: [M + H]+ |
|---|---|---|---|
| 3 | (structure) | 520 | 521.1 |

The title compound was prepared according to the same procedures described in Example 1, but using 1-(6-{4-[4-(3-Cyano-phenyl)-oxazol-2-yl]-phenoxy}-pyridin-3-yl)-pyrrolidine-2,2-dicarboxylic acid diethyl ester. MS m/z: ESI+ 521.1 (M+H)+; ESI− 519.4 (M−H)−, Preparation A: 1-(6-{4-[4-(3-Cyano-phenyl)-oxazol-2-yl]-phenoxy}-pyridin-3-yl)-pyrrolidine-2,2-dicarboxylic acid diethyl ester The title compound was prepared according to the same procedures described in Example 1, Preparation A, but using 3-oxazol-4-yl-benzonitrile. MS m/z: ESI+ 553.2 (M+H)+.

Preparation B: 3-Oxazol-4-yl-benzonitrile

The title compound was prepared according to the same procedures described in Example 1, Preparation B, but using 3-(2-Bromo-acetyl)-benzonitrile. MS m/z: APCI− 169.1 (M−H)−.

EXAMPLE 4

1-(6-{4-[4-(2-Fluoro-phenyl)-oxazol-2-yl]-phenoxy}-pyridin-3-yl)-1,7,9-triaza-spiro[4.5]decane-6,8,10-trione Preparation A: 1-(6-{4-[4-(2-Fluoro-phenyl)-oxazol-2-yl]-phenoxy}-pyridin-3-yl)-pyrrolidine-2,2-dicarboxylic acid diethyl ester The title compound was prepared according to the same procedures described in Example 1, Preparation A, but using 4-(2-Fluoro-phenyl)-oxazole. MS m/z: ESI+ 546.2 (M+H)+.

Preparation B: 4-(2-Fluoro-phenyl)-oxazole 1-(2-Fluoro-phenyl)-ethanone (2.24 g, 16.23 mmol) and formamide (3.9 mL 97.4 mmol) were added to a flame-dried flask, stirred, and heated to 60° C. Bromine (832 µL, 16.23 mmol) was added dropwise. Upon completion of the bromine addition, the reaction was stirred for 30 minutes, and then the temperature was increased to 125° C. After 3.5 hour further stirring, the reaction mixture was cooled and diluted with 100 mL water. 1N sodium hydroxide was added to increase the pH to about 10. The aqueous layer was extracted twice with diethylether, the combined ether layers were washed with water, dried with magnesium sulfate and concentrated under vacuum. The crude material obtained was

| Example Number | Structure | MW | MS: [M + H]+ |
|---|---|---|---|
| 4 | 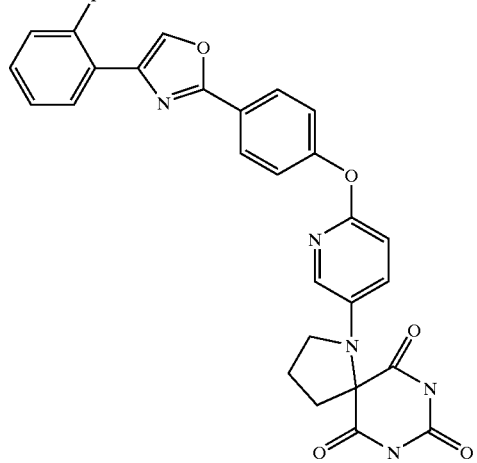 | 513 | 514.1 |

The title compound was prepared according to the same procedures described in Example 1, but using 1-(6-{4-[4-(2-Fluoro-phenyl)-oxazol-2-yl]-phenoxy}-pyridin-3-yl)-pyrrolidine-2,2-dicarboxylic acid diethyl ester. MS m/z: ESI+ 514.1 (M+H)+; ESI− 512.4 (M−H)−.

chromatographed on silica gel (ISCO MPLC purification, 40 minutes, 0–50% ethyl acetate gradient, Biotage flash 40 m column) to provide 580 mg (22%) of the title compound. 1H NMR (400 MHz, CD3OD) δ 8.26 (s, 1H), 8.22 (d, 1H, J=9.9 Hz), 8.0 (m, 1H), 7.3 (m, 3H).

EXAMPLE 5

1-(6-{4-[4-(3-Fluoro-phenyl)-oxazol-2-yl]-phenoxy}-pyridin-3-yl)-1,7,9-triaza-spiro[4.5]decane-6,8,10-trione

| Example Number | Structure | MW | MS: [M + H]+ |
|---|---|---|---|
| 5 | (structure shown) | 513 | 514.2 |

The title compound was prepared according to the same procedures described in Example 1, but using 1-(6-{4-[4-(3-Fluoro-phenyl)-oxazol-2-yl]-phenoxy}-pyridin-3-yl)-pyrrolidine-2,2-dicarboxylic acid diethyl ester. MS m/z: ESI+ 514.2 (M+H)+; ESI− 512.4 (M−H)−.

Preparation A: 1-(6-{4-[4-(3-Fluoro-phenyl)-oxazol-2-yl]-phenoxy}-pyridin-3-yl)-pyrrolidine-2,2-dicarboxylic acid diethyl ester The title compound was prepared according to the same procedures described in Example 1, Preparation A, but using 4-(3-Fluoro-phenyl)-oxazole. MS m/z: ESI+ 546.2 (M+H)+.

Preparation B: 4-(3-Fluoro-phenyl)-oxazole

Step 1: 1-(3-Fluoro-phenyl)-ethanone (10 g, 46 mmol) and dimethylformamide (100 mL) were added to a flame dried flask and stirred at room temperature. Sodium formate (4.07 g, 59.9 mmol) was added and the reaction was stirred for 24 hours. The reaction mixture was then poured into 500 mL water and extracted with methylene chloride. The extracts were combined, washed with water and brine, dried with $Na_2SO_4$, and concentrated under vacuum to provide 7.5 g of crude formate ester.

Step 2: The crude product from step 1 was added to a flask, dissolved in acetic acid (85 mL), ammonium acetate (15.8 g, 205 mmol) was added and the mixture was heated to reflux for 1.5 hours. The reaction mixture was then poured into water and extracted with methylene chloride. The organic layers were combined, washed with saturated sodium carbonate, dried with magnesium sulfate, and concentrated under vacuum to provide 3.03 g crude product. The crude material obtained was chromatographed on silica gel (ISCO MPLC purification, 40 minutes, 0–50% ethyl acetate gradient, Biotage flash 40 m column) to provide 430 mg (6%) of the title compound. MS m/z: APCI+ 164.0 (M+H)+.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed and such expected variations or differences in the results are contemplated in accordance with the objects and practices of the present invention. It is intended, therefore, that the invention be defined by the scope of the claims which follow and that such claims be interpreted as broadly as is reasonable.

We claim:
1. A compound of the formula:

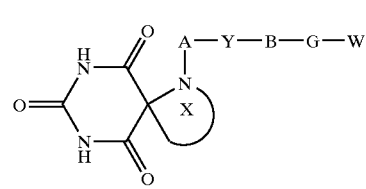

I wherein said ring X is a 5 membered heterocyclic ring selected from the group consisting of:

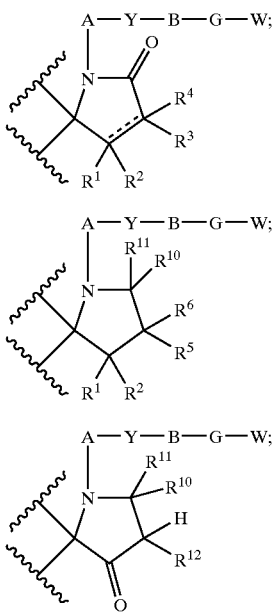

wherein each dashed line represents an optional double bond;

wherein each of $R^1$, $R^2$, $R^3$, $R^4$, $R^5$, $R^6$, $R^{10}$, $R^{11}$, and $R^{12}$ is independently selected from the group consisting of hydrogen, $(C_1-C_4)$alkyl, $(C_1-C_4)$alkenyl, $(C_1-C_4)$alkynyl, $(C_6-C_{10})$aryl, $(C_3-C_{10})$heteroaryl, $(C_3-C_7)$cycloalkyl and $(C_3-C_{10})$heterocyclyl;

wherein each of said $R^1$, $R^2$, $R^3$, $R^4$, $R^5$, $R^6$, $R^{10}$, $R^{11}$, and $R^{12}$ $(C_1-C_4)$alkyl may be optionally substituted by one to three substituents independently selected from the group consisting of F, Cl, Br, CN, OH, —(C=O)—OH, —(C=O)—O—$(C_1-C_4)$alkyl, —(C=O)—NH$_2$, —(C=O)—NH—$(C_1-C_4)$alkyl, —(C=O)—N[$(C_1-C_4)$alkyl]$_2$, $(C_1-C_4)$perfluoroalkyl, $(C_1-C_4)$perfluoroalkoxy, $(C_1-C_4)$alkoxy, —NH$_2$, —NO$_2$, $(C_1-C_4)$alkyl-NH—, [$(C_1-C_4)$alkyl]$_2$—N— and $(C_3-C_7)$cycloalkyloxy;

wherein each of said $R^1$, $R^2$, $R^3$, $R^4$, $R^5$, $R^6$, $R^{10}$, $R^{11}$, and $R^{12}$ $(C_6-C_{10})$aryl, $(C_3-C_{10})$heteroaryl, $(C_3-C_7)$cycloalkyl and $(C_3-C_{10})$heterocyclyl may be optionally substituted on any of the ring carbon atom capable of supporting an additional substituent with one to three substituents per ring independently selected from F, Cl, Br, CN, OH, —(C=O)—OH, —(C=O)—O—$(C_1-C_4)$alkyl, —(C=O)—NH$_2$, —(C=O)—NH—$(C_1-C_4)$alkyl, —(C=O)—N[$(C_1-C_4)$alkyl]$_2$, $(C_1-C_4)$perfluoroalkyl, $(C_1-C_4)$perfluoroalkoxy, $(C_1-C_4)$alkoxy, —NH$_2$, —NO$_2$, $(C_1-C_4)$alkyl-NH—, [$(C_1-C_4)$alkyl]$_2$—N— and $(C_3-C_7)$cycloalkyloxy;

wherein each of said $R^1$, $R^2$, $R^3$, $R^4$, $R^5$, $R^6$, $R^{10}$, $R^{11}$, and $R^{12}$ $(C_3-C_{10})$heteroaryl and $(C_3-C_{10})$heterocyclyl may optionally be substituted on any ring nitrogen atom able to support an additional substituent with one to two substituents per ring independently selected from the group consisting of $(C_1-C_4)$alkyl and $(C_1-C_4)$alkyl-(C=O)—;

wherein each of said each of said $R^1$, $R^2$, $R^3$, $R^4$, $R^5$, $R^6$, $R^{10}$, $R^{11}$, and $R^{12}$ $(C_3-C_7)$cycloalkyl and $(C_3-C_{10})$heterocyclyl may be also optionally substituted on any of the ring carbon atom capable of supporting two additional substituents with one to two oxo groups per ring;

A is $(C_6-C_{10})$arylene or $(C_3-C_{10})$heteroarylene;

Y is selected from the group consisting of a bond, —O—, —S—, >C=O, >SO$_2$, >S=O, —CH$_2$O—, —OCH$_2$—, —CH$_2$S—, —SCH$_2$—, —CH$_2$SO—, —CH$_2$SO$_2$—, —SOCH$_2$—, —SO$_2$CH$_2$—, >NR$^{14}$, —[N(R$^{14}$)]CH$_2$—, —CH$_2$[N(R$^{14}$)]—, —CH$_2$—, —CH=CH—, —C≡C—, —[N(R$^{14}$)]—SO$_2$— and —SO$_2$[N(R$^{14}$)]—;

$R^{14}$ is selected from the group consisting of hydrogen and $(C_1-C_4)$alkyl;

B is selected from the group consisting of $(C_6-C_{10})$arylene, $(C_3-C_7)$cycloalkylene, $(C_3-C_{10})$heterocyclylene and $(C_3-C_{10})$heteroarylene;

wherein one or two carbon-carbon single bonds of said B $(C_3-C_7)$cycloalkylene or $(C_3-C_{10})$heterocyclylene may optionally be replaced by carbon-carbon double bonds;

wherein G is bonded to one ring carbon atom of B;

wherein each of said A or B may be independently optionally substituted on any of the ring carbon atom capable of supporting an additional substituent by one or two substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_7)$cycloalkyloxy;

G is —[$R^{15}$—(CR$^{16}$R$^{17}$)$_p$]—; wherein the group —B—G—W has the formula —B—[$R^{15}$—(CR$^{16}$R$^{17}$)$_p$]—W or —B—[(CR$^{16}$R$^{17}$)$_p$—R$^{15}$]—W;

p is an integer from zero to four;

$R^{15}$ is independently selected from the group consisting of $(C_3-C_7)$cycloalkyl, $(C_6-C_{10})$aryl, $(C_3-C_{10})$heteroaryl and $(C_3-C_{10})$heterocyclyl; wherein each of said $R^{15}$ $(C_3-C_7)$cycloalkyl, $(C_6-C_{10})$aryl, $(C_3-C_{10})$heteroaryl and $(C_3-C_{10})$heterocyclyl may be optionally substituted on any of the ring carbon atom capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy($C_1-C_4)$alkyl, —NH$_2$, —NO$_2$, $(C_1-C_4)$alkyl-NH—, [$(C_1-C_4)$alkyl]$_2$—N—; $(C_3-C_7)$cycloalkyloxy, —(C=O)—OH, —(C=O)—O—$(C_1-C_4)$alkyl, —(C=O)—NH$_2$, —(C=O)—NH—$(C_1-C_4)$alkyl, and —(C=O)—N[$(C_1-C_4)$alkyl]$_2$;

wherein each of said $R^{15}$ $(C_3-C_7)$cycloalkyl and $(C_3-C_{10})$heterocyclyl may optionally be substituted on any ring carbon atom capable of supporting two additional substituents with one to two oxo groups per ring;

wherein each of said $R^{15}$ $(C_3-C_{10})$heteroaryl and $(C_3-C_{10})$heterocyclyl may optionally be substituted on any ring nitrogen atom able to support an additional substituent independently selected from the group consisting of $(C_1-C_4)$alkyl and $(C_1-C_4)$alkyl-(C=O)—;

each of $R^{16}$ and $R^{17}$ is independently selected from the group consisting of hydrogen and $(C_1-C_4)$alkyl;

or $R^{16}$ and $R^{17}$ may optionally be taken together with the carbon to which they are attached to form a 3 to 8-membered carbocyclic ring;

W is selected from the group consisting of $(C_1-C_4)$alkoxy$(C_1-C_4)$alkyl, $(C_3-C_7)$cycloalkyl, $(C_6-C_{10})$aryl, $(C_3-C_{10})$heteroaryl and $(C_3-C_{10})$heterocyclyl;

wherein each of said W $(C_3-C_7)$cycloalkyl, $(C_6-C_{10})$aryl, $(C_3-C_{10})$heteroaryl and $(C_3-C_{10})$heterocyclyl may be optionally substituted on any of the ring carbon atom capable of supporting an additional substituent by one to three substituents per ring independently selected from F, Cl, Br, CN, OH, $(C_1-C_4)$alkyl, $(C_1-C_4)$alkoxy $(C_1-C_4)$alkyl, $(C_1-C_4)$perfluoroalkyl, $(C_1-C_4)$perfluoroalkoxy, $(C_1-C_4)$alkoxy, and $(C_3-C_7)$cycloalkyloxy;

wherein each of said W $(C_3-C_7)$cycloalkyl and $(C_3-C_{10})$heterocyclyl may optionally be substituted on any ring carbon atom capable of supporting two additional substituents with one to two oxo groups per ring;

wherein each of said W $(C_3-C_{10})$heteroaryl and $(C_3-C_{10})$heterocyclyl may optionally be substituted on any ring nitrogen atom able to support an additional substituent independently selected from the group consisting of $(C_1-C_4)$alkyl and $(C_1-C_4)$alkyl-$(C=O)$—;

or a pharmaceutically acceptable salt thereof.

2. The compound according to claim 1 wherein said ring X is

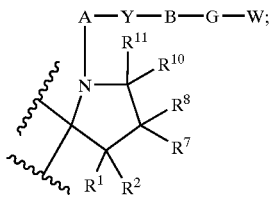

wherein each of $R^1$, $R^2$, $R^7$, $R^8$, $R^{10}$, and $R^{11}$ is independently selected from the group consisting of hydrogen, $(C_1-C_4)$alkyl, $(C_1-C_4)$alkenyl, $(C_1-C_4)$alkynyl, $(C_6-C_{10})$aryl, $(C_3-C_{10})$heteroaryl, $(C_3-C_7)$cycloalkyl and $(C_3-C_{10})$heterocyclyl.

3. The compound according to claim 1 wherein W is $(C_1-C_4)$alkoxy$(C_1-C_4)$alkyl.

4. The compound according to claim 1 wherein W is $(C_3-C_7)$cycloalkyl optionally substituted on any of the ring carbon atom capable of supporting an additional substituent by one to three substituents per ring independently selected from F, Cl, Br, CN, OH, $(C_1-C_4)$alkyl, $(C_1-C_4)$alkoxy $(C_1-C_4)$alkyl, $(C_1-C_4)$perfluoroalkyl, $(C_1-C_4)$perfluoroalkoxy, $(C_1-C_4)$alkoxy, and $(C_3-C_7)$cycloalkyloxy; and wherein said W $(C_3-C_7)$cycloalkyl may optionally be substituted on any ring carbon atom capable of supporting two additional substituents with one to two oxo groups per ring.

5. A compound according to claim 4, wherein said W $(C_3-C_7)$cycloalkyl is selected from the group consisting of cyclopropyl, cyclobutyl, cyclopentyl, cyclohexyl, and cycloheptyl.

6. The compound according to claim 1 wherein W is $(C_6-C_{10})$aryl optionally substituted on any of the ring carbon atom capable of supporting an additional substituent by one to three substituents per ring independently selected from F, Cl, Br, CN, OH, $(C_1-C_4)$alkyl, $(C_1-C_4)$alkoxy $(C_1-C_4)$alkyl, $(C_1-C_4)$perfluoroalkyl, $(C_1-C_4)$perfluoroalkoxy, $C_1-C_4)$alkoxy, and $(C_3-C_7)$cycloalkyloxy.

7. A compound according to claim 1, wherein W is $(C_3-C_{10})$heteroaryl optionally substituted on any of the ring carbon atom capable of supporting an additional substituent by one to three substituents per ring independently selected from F, Cl, Br, CN, OH, $(C_1-C_4)$alkyl, $(C_1-C_4)$alkoxy $(C_1-C_4)$alkyl, $(C_1-C_4)$perfluoroalkyl, $(C_1-C_4)$perfluoroalkoxy, $(C_1-C_4)$alkoxy, and $(C_3-C_7)$cycloalkyloxy; and wherein said W $(C_3-C_{10})$heteroaryl may be also optionally substituted on any ring nitrogen atom able to support an additional substituent independently selected from the group consisting of $(C_1-C_4)$alkyl and $(C_1-C_4)$alkyl-$(C=O)$—.

8. A compound according to claim 7, wherein said W $(C_3-C_{10})$heteroaryl is selected from the group consisting of optionally substituted furyl, imidazolyl, isothiazolyl, isoxazolyl, oxadiazolyl, oxazolyl, pyrazinyl, pyridazinyl, pyridinyl, pyrimidinyl, pyrazolyl, pyrrolyl, tetrazolyl, thiazolyl, thiadiazolyl, thienyl, triazinyl and triazolyl.

9. A compound according to claim 8, wherein said W $(C_3-C_{10})$heteroaryl is selected from the group consisting of optionally substituted pyridinyl, pyridazinyl, pyrazolyl, isoxazolyl, oxadiazolyl, and oxazolyl.

10. A compound according to claim 1, wherein W is $(C_3-C_{10})$heterocyclyl optionally substituted on any of the ring carbon atom capable of supporting an additional substituent by one to three substituents per ring independently selected from F, Cl, Br, CN, OH, $(C_1-C_4)$alkyl, $(C_1-C_4)$alkoxy$(C_1-C_4)$alkyl, $(C_1-C_4)$perfluoroalkyl, $(C_1-C_4)$perfluoroalkoxy, $(C_1-C_4)$alkoxy, and $(C_3-C_7)$cycloalkyloxy; wherein said $(C_1-C_{10})$heterocyclyl may optionally be substituted on any ring carbon atom capable of supporting two additional substituents with one to two oxo groups per ring; and wherein said $(C_1-C_{10})$heterocyclyl may optionally be substituted on any ring nitrogen atom able to support an additional substituent independently selected from the group consisting of $(C_1-C_4)$alkyl and $(C_1-C_4)$alkyl-$(C=O)$—.

11. A compound according to claim 10, wherein said W $(C_3-C_{10})$heterocyclyl is selected from the group consisting of optionally substituted azetidinyl, hexahydroazepinyl, hexahydropyrimidine, morpholinyl, piperazinyl, piperidinyl, pyrrolidinyl, thiomorpholinyl, tetrahydrofuranyl, tetrahydropyranyl, and oxetanyl.

12. The compound according to claim 1, wherein said G is —[$R^{15}$—$(CR^{16}R^{17})_p$]—; wherein p is zero.

13. The compound according to claim 12, wherein G is $(C_3-C_7)$cycloalkylene optionally substituted on any of the ring carbon atom capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, —$NH_2$, —$NO_2$, $(C_1-C_4)$alkyl-NH—, [$(C_1-C_4)$alkyl]$_2$—N—; $(C_3-C_7)$cycloalkyloxy, —(C=O)—OH, —(C=O)—O—$(C_1-C_4)$alkyl, —(C=O)—$NH_2$, —(C=O)—NH—$(C_1-C_4)$alkyl, and —(C=O)—N[$(C_1-C_4)$alkyl]$_2$; and wherein said $R^{15}$ $(C_3-C_7)$cycloalkyl may optionally be substituted on any ring carbon atom capable of supporting two additional substituents with one to two oxo groups per ring.

14. The compound according to claim 12, wherein G is $(C_6-C_{10})$arylene optionally substituted on any of the ring carbon atom capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, —$NH_2$, —$NO_2$, $(C_1-C_4)$alkyl-NH—, [$(C_1-C_4)$alkyl]$_2$—N—; $(C_3-C_7)$cycloalkyloxy, —(C=O)—OH, —(C=O)—O—$(C_1-C_4)$alkyl, —(C=O)—$NH_2$, —(C=O)—NH—$(C_1-C_4)$alkyl, and —(C=O)—N[$(C_1-C_4)$alkyl]$_2$.

15. The compound according to claim 12, wherein G is $(C_3-C_{10})$heteroarylene optionally substituted on any of the ring carbon atom capable of supporting an additional substituent by one to three substituents per ring independently selected from F, Cl, Br, CN, OH, $(C_1-C_4)$alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, —$NH_2$, —$NO_2$, $(C_1-C_4)$alkyl- NH—, [(C$_1$-C$_4$)alkyl]$_2$—N—; (C$_3$-C$_7$)cycloalkyloxy, —(C=O)—OH, —(C=O)—O—(C$_1$-C$_4$)alkyl, —(C=O)—NH$_2$, —(C=O)—NH—(C$_1$-C$_4$)alkyl, and —(C=O)—N[(C$_1$-C$_4$)alkyl]$_2$.

16. The compound according to claim 12, wherein G is (C$_3$-C$_{10}$)heterocyclylene optionally substituted on any of the ring carbon atom capable of supporting an additional substituent by one to three substituents per ring independently selected from F, Cl, Br, CN, OH, (C$_1$-C$_4$)alkyl, (C$_1$-C$_4$)perfluoroalkyl, (C$_1$-C$_4$)perfluoroalkoxy, (C$_1$-C$_4$) alkoxy, (C$_1$-C$_4$)alkoxy(C$_1$-C$_4$)alkyl, —NH$_2$, —NO$_2$, (C$_1$-C$_4$)alkyl-NH—, [(C$_1$-C$_4$)alkyl]$_2$—N—; (C$_3$-C$_7$) cycloalkyloxy, —(C=O)—OH, —(C=O)—O—(C$_1$-C$_4$) alkyl, —(C=O)—NH$_2$, —(C=O)—NH—(C$_1$-C$_4$)alkyl, and —(C=O)—N[(C$_1$-C$_4$)alkyl]$_2$; and wherein said (C$_1$-C$_{10}$)heterocyclyl may optionally be substituted on any ring carbon atom capable of supporting two additional substituents with one to two oxo groups per ring.

17. A compound according to claim 16, wherein G is oxazol-2-yl or oxazol-5-yl optionally substituted on any of the ring carbon atom capable of supporting an additional substituent by one to three substituents per ring independently selected from F, Cl, Br, CN, OH, (C$_1$-C$_4$)alkyl, (C$_1$-C$_4$)perfluoroalkyl, (C$_1$-C$_4$)perfluoroalkoxy, (C$_1$-C$_4$) alkoxy, (C$_1$-C$_4$)alkoxy(C$_1$-C$_4$)alkyl, —NH$_2$, —NO$_2$, (C$_1$-C$_4$)alkyl-NH—, [(C$_1$-C$_4$)alkyl]$_2$—N—; (C$_3$-C$_7$) cycloalkyloxy, —(C=O)—OH, —(C=O)—O—(C$_1$-C$_4$) alkyl, —(C=O)—NH$_2$, —(C=O)—NH—(C$_1$-C$_4$)alkyl, and —(C=O)—N[(C$_1$-C$_4$)alkyl]$_2$.

18. A compound according to claim 16, wherein G is isooxazol-5-yl or isooxazol-3-yl optionally substituted on any of the ring carbon atom capable of supporting an additional substituent by one to three substituents per ring independently selected from F, Cl, Br, CN, OH, (C$_1$-C$_4$) alkyl, (C$_1$-C$_4$)perfluoroalkyl, (C$_1$-C$_4$)perfluoroalkoxy, (C$_1$-C$_4$)alkoxy, (C$_1$-C$_4$)alkoxy(C$_1$-C$_4$)alkyl, —NH$_2$, —NO$_2$, (C$_1$-C$_4$)alkyl-NH—, [(C$_1$-C$_4$)alkyl]$_2$—N—; (C$_3$-C$_7$)cycloalkyloxy, —(C=O)—OH, —(C=O)—O—(C$_1$-C$_4$)alkyl, —(C=O)—NH$_2$, —(C=O)—NH—(C$_1$-C$_4$) alkyl, and —(C=O)—N[(C$_1$-C$_4$)alkyl]$_2$.

19. A compound according to claim 16, wherein G is oxadiazol-2-yl, oxadiazol-3-yl, or oxadiazol-5-yl optionally substituted on any of the ring carbon atom capable of supporting an additional substituent by one to three substituents per ring independently selected from F, Cl, Br, CN, OH, (C$_1$-C$_4$)alkyl, (C$_1$-C$_4$)perfluoroalkyl, (C$_1$-C$_4$) perfluoroalkoxy, (C$_1$-C$_4$)alkoxy, (C$_1$-C$_4$)alkoxy(C$_1$-C$_4$) alkyl, —NH$_2$, —NO$_2$, (C$_1$-C$_4$)alkyl]$_2$—N—; C$_3$-C$_7$) cycloalkyloxy, —(C=O)—OH, —(C=O)—O—(C$_1$-C$_4$) alkyl, —(C=O)—NH$_2$, —(C=O)—NH—(C$_1$-C$_4$)alkyl, and —(C=O)—N[(C$_1$-C$_4$)alkyl]$_2$.

20. A compound according to claim 16, wherein G is pyrazolyl optionally substituted on any of the ring carbon atom capable of supporting an additional substituent by one to three substituents per ring independently selected from F, Cl, Br, CN, OH, (C$_1$-C$_4$)alkyl, (C$_1$-C$_4$)perfluoroalkyl, (C$_1$-C$_4$)perfluoroalkoxy, (C$_1$-C$_4$)alkoxy, (C$_1$-C$_4$)alkoxy (C$_1$-C$_4$)alkyl, —NH$_2$, —NO$_2$, (C$_1$-C$_4$)alkyl-NH—, [(C$_1$-C$_4$)alkyl]$_2$—N—; (C$_3$-C$_7$)cycloalkyloxy, —(C=O)— OH, —(C=O)—O—(C$_1$-C$_4$)alkyl, —(C=O)—NH$_2$, —(C=O)—NH—(C$_1$-C$_4$)alkyl, and —(C=O)—N [(C$_1$-C$_4$)alkyl]$_2$.

21. The compound according to claim 1, wherein said G is —[R$^{15}$—(CR$^{16}$R$^{17}$)$_p$]—; wherein p is an integer from one to four.

22. The compound according to claim 21, wherein G is —[(C$_3$-C$_7$)cycloalkylene-(CR$^{16}$R$^{17}$)$_p$]— optionally substituted on any of the ring carbon atom capable of supporting an additional substituent by one to three substituents per ring independently selected from F, Cl, Br, CN, OH, (C$_1$-C$_4$) alkyl, (C$_1$-C$_4$)perfluoroalkyl, (C$_1$-C$_4$)perfluoroalkoxy, (C$_1$-C$_4$)alkoxy, (C$_1$-C$_4$)alkoxy(C$_1$-C$_4$)alkyl, —NH$_2$, —NO$_2$, (C$_1$-C$_4$)alkyl-NH—, [(C$_1$-C$_4$)alkyl]$_2$—N—; (C$_3$-C$_7$)cycloalkyloxy, —(C=O)—OH, —(C=O)—O— (C$_1$-C$_4$)alkyl, —(C=O)—NH$_2$, —(C=O)—NH—(C$_1$-C$_4$) alkyl, and —(C=O)—N[(C$_1$-C$_4$)alkyl]$_2$; and wherein said (C$_3$-C$_7$)cycloalkyl may optionally be substituted on any ring carbon atom capable of supporting two additional substituents with one to two oxo groups per ring.

23. The compound according to claim 21, wherein G is —[(C$_6$-C$_{10}$)arylene-(CR$^{16}$R$^{17}$)$_p$]— optionally substituted on any of the ring carbon atom capable of supporting an additional substituent by one to three substituents per ring independently selected from F, Cl, Br, CN, OH, (C$_1$-C$_4$) alkyl, (C$_1$-C$_4$)perfluoroalkyl, (C$_1$-C$_4$)perfluoroalkoxy, (C$_1$-C$_4$)alkoxy, (C$_1$-C$_4$)alkoxy(C$_1$-C$_4$)alkyl, —NH$_2$, —NO$_2$, (C$_1$-C$_4$)alkyl-NH—, [(C$_1$-C$_4$)alkyl]$_2$—N—; (C$_3$-C$_7$)cycloalkyloxy, —(C=O)—OH, —(C=O)—O— (C$_1$-C$_4$)alkyl, —(C=O)—NH$_2$, —(C=O)—NH—(C$_1$-C$_4$) alkyl, and —(C=O)—N[(C$_1$-C$_4$)alkyl]$_2$.

24. The compound according to claim 21, wherein G is —[(C$_3$-C$_{10}$)heteroarylene —(CR$^{16}$R$^{17}$)$_p$]— optionally substituted on any of the ring carbon atom capable of supporting an additional substituent by one to three substituents per ring independently selected from F, Cl, Br, CN, OH, (C$_1$-C$_4$) alkyl, (C$_1$-C$_4$)perfluoroalkyl, (C$_1$-C$_4$)perfluoroalkoxy, (C$_1$-C$_4$)alkoxy, (C$_1$-C$_4$)alkoxy(C$_1$-C$_4$)alkyl, —NH$_2$, —NO$_2$, (C$_1$-C$_4$)alkyl-NH—, [(C$_1$-C$_4$)alkyl]$_2$—N—; (C$_3$-C$_7$)cycloalkyloxy, —(C=O)—OH, —(C=O)—O— (C$_1$-C$_4$)alkyl, —(C=O)—NH$_2$, —(C=O)—NH—(C$_1$-C$_4$) alkyl, and —(C=O)—N[(C$_1$-C$_4$)alkyl]$_2$.

25. The compound according to claim 21, wherein G is (C$_3$-C$_{10}$)heterocyclylene —(CR$^{16}$R$^{17}$)$_p$] optionally substituted on any of the ring carbon atom capable of supporting an additional substituent by one to three substituents per ring independently selected from F, Cl, Br, CN, OH, (C$_1$-C$_4$) alkyl, (C$_1$-C$_4$)perfluoroalkyl, (C$_1$-C$_4$)perfluoroalkoxy, (C$_1$-C$_4$)alkoxy, (C$_1$-C$_4$)alkoxy(C$_1$-C$_4$)alkyl, —NH$_2$, —NO$_2$, (C$_1$-C$_4$)alkyl-NH—, [(C$_1$-C$_4$)alkyl]$_2$—N—; (C$_3$-C$_7$)cycloalkyloxy, —(C=O)—OH, —(C=O)—O— (C$_1$-C$_4$)alkyl, —(C=O)—NH$_2$, —(C=O)—NH—(C$_1$-C$_4$) alkyl, and —(C=O)—N[(C$_1$-C$_4$)alkyl]$_2$; and wherein said (C$_1$-C$_{10}$)heterocyclyl may optionally be substituted on any ring carbon atom capable of supporting two additional substituents with one to two oxo groups per ring.

26. The compound according to claim 21, wherein each of R$^{16}$ and R$^{17}$ are hydrogen.

27. The compound according to claim 21, wherein R$^{16}$ and R$^{17}$ are taken together with the carbon to which they are attached to form a 3 to 8-membered carbocyclic ring.

28. A compound according to claim 1, wherein Y is a bond, —O—, —S—, —CH$_2$—, >SO$_2$, —OCH$_2$— or —CH$_2$O—.

29. A compound according to claim 1, wherein Y is —O—, —OCH$_2$— or —CH$_2$O—.

30. A compound according to claim 1, wherein Y is —O—.

31. A compound according to claim 1, wherein A is (C$_6$-C$_{10}$)arylene optionally substituted on any of the ring carbon atoms capable of supporting an additional substituent by one or two substituents per ring independently selected from F, Cl, Br, CN, OH, (C$_1$-C$_4$)alkyl, (C$_1$-C$_4$) perfluoroalkyl, (C$_1$-C$_4$)perfluoroalkoxy, (C$_1$-C$_4$)alkoxy and (C$_3$-C$_7$)cycloalkyloxy.

32. A compound according to claim 1, wherein A is $(C_3-C_{10})$heteroarylene optionally substituted on any of the ring carbon atoms capable of supporting an additional substituent by one or two substituents per ring independently selected from F, Cl, Br, CN, OH, $(C_1-C_4)$alkyl, $(C_1-C_4)$ perfluoroalkyl, $(C_1-C_4)$perfluoroalkoxy, $(C_1-C_4)$alkoxy and $(C_3-C_7)$cycloalkyloxy.

33. The compound according to claim 1 wherein said B is $(C_6-C_{10})$arylene optionally substituted on any of the ring carbon atoms capable of supporting an additional substituent by one or two substituents per ring independently selected from F, Cl, Br, CN, OH, $(C_1-C_4)$alkyl, $(C_1-C_4)$ perfluoroalkyl, $(C_1-C_4)$perfluoroalkoxy, $(C_1-C_4)$alkoxy and $(C_3-C_7)$cycloalkyloxy.

34. The compound according to claim 1 wherein said B is $(C_3-C_7)$cycloalkylene, $(C_3-C_{10})$heteroarylene or $(C_3-C_{10})$ heterocyclylene, wherein each of said $(C_3-C_7)$ cycloalkylene, $(C_3-C_{10})$heteroarylene or $(C_3-C_{10})$ heterocyclylene is optionally substituted on any of the ring carbon atoms capable of supporting an additional substituent by one or two substituents per ring independently selected from F, Cl, Br, CN, OH, $(C_1-C_4)$alkyl, $(C_1-C_4)$ perfluoroalkyl, $(C_1-C_4)$perfluoroalkoxy, $(C_1-C_4)$alkoxy and $(C_3-C_7)$cycloalkyloxy.

35. The compound according to claim 1, wherein the group —B—G—W has the formula —B—[$R^{15}$—($CR^{16}R^{17}$)$_p$]—W.

36. The compound according to claim 1, wherein the group —B—G—W has the formula —B—[($CR^{16}R^{17}$)$_p$—$R^{15}$]—W.

37. The compound according to claim 35, wherein the group —B—G—W has the formula —($C_6-C_{10}$)aryl-[($C_3-C_{10}$)heteroarylene ($CR^{16}R^{17}$)$_p$]—($C_6-C_{10}$)aryl; wherein p is zero; wherein each of said B ($C_6-C_{10}$)aryl and W ($C_6-C_{10}$)aryl is optionally substituted on any of the ring carbon atom capable of supporting an additional substituent by one to three substituents per ring independently selected from F, Cl, Br, CN, OH, $(C_1-C_4)$alkyl, $(C_1-C_4)$ perfluoroalkyl, $(C_1-C_4)$perfluoroalkoxy, $(C_1-C_4)$alkoxy, $(C_1-C_4)$alkoxy$(C_1-C_4)$alkyl, —$NH_2$, $(C_1-C_4)$alkyl-NH—, [$(C_1-C_4)$alkyl]$_2$—N— and $(C_3-C_7)$cycloalkyloxy; and wherein said G $(C_3-C_{10})$heteroarylene is optionally substituted on any of the ring carbon atom capable of supporting an additional substituent by one to three substituents per ring independently selected from F, Cl, Br, CN, OH, $(C_1-C_4)$ alkyl, $(C_1-C_4)$perfluoroalkyl, $(C_1-C_4)$perfluoroalkoxy, $(C_1-C_4)$alkoxy, $(C_1-C_4)$alkoxy$(C_1-C_4)$alkyl, —$NH_2$, —$NO_2$, $(C_1-C_4)$alkyl-NH—, [$(C_1-C_4)$alkyl]$_2$—N—; $(C_3-C_7)$cycloalkyloxy, —(C=O)—OH, —(C=O)—O—$(C_1-C_4)$alkyl, —(C=O)—$NH_2$, —(C=O)—NH—$(C_1-C_4)$ alkyl, and —(C=O)—N[$(C_1-C_4)$alkyl]$_2$.

38. A compound according to claim 1, wherein said compound is selected from the group consisting of:

1-(6-{4-[4-(4-Fluoro-phenyl)-oxazol-2-yl]-phenoxy}-pyridin-3-yl)-1,7,9-triaza-spiro[4.5]decane-6,8,10-trione;

4-(2-{4-[5-(6,8,10-Trioxo-1,7,9-triaza-spiro[4.5]dec-1-yl)-pyridin-2-yloxy]-phenyl}-oxazol-4-yl)-benzonitrile;

3-(2-{4-[5-(6,8,10-Trioxo-1,7,9-triaza-spiro[4.5]dec-1-yl)-pyridin-2-yloxy]-phenyl}-oxazol-4-yl)-benzonitrile;

1-(6-{4-[4-(2-Fluoro-phenyl)-oxazol-2-yl]-phenoxy}-pyridin-3-yl)-1,7,9-triaza-spiro[4.5]decane-6,8,10-trione; and 1-(6-{4-[4-(3-Fluoro-phenyl)-oxazol-2-yl]-phenoxy}-pyridin-3-yl)-1,7,9-triaza-spiro[4.5]decane-6,8,10-trione; or a pharmaceutically acceptable salt thereof.

39. A pharmaceutical composition for the treatment of a condition which can be treated by the inhibition of matrix metalloproteinases in a mammal, including a human, comprising an amount of a compound of claim 1 effective in such treatment and a pharmaceutically acceptable carrier.

40. A method for treating a medical condition of the type that is characterized by the destruction of articular cartilage in a mammalian subject, which method comprises administering to the subject having said condition a therapeutically effective amount of a compound of claim 1, wherein said compound of claim 1 exhibits: i) a ratio of MMP-1 $IC_{50}$/MMP-13 $IC_{50}$ of about 50, and ii) a ratio of MMP-14 $IC_{50}$/MMP-13 $IC_{50}$ of about 50; wherein said MMP-1 $IC_{50}$ is measured by a recombinant MMP-1 assay; wherein each of said MMP-13 $IC_{50}$ is measured by a recombinant MMP-13 assay; and wherein said MMP-14 $IC_{50}$ is measured by a recombinant MMP-14 assay.

41. A method according to claim 40 wherein said compound of claim 1 additionally exhibits iii) a ratio of MMP-12 $IC_{50}$/MMP-13 $IC_{50}$ of about 50; wherein said MMP-12 $IC_{50}$ is measured, by a recombinant MMP-12 assay; and wherein said MMP-13 $IC_{50}$ is measured by a recombinant MMP-13 assay.

42. A method according to claim 41 wherein said compound of claim 1 additionally exhibits iv) a ratio of MMP-2 $IC_{50}$/MMP-13 $IC_{50}$ of about 50, and v) a ratio of MMP-3 $IC_{50}$/MMP-13 $IC_{50}$ of about 50; vi) a ratio of MMP-7 $IC_{50}$/MMP-13 $IC_{50}$ of about 50, and vii) a ratio of MMP-9 $IC_{50}$/MMP-13 $IC_{50}$ of about 50; wherein said MMP-2 $IC_{50}$ is measured by a recombinant MMP-2 assay; wherein said MMP-3 $IC_{50}$ is measured by a recombinant MMP-3 assay; wherein said MMP-7 $IC_{50}$ is measured by a recombinant MMP-7 assay; wherein said MMP-9 $IC_{50}$ is measured by a recombinant MMP-9 assay; and each of said MMP-13 $IC_{50}$ is measured by a recombinant MMP-13 assay.

43. A method according to claim 40 wherein said compound of claim 1 exhibits an MMP-13 $IC_{50}$ of less than about 50 nM.

44. A method according to claim 40 wherein said compound of claim 1 exhibits an MMP-13 $IC_{50}$ of less than about 20 nM.

45. A method of treatment of osteoarthritis in a mammal, the method comprising administering to a mammal in need thereof a pharmaceutically effective amount of a compound of claim 1, or a pharmaceutically acceptable salt thereof.

46. A method of treatment of rheumatoid arthritis in a mammal, the method comprising administering to a mammal in need thereof a pharmaceutically effective amount of a compound of claim 1, or a pharmaceutically acceptable salt thereof.

47. A method of treatment of psoriatic arthritis in a mammal, the method comprising administering to a mammal in need thereof a pharmaceutically effective amount of a compound of claim 1, or a pharmaceutically acceptable salt thereof.

* * * * *